United States Patent
Ishihara et al.

(10) Patent No.: US 11,932,479 B2
(45) Date of Patent: Mar. 19, 2024

(54) METHOD FOR PRODUCING PACKAGE INCLUDING HYDROGEN SULFIDE SUSTAINED RELEASE AGENT, HYDROGEN SULFIDE SUSTAINED RELEASE AGENT, HYDROGEN SULFIDE SUSTAINED RELEASE COMPOSITE, AND METHOD FOR GENERATING HYDROGEN SULFIDE USING SAME

(71) Applicants: NATIONAL INSTITUTE FOR MATERIALS SCIENCE, Tsukuba (JP); SUMITOMO SEIKA CHEMICALS CO., LTD., Hyogo (JP)

(72) Inventors: Shinsuke Ishihara, Tsukuba (JP); Nobuo Iyi, Tsukuba (JP); Daisuke Misho, Hyogo (JP); Noriyuki Hayashizaka, Hyogo (JP)

(73) Assignees: NATIONAL INSTITUTE FOR MATERIALS SCIENCE, Tsukuba (JP); SUMITOMO SEIKA CHEMICALS CO., LTD., Hyogo (JP)

(*) Notice: Subject to any disclaimer, the term of this patent is extended or adjusted under 35 U.S.C. 154(b) by 569 days.

(21) Appl. No.: 17/258,261

(22) PCT Filed: Jun. 28, 2019

(86) PCT No.: PCT/JP2019/025991
§ 371 (c)(1),
(2) Date: Jan. 6, 2021

(87) PCT Pub. No.: WO2020/012994
PCT Pub. Date: Jan. 16, 2020

(65) Prior Publication Data
US 2021/0269231 A1 Sep. 2, 2021

(30) Foreign Application Priority Data
Jul. 12, 2018 (JP) ................................. 2018-132081

(51) Int. Cl.
*B65D 85/00* (2006.01)
*B65D 81/20* (2006.01)
(Continued)

(52) U.S. Cl.
CPC ......... *B65D 85/70* (2013.01); *B65D 81/2023* (2013.01); *C01B 11/14* (2013.01);
(Continued)

(58) Field of Classification Search
CPC ..... B65D 81/2023; B65D 85/70; C01B 11/14; C01B 17/0408; C01B 17/16;
(Continued)

(56) References Cited

U.S. PATENT DOCUMENTS 9,610,538 B2 * 4/2017 Kanatzidis et al. . B01J 20/0285
10,155,040 B2 * 12/2018 Newton et al. ........ A61K 33/32
(Continued)

FOREIGN PATENT DOCUMENTS

CN 1826943 A 9/2006
JP S54-060082 U 4/1979
(Continued)

OTHER PUBLICATIONS

Ono et al., "Solid base catalysis" Fudan Press, pp. 128-129, May 31, 2013.
(Continued)

*Primary Examiner* — Stephen F. Gerrity
(74) *Attorney, Agent, or Firm* — Manabu Kanesaka

(57) ABSTRACT

To provide an inorganic solid material that has a hydrogen sulfide sustained releasability at ordinary temperature in the air atmosphere and is capable of being handled safely and a method for producing the same, and a method for generating hydrogen sulfide using the material. A layered double hydroxide having HS– and/or Sk2– (wherein k represents a positive integer) intercalated among layers (sulfide ion-
(Continued)

containing LDH) is produced, and the sulfide ion-containing LDH is hermetically housed in a packaging material to provide a package. In generating hydrogen sulfide, the packaging material of the package is opened, and the sulfide ion-containing LDH is exposed to the air atmosphere to sustainably release hydrogen sulfide.

19 Claims, 35 Drawing Sheets

(51) Int. Cl.
    *C01B 11/14*     (2006.01)
    *C01B 17/04*     (2006.01)
    *C01B 17/16*     (2006.01)

(52) U.S. Cl.
    CPC .......... *C01B 17/0408* (2013.01); *C01B 17/16* (2013.01); *C01P 2002/08* (2013.01); *C01P 2002/22* (2013.01)

(58) Field of Classification Search
    CPC .... C01B 17/165; C01F 7/162; C01P 2002/08; C01P 2002/22; C01P 2002/72; C01P 2002/78; C01P 2002/82; C01P 2002/88; C01P 2006/32; A61K 33/04
    USPC .............................................. 53/432; 206/0.7
    See application file for complete search history.

(56) References Cited

U.S. PATENT DOCUMENTS

| | | | | |
|---|---|---|---|---|
| 2010/0279848 A1* | 11/2010 | Iyi et al. | ................ | B01D 53/62 502/11 |
| 2013/0313476 A1* | 11/2013 | Iyi et al. | .................. | C09C 1/40 252/194 |
| 2015/0336050 A1 | 11/2015 | Kanatzidis et al. | | |
| 2017/0014750 A1 | 1/2017 | Yoshikawa et al. | | |
| 2019/0038643 A1* | 2/2019 | Wang | ..................... | A61L 15/64 |

FOREIGN PATENT DOCUMENTS

| | | |
|---|---|---|
| JP | 2007-169467 A | 7/2007 |
| JP | 2011-030967 A | 2/2011 |
| JP | 2012-007728 A | 1/2012 |
| JP | 3196215 U | 2/2015 |
| JP | 2015-193000 A | 11/2015 |
| JP | 2015193000 A * | 11/2015 |
| JP | 2016-016369 A | 2/2016 |

OTHER PUBLICATIONS

China National Intellectual Property Administration, "Office Action and Search Report for Chinese Patent Application 201980040674. 5," dated Jul. 7, 2022.
PCT/ISA/210, "International Search Report for International Application No. PCT/JP2019/025991," dated Aug. 27, 2019.
Zhao, Q. et al., Sorptive removal of hydrogen Sulfide from GAs Streams by an Mg-Al Layered Double hydroxide, the Canadian journal of Chemical Engineering, Jul. 2015, vol. 93, pp. 1247-1253.
G. Caliendo et al., "Synthesis and Biological Effects of Hydrogen Sulfide (H2S): Development of H2S-Releasing Drugs as Pharmaceuticals", J. Med. Chem., 2010, vol. 53, p. 6275-6286.
M. Sato, et al., "Characterization of anion exchanged hydrotalcite and determination of the site of exchanged SO4 group", Clay Sci., 1992, vol. 8, p. 309-317.
M. Ogawa and F. Saito, "Easily Oxidizable Polysulfide Anion Occluded in the Interlayer Space of Mg/Al Layered Double Hydroxide", Chem. Lett., 2004, vol. 33, No. 8, p. 1030-1031.
Y. Yokogawa et al., "Synthesis of Microporous Materials and Their VSC Adsorption Properties", 2011 IOP Conf. Ser.: Mater. Sci. Eng., vol. 18, 192011.
N. Iyi, et al., "Water-Swellable MgAl-LDH (Layered Double Hydroxide) Hybrids: Synthesis, Characterization, and Film Preparation", Langmuir, 2008, vol. 24, p. 5591-5598.

* cited by examiner

METHOD FOR PRODUCING PACKAGE INCLUDING HYDROGEN SULFIDE SUSTAINED RELEASE AGENT, HYDROGEN SULFIDE SUSTAINED RELEASE AGENT, HYDROGEN SULFIDE SUSTAINED RELEASE COMPOSITE, AND METHOD FOR GENERATING HYDROGEN SULFIDE USING SAME

RELATED APPLICATIONS

The present application is National Phase of International Application No. PCT/JP2019/025991 filed Jun. 28, 2019, and claims priority from Japanese Application No. 2018-132081, filed Jul. 12, 2018, the disclosure of which is hereby incorporated by reference herein in its entirety.

TECHNICAL FIELD

The present invention relates to a method for producing a package including a hydrogen sulfide sustained release agent, a hydrogen sulfide sustained release agent, a hydrogen sulfide sustained release composite, and a method for generating hydrogen sulfide using the same.

BACKGROUND ART

Hydrogen sulfide ($H_2S$) has the smell of rotten eggs and has been known as a toxic gas. On the other hand, hot springs containing hydrogen sulfide are said to have an efficacy in circulatory diseases and skin diseases, and the usefulness of hydrogen sulfide has been known since old times. In recent years, there are reports that low concentration hydrogen sulfide has bioactivities, such as a cytoprotective activity, a vasorelaxing activity, an antioxidative activity, a neurotransmission regulatory activity, and an apoptotic suppression activity.

As the bioactivities of hydrogen sulfide are revealed, there are active attempts to apply hydrogen sulfide to medical remedies.

However, hydrogen sulfide is in a gas state under ordinary temperature and ordinary pressure, and in many cases, utilized in the form supplied from a pressure cylinder, and therefore medical applications thereof have been limited since the pressure cylinder requires care in transportation and installation, and a serious accident may occur in case of failure in flow rate control of the gas. The use a solution having hydrogen sulfide dissolved therein as a bath additive has been known, but in the case where the solution is used as a hydrogen sulfide gas source, there has been no application beyond a bath additive since the concentration of hydrogen sulfide gas is difficult to control.

Under the circumstances, chemical agents releasing hydrogen sulfide are being developed. Most of the chemical agents of this type are organic compounds, and have an action mechanism that the organic compound undergoes hydrolysis or reduction through direct application to a living body, and thereby hydrogen sulfide is sustainably released (see NPL 1).

As an inorganic solid releasing hydrogen sulfide, salts, such as $Na_2S$ and NaHS, have been known since old times, the hydrogen sulfide releasing mechanism of which is that the salt is immediately hydrolyzed upon contact with water or an acid, so as to release hydrogen sulfide. However, these salts involve danger in handling and disposal after releasing hydrogen sulfide since the salts have deliquescence, and an aqueous solution thereof shows strong alkalinity. Furthermore, these salts have problems including the lack of sustainability of hydrogen sulfide release and the difficulty in controlling the hydrogen sulfide concentration and the release time, and therefore medical applications thereof have been limited.

As an inorganic solid containing sulfur other than the salts described above, there are reports of a layered double hydroxide (LDH) having a polysulfide ion (which may also be referred to as a polysulfide) or a sulfide ion intercalated among the layers (see PTL 1 and NPLs 2 and 3), and a layered double hydroxide (LDH) having hydrogen sulfide adsorbed thereto (see NPL 4). NPL 4 also describes that the layered double hydroxide (LDH) having hydrogen sulfide adsorbed thereto is heated to 500° C. to release adsorbed hydrogen sulfide.

CITATION LIST

Patent Literature

PTL 1: US-A 2015/0336050

Non-Patent Literatures

NPL 1: G. Caliendo et al., "Synthesis and Biological Effects of Hydrogen Sulfide ($H_2S$): Development of $H_2S$-Releasing Drugs as Pharmaceuticals", J. Med. Chem., 2010, Vol. 53, p. 6275-6286

NPL 2: M. Sato, et al., "Characterization of anion exchanged hydrotalcite and determination of the site of exchanged $SO_4$ group", Clay Sci., 1992, Vol. 8, p. 309-317

NPL 3: M. Ogawa and F. Saito, "Easily Oxidizable Polysulfide Anion Occluded in the Interlayer Space of Mg/Al Layered Double Hydroxide", Chem. Lett., 2004, Vol. 33, No. 8, p. 1030-1031

NPL 4: Y. Yokogawa et al., "Synthesis of Microporous Materials and Their VSC Adsorption Properties", 2011 IOP Conf. Ser.: Mater. Sci. Eng., Vol. 18, 192011

NPL 5: N. Iyi, et al., "Water-Swellable MgAl-LDH (Layered Double Hydroxide) Hybrids: Synthesis, Characterization, and Film Preparation", Langmuir, 2008, Vol. 24, p. 5591-5598

SUMMARY OF INVENTION

Technical Problem

However, PTL 1 and NPLs 2 and 3 do not describe the sustained release of hydrogen sulfide by the layered double hydroxide (LDH). NPL 4 does not describe the sustained release of hydrogen sulfide by the layered double hydroxide (LDH) at ordinary temperature.

Accordingly, there has been no report of an inorganic solid material that has a capability of sustainably releasing low concentration hydrogen sulfide, i.e., a hydrogen sulfide sustained releasability, at ordinary temperature in the air atmosphere and is capable of being handled safely. Various medical applications are expected from the material if obtained.

Accordingly, a problem to be solved by the present invention is to provide an inorganic solid material that has a hydrogen sulfide sustained releasability at ordinary temperature in the air atmosphere and is capable of being handled safely and a method for producing the same, and a method for generating hydrogen sulfide using the material.

Solution to Problem

The present inventors focus a layered double hydroxide (LDH) having a hydrogen sulfide source intercalated among layers, as a candidate of the inorganic solid material having hydrogen sulfide sustained releasability on the following basis.

The LDH as a host has layers having positive charge as different from the other many inorganic layered compounds, and thus is one of the few layered inorganic solid materials capable of including an anion among the layers. The LDH is considered to be suitable for the inclusion of an anion species as the hydrogen sulfide source among the layers due to the advantages that the characteristics thereof, such as the ion exchangeability, and the size of crystals can be changed by changing the charge density of the layers, and the material design has a wide range of options. The "inclusion" is a technical term showing the holding between layers.

There is a report about the nature of the LDH that in the case where the anion between layers is a conjugate base of a weak acid, and the LDH is placed in the air atmosphere, due to the action of $H_2CO_3$ formed through reaction of $CO_2$ in the air atmosphere and $H_2O$, the conjugate base is protonated to form a weak acid molecule, simultaneously the anion sites are substituted by $CO_3^{2-}$, and the weak acid molecule if having volatility is released to the air atmosphere (see NPL 5), and the same mechanism possibly works in the present system.

There is no description that the layered double hydroxide (LDH) including a sulfide ion sustainably releases hydrogen sulfide, and this is considered to be because for the layered double hydroxides (LDH) including sulfur described in PTL 1 and NPLs 2 and 3, the removal of oxygen or carbon dioxide of the solvent used in the production thereof is insufficient, and/or there is no sufficient care about the atmosphere during the period of from the introduction of sulfur (hydrogen sulfide source) to the drying to storage of the composite, resulting in reaction of sulfur (hydrogen sulfide source) with oxygen or carbon dioxide, which inhibits the hydrogen sulfide sustained releasability.

In view of the above, the present inventors have found that in the case where the process of production and storage of the layered double hydroxide (LDH) having a hydrogen sulfide source intercalated among layers is performed while restricting contact with oxygen and carbon dioxide, a material that shows the hydrogen sulfide sustained releasability in contact with the air atmosphere at ordinary temperature can be obtained to solve the problem, and thus the present invention has been completed.

To solve the above described problems, the present invention relates to a package including a layered double hydroxide having $HS^-$ and/or $S_k^{2-}$ (wherein k represents a positive integer) intercalated among layers, and a packaging material hermetically housing the layered double hydroxide.

The present invention also relates to, as a production method of the package, a method for producing a package, including: preparing a layered double hydroxide having a monovalent anion other than $HS^-$ and/or $S_k^{2-}$ (wherein k represents a positive integer) intercalated among layers, and a solvent; making the solvent to contain $HS^-$ and/or $S_k^{2-}$ under a nitrogen gas or rare gas atmosphere to provide a solution; bringing the layered double hydroxide having a monovalent anion other than $HS^-$ and/or $S_k^{2-}$ (wherein k represents a positive integer) intercalated among layers into contact with the solution under a nitrogen gas or rare gas atmosphere; separating the solid matter after the contact from the solution, and washing and drying the solid matter, under a nitrogen gas or rare gas atmosphere; and sealing the solid matter after drying in a packaging material.

The present invention also relates to, as a production method of the package, a method for producing a package, including: preparing an aqueous solution containing plural kinds of metal ions, and an alkali solution containing $HS^-$ and/or $S_k^{2-}$ (wherein k represents a positive integer); mixing the aqueous solution and the alkali solution under a nitrogen gas or rare gas atmosphere to provide a precipitate; ripening the solution containing the precipitate under a nitrogen gas or rare gas atmosphere; separating the precipitate after ripening from the solution, and washing and drying the precipitate, under a nitrogen gas or rare gas atmosphere; and sealing the solid matter after drying in a packaging material.

The present invention also relates to a hydrogen sulfide sustained release agent containing the layered double hydroxide having $HS^-$ and/or $S_k^{2-}$ (wherein k represents a positive integer) intercalated among layers, and a method for generating hydrogen sulfide using the same.

Advantageous Effects of Invention

According to the present invention, an inorganic solid material that has a hydrogen sulfide sustained releasability at ordinary temperature in the air atmosphere and a method for generating hydrogen sulfide using the material can be provided.

DESCRIPTION OF EMBODIMENTS

The package, the method for producing a package, the hydrogen sulfide sustained release agent derived from the package, and the method for generating hydrogen sulfide using the hydrogen sulfide sustained release agent according to one embodiment of the present invention (which may be hereinafter referred to as the "present embodiment") will be described below with reference to the drawings.

[Package]

The package of the present embodiment includes a layered double hydroxide having $HS^-$ and/or $S_k^{2-}$ (wherein k represents a positive integer) intercalated among layers, and a packaging material hermetically housing the layered double hydroxide.

Figure 1:
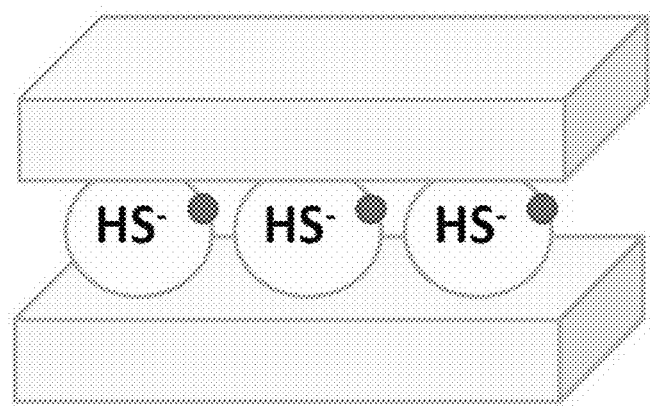
FIG. 1 is a schematic illustration showing the structure of a sulfide ion-containing LDH having a hydrogen sulfide source (HS) intercalated among layers of the layered double hydroxide.

The layered double hydroxide having $HS^-$ and/or $S_k^{2-}$ (wherein k represents a positive integer) intercalated among layers (which may be hereinafter referred to as a "sulfide ion-containing LDH") has a structure having $HS^-$ and/or $S_k^{2-}$ (wherein k represents a positive integer) that is intercalated among the layers of the layered double hydroxide (LDH) as shown in FIG. 1. Herein, $HS^-$ is a hydrogen sulfide ion, and $S_k^{2-}$ is a sulfide ion when k is 1 and a polysulfide ion when k is 2 or more. The anion containing sulfur positioned between the layers of the LDH is considered to be mainly $HS^-$ reflecting the existing ratios of the ion species in the aqueous solution, but the ion species is difficult to identify since these ion species and the oxidized states thereof exist as mixture, and therefore in the description herein, the expression "$HS^-$ and/or $S_k^{2-}$ (wherein k represents a positive integer)" is used as the comprehensive expression of the sulfur-containing anions as the hydrogen sulfide source. In the figure, only $HS^-$ is shown for simplicity, but actually it is considered that the ion species described above besides $HS^-$ exist as mixture.

The LDH has layers having positive charge as different from the other many inorganic layered compounds as described above, and thus is one of the few compounds capable of intercalating an anion among the layers (interlayer). Accordingly, it is considered that the LDH can intercalate $HS^-$ and/or $S_k^{2-}$ among the layers.

The sulfide ion-containing LDH is preferably represented by the following general formula (1).

$$Q_xR(OH)_{2(x+1)}\{(HS^-,0.5S_k^{2-})_yZ_t\}\cdot nH_2O \tag{1}$$

In the formula (1), Q represents a divalent metal ion, R represents a trivalent metal ion, and Z represents an anion other than $HS^-$ and/or $S_k^{2-}$. In the formula (1), x, y, and t represent numbers satisfying $1.8 \leq x \leq 4.2$, $0.01 \leq y \leq 2.0$, and $0 \leq t \leq 1.0$, and n represents a number varying depending on the humidity of the environment.

In the formula (1), Z represents an anion that is derived from the raw material or the solvent used in the production of the sulfide ion-containing LDH, or the atmosphere in the production or storage of the sulfide ion-containing LDH, and examples thereof include $OH^-$, $Cl^-$, $Br^-$, $I^-$, $F^-$, $NO_3^-$, $ClO_4^-$, $SO_4^{2-}$, $CO_3^{2-}$, an acetate anion ($CH_3$—$COO^-$), a propionate anion ($CH_3CH_2COO^-$), a lactate anion ($CH_3$—$CH(OH)$—$COO^-$), and an isethionate anion ($HOC_2H_4SO_3^-$).

As described above, the ion species of sulfur included in an anion positioned among the layers of the LDH is difficult to identify since it includes various oxidized states as mixture, and therefore for expressing the sulfide ion-containing LDH as the general formula, the sulfur-containing anion as the hydrogen sulfide source is represented by "$HS^-,0.5S_k^{2-}$".

In the sulfide ion-containing LDH represented by the general formula (1), it is preferred that Q is selected from the group consisting of $Mg^{2+}$, $Mn^{2+}$, $Fe^{2+}$, $Co^{2+}$, $Ni^{2+}$, $Cu^{2+}$, $Zn^{2+}$, and $Ca^{2+}$, and R is selected from the group consisting of $Al^{3+}$, $Ga^{3+}$, $Cr^{3+}$, $Mn^{3+}$, $Fe^{3+}$, $Co^{3+}$, and $Ni^{3+}$, and it is more preferred that Q is $Mg^{2+}$, and R is $Al^{3+}$.

The MgAl type layered double hydroxide containing Mg and Al as the constitutional elements, which is the most common solid material among the layered double hydroxides, can be synthesized inexpensively, and thus is industrially produced (for example, as Synthetic Hydrotalcite, available from Kyowa Chemical Industry Co., Ltd.). The material causes no problem in attachment to the skin or the like, and has been used in gastrointestinal drugs (such as gastric antacids) and the like. Furthermore, the material has been studied from the medical standpoint as a carrier for the drug delivery system (DDS), and the like, and has achieved results in the application to the medical field. Therefore, the sulfide ion-containing LDH having the MgAl type layered double hydroxide as the basic structure, wherein Q represents $Mg^{2+}$ and R represents $Al^{3+}$, is considered to be excellent in safety.

The shape, the structure, the size, and the like of the packaging material used in the present embodiment are not limited, as far as the prescribed amount of the hydrogen sulfide sustained release agent can be housed, and the hydrogen sulfide sustained releasability of the hydrogen sulfide sustained release agent can be retained for the prescribed period of time. The material of the packaging material is not limited, as far as the material does not react with the hydrogen sulfide sustained release agent, has a gas barrier capability inhibiting the transmission of carbon dioxide, water, oxygen, and the like, and is not broken in the ordinary storage method. Examples thereof include a glass vessel hermetically sealed, and a sealed bag formed of such a material as an aluminum laminated film with the outer periphery thereof fusion-sealed.

In the present embodiment, it is preferred that the interior of the packaging material hermetically housing the sulfide ion-containing LDH is in a volume reduction state or in a vacuum or an inert gas atmosphere from the standpoint of the enhancement of the storage stability of the sulfide ion-containing LDH. In the description herein, the "volume reduction state" means, with respect to a packaging material having flexibility, the state where the capacity of the packaging material is reduced to half or less of the fully charged state through evacuation of the gas from the packaging material, the "vacuum" means the state obtained by decompressing from the atmospheric pressure (i.e., a pressure lower than the atmospheric pressure), and the "inert gas atmosphere" means an atmosphere having contents of oxygen gas and carbon dioxide gas lower than the air atmosphere. Examples of the inert gas atmosphere include a nitrogen gas atmosphere having a content of nitrogen gas larger than the air atmosphere, a rare gas atmosphere having a content of a rare gas larger than the air atmosphere, and a reducing atmosphere with a hydrogen-containing gas.

[Production Method of Package]

The package according to the present embodiment may be produced by preparing a layered double hydroxide having a monovalent anion other than $HS^-$ and/or $S_k^{2-}$ (wherein k represents a positive integer) intercalated among layers, and a solvent; making the solvent to contain $HS^-$ and/or $S_k^{2-}$ under a nitrogen gas or rare gas atmosphere to provide a solution; bringing the layered double hydroxide having a monovalent anion other than $HS^-$ and/or $S_k^{2-}$ (wherein k represents a positive integer) intercalated among layers into contact with the solution under a nitrogen gas or rare gas atmosphere; separating the solid matter after the contact from the solution, and washing and drying the solid matter, under a nitrogen gas or rare gas atmosphere; and sealing the solid matter after drying in a packaging material.

The layered double hydroxide having a monovalent anion other than $HS^-$ and/or $S_k^{2-}$ intercalated among layers used as the starting material (which may be hereinafter referred to as a "raw material LDH") is not limited, as far as the anion can be desorbed through ion exchange or heating. Examples thereof include a material represented by the following general formula (1)'.

$$Q_xR(OH)_{2(x+1)}\{(CO_3^{2-})_{0.5-a/2}(X)_a\}\cdot nH_2O \tag{1'}$$

In the formula (1)', Q represents a divalent metal ion, R represents a trivalent metal ion, and X represents one or more kind selected from an anion having high ion exchangeability, such as a chloride ion ($Cl^-$), a bromide ion ($Br^-$), a nitrate ion ($NO_3^-$), a perchlorate ion ($ClO_4^-$), a chlorate ion ($ClO_3^-$), an acetate anion ($CH_3COO^-$), a propionate anion ($CH_3CH_2COO^-$), a lactate anion ($CH_3$—$CH(OH)$—$COO^-$), and an isethionate anion ($HOC_2H_4SO_3^-$). In the formula (1)', x and a represent numbers satisfying $1.8 \leq x \leq 4.2$ and $0 \leq a \leq 1$, and n represents a number varying depending on the humidity of the environment.

The solvent used is not limited, as far as the solvent can stably dissolve and disperse $HS^-$ and/or $S_k^{2-}$ as the sulfur-containing anion, and can supply the ion-containing anion to an interlayer of the layered double hydroxide. Examples thereof include ion exchanged water, methanol, and ethanol.

The solvent preferably has concentrations of dissolved oxygen and carbon dioxide decreased through bubbling with nitrogen gas or a rare gas, and for water, through heating or the like in combination, before making the solvent to contain $HS^-$ and/or $S_k^{2-}$, from the standpoint of the enhancement of the stability of the $HS^-$ and/or $S_k^{2-}$ contained and the sulfide ion-containing LDH formed.

The solvent can be made to contain $HS^-$ and/or $S_k^-$ by adding a substance that forms the anion through dissolution thereof into the solvent, under a nitrogen gas or rare gas atmosphere.

Examples of the measure for providing the nitrogen gas or rare gas atmosphere include a glove box filled with any of the gases. A measure for controlling the atmosphere in synthesis using a Schlenk flask may also be applied. In the operations described in the following, the operations to be performed under a nitrogen gas or rare gas atmosphere can be performed in the same manner as above, and therefore the description relating to the atmosphere is omitted.

The substance to be added to the solvent is not limited, and examples thereof include hydrogen sulfide ($H_2S$) and a substance represented by the following general formula (2).

$$MH_pS_q \cdot mH_2O \qquad (2)$$

In the formula (2), M represents an alkali metal or an alkaline earth metal, provided that the alkaline earth metal herein includes Mg. In the formula (2), p represents 0 or 1, q represents a number satisfying $0.5 \leq q \leq 6.0$, and m represents a number varying depending on the humidity of the environment.

The method for bringing the raw material LDH into contact with the solution containing $HS^-$ and/or $S_k^{2-}$ is not limited, as far as both the materials can be brought into sufficient contact with each other, and $HS^-$ and/or $S_k^{2-}$ are supplied to the interlayer of the raw material LDH. Examples thereof include pouring the solution into a vessel having the raw material LDH therein, placing the raw material LDH into a vessel having the solution therein, and continuously placing the raw material LDH into a flow channel where the solution flows. In the case where both the materials are brought into contact in a vessel, the mixture in the vessel is preferably stirred from the standpoint of the acceleration of the supply of $HS^-$ and/or $S_k^{2-}$ to the interlayer of the raw material LDH.

In the case where a material represented by the general formula (1)', in which the value of a is small, i.e., the proportion of a carbonate ion ($CO_3^{2-}$) occupied in the anion among the layer is large, (which may be hereinafter referred to as a "carbonate type LDH") is used as the raw material LDH, a carbonate ion is hard to desorb from the interlayer, and therefore at least a part of a carbonate ion is preferably removed from the interlayer by performing any of the following treatments preceding the contact with the solution.

The first treatment is that the carbonate type LDH is brought into contact with an acidic compound containing a monovalent anion (such as $Cl^-$ and $NO_3^-$) in an alcohol, so as to convert to an easily anion exchangeable LDH having the anion intercalated among layers, and the method of performing the treatment and then bringing into contact with the solution containing $HS^-$ and/or $S_k^{2-}$ is referred to as an "ion exchange method".

Figure 2:
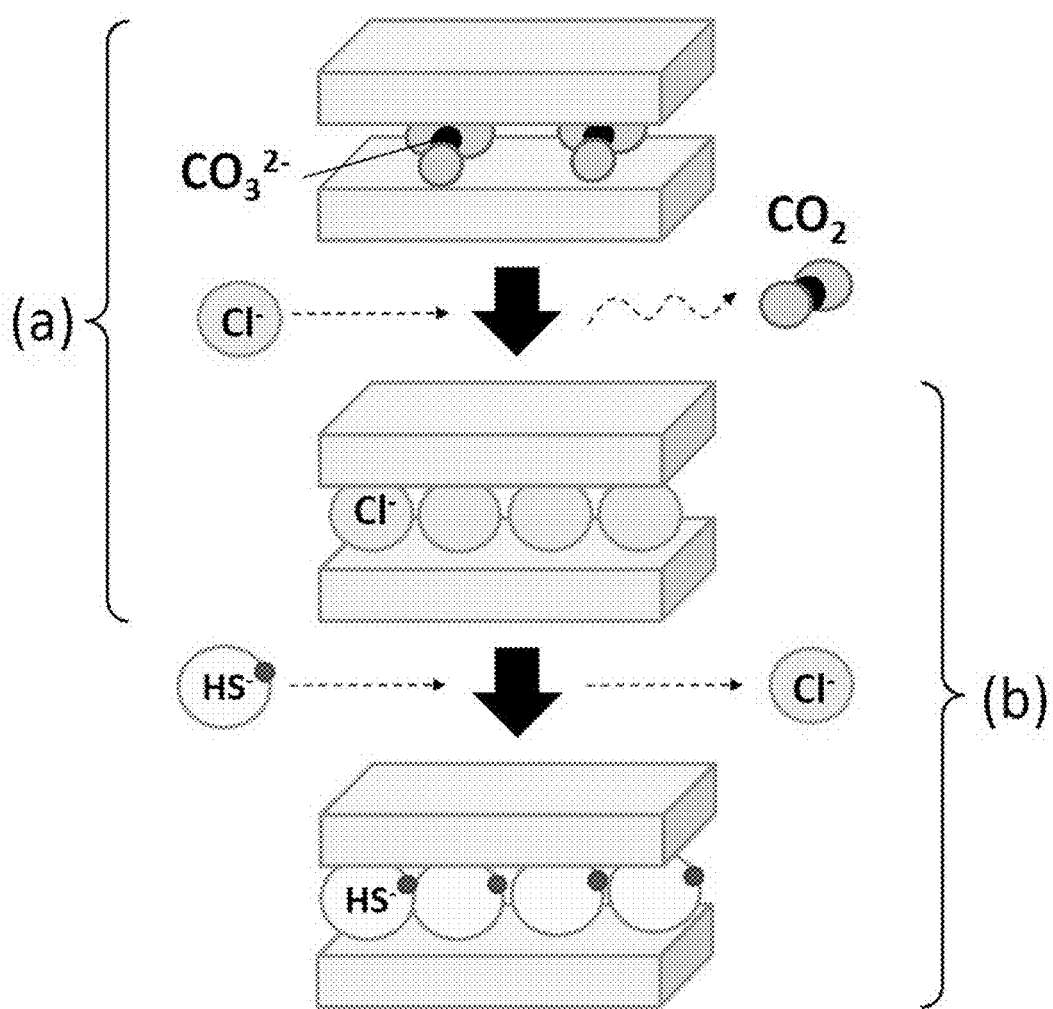
FIG. 2 is a schematic illustration showing an example of the synthesis scheme of the sulfide ion-containing LDH.

The sequence of reaction in the ion exchange method is schematically shown in FIG. 2. The section (a) in the figure shows the reaction forming an easily anion exchangeable LDH from the carbonate type LDH, and the section (b) in the figure shows the reaction forming the sulfide ion-containing LDH from the easily anion exchangeable LDH. The figure shows the case where the reaction undergoes via an LDH having a chloride ion intercalated among the layers (i.e., a Cl type LDH) as the easily anion exchangeable LDH, and the same reaction occurs in the case where the reaction undergoes via other easily anion exchangeable LDH.

The easily anion exchangeable LDH obtained through removal of a carbonate ion (decarbonation) from the carbonate LDH is shown by the following general formula (3).

$$Q_xR(OH)_{2(x+1)}X \cdot nH_2O \qquad (3)$$

In the formula (3), Q represents a divalent metal ion, R represents a trivalent metal ion, and X represents a monovalent anion. In the formula (3), x represents a number satisfying $1.8 \leq x \leq 4.2$, and n represents a number varying depending on the humidity of the environment.

The easily anion exchangeable LDH thus obtained is brought into contact with the solution containing $HS^-$ and/or $S_k^{2-}$, and thereby the anion among the layers is substituted by $HS^-$ and/or $S_k^{2-}$, so as to provide the sulfide ion-containing LDH, as shown in FIG. 2(b).

Since $H_2S$ is also an acidic compound, the application of $H_2S$ in the section (a) as the initial stage can perform a single step ion exchange of $CO_3^{2-}$ of the carbonate type LDH by $HS^-$ and/or $S_k^{2-}$, so as to convert to the sulfide ion-containing LDH.

The second treatment is that the decarbonation is performed through breakage of the layer structure by heat-treating the carbonate type LDH to 500° C. to 600° C., and the method of performing the treatment and then bringing into contact with the solution containing $HS^-$ and/or $S_k^{2-}$ is referred to as a "reconstruction method". According to the reconstruction method, $HS^-$ and/or $S_k^{2-}$ in the solvent are incorporated to the interlayer simultaneously with the reconstructing of the layer structure, thereby providing the sulfide ion-containing LDH.

The method used for separating the solid matter obtained through contact with the solution containing $HS^-$ and/or $S_k^{2-}$ from the solution may be an ordinary solid-liquid separation method, such as filtration and centrifugal separation.

The method used for washing the solid matter after separation may be a method of bringing the solid matter into contact with a clean solvent and then removing the solvent. The clean solvent, with which the solid matter is brought into contact, preferably has concentrations of oxygen and carbon dioxide dissolved therein decreased through bubbling with nitrogen gas or a rare gas, heating, or the like.

The method used for drying the solid matter after washing may be an ordinary method, such as drying by heating and drying under reduced pressure. The drying under reduced pressure is preferred from the standpoint of the suppression of degeneration of the sulfide ion-containing LDH and discharge of hydrogen sulfide therefrom.

The method used for hermetically housing the solid matter after drying may be a method of placing the solid matter into a packaging material having an opening and then sealing the opening. This operation may be performed in the air atmosphere. At this time, it is preferred that the opening is sealed after expelling the air inside through deaeration of the interior of the packaging material from the standpoint that the amount of the air in contact with the solid matter is decreased to enhance the storage stability of the solid matter (sulfide ion-containing LDH). In the case where the operation is performed under an inert gas atmosphere, the interior of the packaging material can be an inert gas atmosphere, and in the case where the interior of the packaging material is deaerated prior to the sealing of the opening, the interior of the packaging material can be in a volume reduction state or vacuum, both of which are more preferred from the standpoint of the enhancement of the storage stability of the solid matter (sulfide ion-containing LDH). The method for making the interior of the packaging material to be a volume reduction state or vacuum, or an inert gas atmosphere is not limited thereto, and any method that can be generally recalled by those skilled in the art may be used.

The solid matter after drying starts the release of hydrogen sulfide by bringing into contact with the air atmosphere as described later, and the release of hydrogen sulfide can be suppressed or terminated in the middle stage by placing the solid matter during the course of the sustained release into an inert gas atmosphere, vacuum, or a volume reduction state.

The feature of the present embodiment is that not only the ion exchange reaction, but also all the process steps including the preparation of the solution as the preceding step thereof and the filtration, washing, and drying as the subsequent step thereof are performed in an inert atmosphere, and furthermore the resulting sulfide ion-containing LDH is hermetically housed in the packaging material, thereby enabling the retention of the sulfur-containing anion as the hydrogen sulfide source among the layers, and exhibiting the hydrogen sulfide sustained releasability.

As for the sulfide ion-containing LDH having been reported, it is understood that at least a part of the production process thereof and the handling thereof, such as drying and storing, are performed in the air atmosphere, and therefore, as shown in the example described below, the sulfur-containing anion (i.e., the hydrogen sulfide source) is not retained among the layers in an amount that is sufficient for the sustained release of hydrogen sulfide.

One example of the method for producing the package according to the present embodiment is described above, but the package according to the present embodiment can be produced by other methods. For example, a "coprecipitation method" may be employed, in which in the production of the sulfide ion-containing LDH, an aqueous solution containing plural kinds of metal ions forming a cation layer and an alkali solution containing a sulfide ion, such as a sodium sulfide aqueous solution, are mixed and ripened. This method utilizes the phenomenon that the anion component of the alkali aqueous solution used in the synthesis of the LDH by the coprecipitation method is intercalated among the layers. As another production method, a special synthesis method may also be employed, in which a solution containing the prescribed anion is added to the LDH having been swollen or formed into a nanosheet, so as to aggregate them to form the sulfide ion-containing LDH.

In the synthesis of an LDH, ripening is often performed for the purpose of the enhancement of the crystallinity, and an "LDH-like" compound formed through insufficient ripening or the like and having low crystallinity is encompassed in the sulfide ion-containing LDH in the description herein, as far as diffraction corresponding to the bottom spacing (i.e., the spacing between the layers) is detected in the powder X-ray structural analysis, and the sulfur-containing anion functioning as the hydrogen sulfide source is contained.

[Hydrogen Sulfide Sustained Release Agent and Method for Generating Hydrogen Sulfide]

The hydrogen sulfide sustained release agent according to the present embodiment is obtained by opening the packaging material of the package described above, and exposing the sulfide ion-containing LDH to the air atmosphere. The method for generating hydrogen sulfide according to the present embodiment includes sustained release of hydrogen sulfide with the hydrogen sulfide sustained release agent.

In the present embodiment, the basis of the use of the sulfide ion-containing LDH as a hydrogen sulfide sustained release agent, i.e., an inorganic solid material that sustainably releases hydrogen sulfide, is that the sulfide ion-containing LDH is considered to release sustainably hydrogen sulfide through the following mechanism.

As described in NPL 5, a conjugate base of a weak acid intercalated among the layers of an LDH is protonated with $H_2CO_3$ formed through the reaction of $CO_2$ in the air atmosphere with $H_2O$ to form a weak acid molecule, and the molecule if having volatility may be possibly released to the air atmosphere. $HS^-$ and $S_k^{2-}$ are conjugate bases of $H_2S$, which is a weak acid, and therefore in the case where the sulfide ion-containing LDH is placed in the atmosphere, it is considered that the anions is released as $H_2S$ to the air atmosphere. The chemical reaction in this case is shown by the following chemical formula (4).

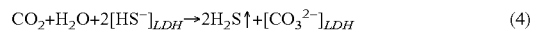

$$CO_2+H_2O+2[HS^-]_{LDH} \rightarrow 2H_2S\uparrow+[CO_3^{2-}]_{LDH} \qquad (4)$$

In the formula, $[\ ]_{LDH}$ means the existence among the LDH layers.

Figure 3:
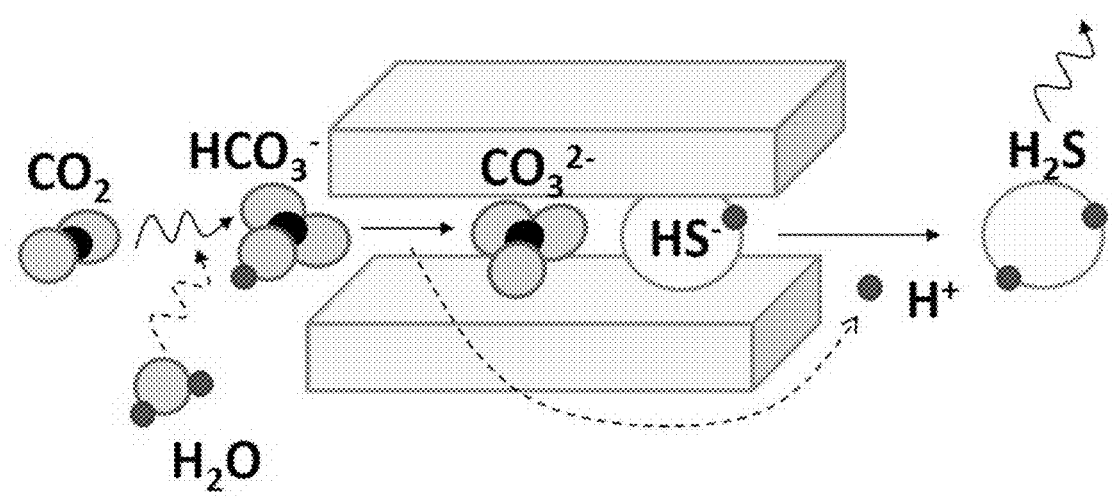
FIG. 3 is a schematic illustration showing the mechanism of releasing hydrogen sulfide from the sulfide ion-containing LDH.

In the sequence of reaction, it is considered that as shown in FIG. 3, $CO_2$ in the air atmosphere enters into the interlayer of the sulfide ion-containing LDH and reacts with $H_2O$ existing in the air atmosphere or in the interlayer to form a proton $H^+$ and a $CO_3^{2-}$ ion, and $CO_3^{2-}$ thus formed undergoes anion exchange with $HS^-$ and/or $S_k^{2-}$ in the interlayer, simultaneously $H^+$ thus formed is bonded to $HS^-$ and/or $S_k^{2-}$ to form hydrogen sulfide ($H_2S$), which is released as hydrogen sulfide gas to the air atmosphere. Accordingly, the diffusion process including the entry of gas into the interlayer and the release of gas from the interlayer is necessarily performed, and consequently it is considered that the reaction is continued for a prolonged period of time, which is observed as the sustained release of hydrogen sulfide.

In the description herein, the hydrogen sulfide sustained releasability and the hydrogen sulfide sustained release agent mean a capability that hydrogen sulfide is detected in a concentration of 1/100 or more of the maximum value thereof continuously for 30 minutes or more in the $H_2S$ release experiment described later, and a substance having the capability, respectively. For example, in the result of the $H_2S$ release experiment shown in FIG. 5, the maximum value of the $H_2S$ concentration detected is approximately 35 ppm, and therefore it can be judged that the hydrogen sulfide sustained releasability is achieved in the case where 0.35 ppm, which is 1/100 thereof, or more of $H_2S$ is detected continuously for 30 minutes or more.

The $H_2S$ release experiment is performed in the following manner.

A gas inlet tube and a gas outlet tube are inserted into a sealed vessel housing the sulfide ion-containing LDH, air at 20° C. and 50% RH is introduced from the gas inlet tube at a flow rate of 100 mL/min, the $H_2S$ concentration in air came out from the outlet tube is measured with a $H_2S$ sensor every 1 minute, and the time course change of the $H_2S$ concentration is measured. The measurement interval may be changed within a range of 1 minute to 5 minutes depending on the sustained release time.

The $H_2S$ sensor used for measuring the concentration is ToxiRAE 3, produced by RAE Systems, Inc., (detection limit: 0.4 ppm, resolution: 0.1 ppm), and equivalent products may also be used. Other concentration measuring methods, such as a detector tube and gas chromatography, may also be used instead of the $H_2S$ sensor. For example, in the case where a detector tube (produced by Gastec Corporation) is used, the discharged gas collected within a prescribed period of time of 1 to 5 minutes with a Tedlar (registered trade mark) bag or the like is measured by the detector tube method.

The total amount of hydrogen sulfide released from the hydrogen sulfide sustained release agent is approximately proportional to the proportion of $HS^-$ and/or $S_k^{2-}$ occupied in the anion sites among the layers (i.e., the value of y in the formula (1)) in the sulfide ion-containing LDH. The proportion can be controlled by changing the ratio of the molar number of $HS^-$ and/or $S_k^{2-}$ in the solution to be brought into contact with the raw material LDH or the easily anion exchangeable LDH used in the production of the sulfide ion-containing LDH to the molar number of the raw material LDH or the easily anion exchangeable LDH. In the case where the proportion or the ratio is small, a part of the anion component contained in the raw material LDH or the easily anion exchangeable LDH remains between the layers of the sulfide ion-containing LDH.

The hydrogen sulfide sustained release agent according to the present embodiment contains the sulfide ion-containing LDH as an essential component as described above, and may further contain, to the extent that the object of the invention can be achieved, various additives, such as a component controlling the sustained release rate of hydrogen sulfide, a diluent or an extender, a surface coating agent, and a component generating another compound through reaction with hydrogen sulfide, and a physical processing therefor, such as wrapping with a cover tape having restricted aeration, may be applied.

While hydrogen sulfide can be sustainably released by the material and the method described above, such a situation is likely assumed that the release with a narrower concentration range for a further prolonged period of time is demanded in the medical application from the standpoint of the safety, the concentration control, and the constancy in concentration. Accordingly, a higher standard of the sustained releasability is necessarily assumed than the "capability that hydrogen sulfide is detected in a concentration of $\frac{1}{100}$ or more of the maximum value thereof continuously for 30 minutes or more in the $H_2S$ release experiment" as the standard of the hydrogen sulfide sustained releasability described above. Examples thereof include a severer standard in both concentration and time, such as a "capability that hydrogen sulfide is detected in a concentration of $\frac{1}{2}$ or more of the maximum value thereof continuously for 2 hours or more in the $H_2S$ release experiment" (which may be hereinafter referred to as a "higher hydrogen sulfide sustained releasability").

In the case where the "higher hydrogen sulfide sustained releasability" is targeted, it is considered that the sulfide ion-containing LDH is further processed or treated. The present inventors have developed processes and treatments that further enhance the hydrogen sulfide sustained releasability, which are described below as preferred embodiments. In the description herein, the processes and treatments that further enhance the hydrogen sulfide sustained releasability of the sulfide ion-containing LDH are generically referred to as a "sustained release enhancement treatment".

[Process of Forming Sulfide Ion-Containing LDH into Granulated Material or Powder Compact Material]

Examples of the sustained release enhancement treatment as a preferred embodiment of the present invention include a process of forming the sulfide ion-containing LDH in the form of powder into a granulated material or a powder compact material through a densification treatment. According to the process, the surface area per mass of the sulfide ion-containing LDH is decreased, whereby the contact with carbon dioxide and water, which is a factor of hydrogen sulfide release, is suppressed, and simultaneously hydrogen sulfide released is suppressed from being diffused to the atmosphere, resulting in the enhancement of the sustained releasability.

The method for the densification treatment is not particularly limited, and examples thereof include a granulation method, such as tumbling granulation and spray drying, a press molding method, such as uniaxial press molding, and a method of press densification in housing in the packaging material.

From the standpoint of the enhancement of the sustained releasability through the decrease of the surface area per mass of the sulfide ion-containing LDH, the simple increase of the accumulation thickness of the sulfide ion-containing LDH is also effective.

[Mixing of Sulfide Ion-Containing LDH with Extender]

Examples of the sustained release enhancement treatment as another preferred embodiment of the present invention include a process of mixing of the sulfide ion-containing LDH with an extender or a diluent. According to the process, the amount of the sulfide ion-containing LDH is decreased, and the contact with carbon dioxide and water, which is a factor of hydrogen sulfide release, is suppressed by the extender or the diluent, whereby the peak concentration of $H_2S$ released can be suppressed, which consequently leads to the enhancement of the sustained releasability.

The usable extender or diluent is not particularly limited, as far as it does not release hydrogen sulfide and does not react therewith, and examples thereof include an inorganic material, such as silica, alumina, a layered double hydroxide, and glass, and an organic material, such as oil and fat, and a resin. Jelly, gel, cream, and the like may also be used as the extender or the diluent.

[Housing Sulfide Ion-Containing LDH in Porous Cover or Container]

Examples of the sustained release enhancement treatment as still another preferred embodiment of the present invention include a process of housing the sulfide ion-containing LDH in a porous cover or container. According to the process, the contact of the sulfide ion-containing LDH with carbon dioxide and water, which is a factor of hydrogen sulfide release, is suppressed, and simultaneously hydrogen sulfide released from the sulfide ion-containing LDH is suppressed from being diffused to the atmosphere, resulting in the enhancement of the sustained releasability.

Figure 4:
FIG. 4 is a schematic illustration showing an example of the structure of a hydrogen sulfide sustained release composite constituted by the sulfide ion-containing LDH held with a membrane filter and a porous tape.

The material, the shape, the porosity, the pore size, and the like of the porous cover or container for housing the sulfide ion-containing LDH are not limited, and may be appropriately selected depending on the purpose. Examples thereof include a container including an assembly of membrane filters holding the sulfide ion-containing LDH, and porous tapes holding the assembly, as shown in FIG. 4. The porous tape used may be a commercially available surgical tape.

[Treatment of Changing Distribution State of Sulfur-Containing Anion in Sulfide Ion-Containing LDH]

Examples of the sustained release enhancement treatment as still another preferred embodiment of the present invention include a treatment of changing the distribution state of $HS^-$ and/or $S_k^{2-}$ (wherein k represents a positive integer) as the sulfur-containing anion in the sulfide ion-containing LDH. Examples of the treatment include a water washing treatment, a contact treatment with oxygen, a homogenization treatment of the compositional distribution, and a hydrogen sulfide release treatment. These examples are described below.

<Water Washing Treatment of Sulfide Ion-Containing LDH]

The water washing treatment of the sulfide ion-containing LDH is a treatment of washing the sulfide ion-containing LDH with a liquid containing water. Specific examples thereof include the washing operation after the synthesis of the sulfide ion-containing LDH that is performed with a water solvent, and the addition of a water washing operation to the washing operation with a solvent other than a water solvent. By this treatment, the release of a large amount of hydrogen sulfide immediately after the contact of the sulfide ion-containing LDH with the air atmosphere (i.e., the initial high concentration release) can be prevented, and the maximum release concentration of hydrogen sulfide can be suppressed. Furthermore, the release can be retained for a prolonged period of time. As a result, these factors lead to the enhancement of the sustained releasability.

The mechanism therefor is considered as follows. In the sulfide ion-containing LDH immediately after the production, the hydrogen sulfide source is attached to the surface of the particles, the hydrogen sulfide source is retained in the voids among the particles, and $HS^-$ and/or $S_k^{2-}$ are intercalated among the layers in the vicinity of the surface of the particles. In the case where the sulfide ion-containing LDH in this state is brought into contact with the air atmosphere, hydrogen sulfide is simultaneously generated from these hydrogen sulfide sources, and thus a large amount of hydrogen sulfide is released. However, with the water washing in advance, the hydrogen sulfide sources are removed, and thus the amount of hydrogen sulfide generated immediately after the contact of the sulfide ion-containing LDH with the air atmosphere is suppressed. Accordingly, with more elaborate water washing of the sulfide ion-containing LDH performed, i.e., with an increased number of times of water washing or an increased period of time therefor, the amount of hydrogen sulfide generated immediately after the contact with the air atmosphere is suppressed.

The liquid used for washing is not limited, as far as it contains water, and water itself is preferred from the standpoint of the efficient removal of the hydrogen sulfide source. Water used is preferably distilled water or ion exchanged water from the standpoint of the prevention of contamination with impurities. Water having decreased contents of gases dissolved therein, such as oxygen and carbon dioxide, is more preferred from the standpoint of the control, suppression, or prevention of the generation of hydrogen sulfide and the oxidation of the sulfide source during washing. Examples of the method of decreasing the dissolved gas in water include bubbling with nitrogen gas, a rare gas, or the like.

The method of washing is also not particularly limited, and examples thereof include a method of repeating dispersion and solid-liquid separation of sulfide ion-containing LDH in water, and a method of supplying flowing water to the sulfide ion-containing LDH on a filter. A common operation such as filtration and centrifugal separation can be used as the above-mentioned solid-liquid separation method.

<Contact Treatment of Sulfide Ion-Containing LDH with Oxygen>

The contact treatment of the sulfide ion-containing LDH with oxygen literally means a treatment of bringing the sulfide ion-containing LDH into contact with oxygen. According to the treatment, the hydrogen sulfide source attached to the surface of the particles, the hydrogen sulfide source retained in the voids among the particles, and $HS^-$ and/or $S_k^{2-}$ intercalated among the layers in the vicinity of the surface of the particles can be deactivated through oxidation, resulting in the similar effect as the water washing treatment.

The contact method of the sulfide ion-containing LDH with oxygen is not particularly limited, and examples thereof used include a method of introducing an oxygen-containing gas into a vessel housing the sulfide ion-containing LDH. The content of oxygen and other gas components of the oxygen-containing gas used herein is not limited, as far as it contains oxygen, and a gas that does not contain water and carbon dioxide or has decreased contents thereof is preferred from the standpoint of the suppression of the generation of hydrogen sulfide during the treatment.

<Homogenization Treatment of Compositional Distribution of Sulfide Ion-Containing LDH>

The homogenization treatment of the compositional distribution of the sulfide ion-containing LDH means a treatment of reducing the heterogeneity of the distribution of the hydrogen sulfide source in the sulfide ion-containing LDH, and specific examples thereof include prolongation of the storing time in storing the sulfide ion-containing LDH in a volume reduction state, vacuum, or an inert gas atmosphere, heating the sulfide ion-containing LDH, and a combination thereof.

The mechanism that the hydrogen sulfide release concentration is decreased, and the release is retained for a prolonged period of time through the homogenization treatment of the compositional distribution of the sulfide ion-containing LDH is considered as follows. The sulfide ion-containing LDH immediately after the production has fluctuation in distribution of $HS^-$ and/or $S_k^{2-}$ among the layers due to the heterogeneity of the ion exchange and the like. In particular, there occurs a state where a large amount of $HS^-$ and/or $S_k^{2-}$ is contained among the layers in the vicinity of the surface, whereas the ions are substantially not contained among the layers in the interior remote from the surface. In the case where the sulfide ion-containing LDH in this state is bought into contact with the air atmosphere, most of $HS^-$ and/or $S_k^{2-}$ among the layers that can be released as hydrogen sulfide is released within a short period of time after the contact. However, with the homogenization of the compositional distribution, $HS^-$ and/or $S_k^{2-}$ in the vicinity of the surface is diffused to the interior to reduce the heterogeneity in distribution, and thus in contact with the air atmosphere, $HS^-$ and/or $S_k^{2-}$ in the interior is released late. Accordingly, the initial high concentration release of hydrogen sulfide can be prevented to suppress the maximum release concentration of hydrogen sulfide. Furthermore, the release can be retained for a prolonged period of time. As a result, these factors lead to the enhancement of the sustained releasability.

The period of time and the temperature of the homogenization treatment of the compositional distribution are not particularly limited, and examples thereof include storing at room temperature for approximately 4 weeks to 6 months. In the case where the homogenization of the compositional distribution is achieved by heating, the effect can be obtained within a shorter period of time. For example, the effect may appear within few days in heating to 40° C. or within approximately one day in heating to 60° C. The heating temperature in this case is preferably 100° C. or less, and more preferably 80° C. or less, from the standpoint of the prevention of the release of hydrogen sulfide and interlayer water from the sulfide ion-containing LDH.

The homogenization treatment of the compositional distribution may be performed before hermetically housing the sulfide ion-containing LDH in the packaging material or after hermetically housing in the packaging material.

<Hydrogen Sulfide Release Treatment of Sulfide Ion-Containing LDH>

The hydrogen sulfide release treatment of the sulfide ion-containing LDH is a treatment of releasing a part of hydrogen sulfide contained in the sulfide ion-containing LDH therefrom. According to the treatment, the initial high concentration release of a large amount of hydrogen sulfide immediately after the contact of the sulfide ion-containing LDH with the air atmosphere can be prevented, and the maximum release concentration of hydrogen sulfide can be suppressed. Furthermore, the feature that the release is retained for a prolonged period of time is not impaired.

The mechanism thereof is considered as follows. In the sulfide ion-containing LDH immediately after the production, the hydrogen sulfide source is attached to the surface of the particles, the hydrogen sulfide source is retained in the voids among the particles, and $HS^-$ and/or $S_k^{2-}$ are intercalated among the layers in the vicinity of the surface of the particles. In the case where the sulfide ion-containing LDH in this state is brought into contact with the air atmosphere, hydrogen sulfide is simultaneously generated from these hydrogen sulfide sources, and thus a large amount of hydrogen sulfide is released. However, with the hydrogen sulfide release treatment performed in advance, hydrogen sulfide derived from above-mentioned hydrogen sulfide sources is released to remove the hydrogen sulfide sources, and thus the amount of hydrogen sulfide generated immediately after the contact of the sulfide ion-containing LDH with the air atmosphere is suppressed.

The method of releasing hydrogen sulfide from the sulfide ion-containing LDH is not particularly limited, and examples thereof used include a method of placing the sulfide ion-containing LDH in an atmosphere containing water and carbon dioxide, and aeration, in which air is introduced into a vessel housing the same.

The preferred embodiments of the present invention where the sustained release enhancement treatment is preformed may be used alone, or a combination of two or more of the embodiments may be used. An appropriate combination of two or more of the embodiments is preferred from the standpoint of the achievement of the higher hydrogen sulfide sustained releasability since the combination can further enhance the sustained releasability as compared to the single use of the embodiments. Accordingly, the optimum hydrogen sulfide sustained releasability corresponding to the purpose can be obtained.

It is considered that the sustained release enhancement treatment described above is effective not only for the sulfide ion-containing LDH, but also for other solid materials that contain a hydrogen sulfide source and release hydrogen sulfide through reaction with the air atmosphere.

EXAMPLES

The present invention will be described specifically with reference to examples below. However, the examples are shown for contributing to understanding of the present invention, and do not limit the present invention.

Examples 1 to 3 are production examples of the sulfide ion-containing LDH and the package hermetically housing the same, using the ion exchange method through a Cl type LDH as the easily anion exchangeable LDH.

Example 1

As the carbonate type LDH, a commercially available carbonate type layered double hydroxide having a Mg ion as a divalent metal ion and an Al ion as a trivalent metal ion represented by the general formula $Mg_3Al(OH)_8(CO_3^{2-})_{0.5}\cdot2H_2O$ (DHT-6, produced by Kyowa Chemical Industry Co., Ltd., particle diameter distribution: approximately 0.1 to 1 μm, Mg/Al molar ratio: 2.99 (±0.06)) was used. This LDH is hereinafter referred to as $CO_3^{2-}$ Firstly, the carbonate type LDH was converted to the Cl type LDH according to the method described in Japanese Patent No. 5,867,831.

250 mg of the $CO_3^{2-}$-MgAl-LDH3 was weighed and placed in a three-neck flask, to which 37.5 mL of ethanol was added. Under a nitrogen flow (500 mL/min), while stirring the suspension liquid with a magnetic stirrer, 12.5 mL of a hydrochloric acid ethanol solution (0.1 mol/L) was added dropwise thereto, and the mixture was reacted at room temperature (20 to 25° C.) for 1 hour under stirring. Thereafter, under a nitrogen flow, the mixture was filtered with a membrane filter having a pore diameter of 0.2 μm, and the precipitate was sufficiently washed with ethanol. The precipitate thus filtered was collected and recovered, immediately decompressed, and dried in vacuum for 1 hour or more, so as to provide white powder.

The FTIR measurement (Fourier transform infrared spectroscopy, Perkin-Elmer Spectrum One, ATR Attachment) of the resulting white powder revealed that there was no absorption at 1,360 $cm^{-1}$ of a carbonate ion (C0), and thus it was judged that the carbonate ion was substituted by the chloride ion. The ICP-AES analysis (SPS 1700HVR, produced by Seiko Instruments, Inc.) thereof revealed that the Mg/Al ratio was not changed. This LDH is hereinafter referred to as $Cl^-$MgAl-LDH3.

Subsequently, a sulfide ion-containing LDH was produced from the $Cl^-$MgAl-LDH3.

In a globe box with a nitrogen atmosphere, 7 mg of $NaHS\cdot nH_2O$ (sodium hydrosulfide n-hydrate, 65% in terms of anhydrate, produced by Wako Pure Chemical Industries, Ltd.) was dissolved in 15 mL of degassed ion exchanged water to prepare a NaHS solution. In all the examples shown below, the same material as in this example was used as $NaHS\cdot nH_2O$. The degassed ion exchanged water was obtained in such a manner that ion exchanged water was boiled and then cooled, during which nitrogen gas was bubbled, and in all the examples shown below, degassed ion exchanged water obtained in the same manner was used.

25 mg of the $Cl^-$MgAl-LDH3 was weighed and placed in a 30 mL glass vial, to which the NaHS solution was added, and the mixture was dispersed by sufficiently shaking, in the globe box.

The reaction was performed for 2 days in the glass vial hermetically sealed, and then in the globe box, the mixture was filtered with a membrane filter having a pore diameter of 0.2 μm, and the filtered matter (residue) was washed with degassed ion exchanged water, decompressed along with the membrane filter, and dried in vacuum for approximately 30 minutes, so as to provide a pale yellow powder specimen (sulfide ion-containing LDH).

Subsequently, a package hermetically housing the sulfide ion-containing LDH was produced.

In the globe box, the resulting pale yellow powder specimen was placed in a 13.5 mL glass container (packaging material) along with the membrane filter, and the container was hermetically sealed to provide a package.

The sulfide ion-containing LDH in the resulting package was subjected to the $H_2S$ release experiment in the manner described above.

Figure 5:
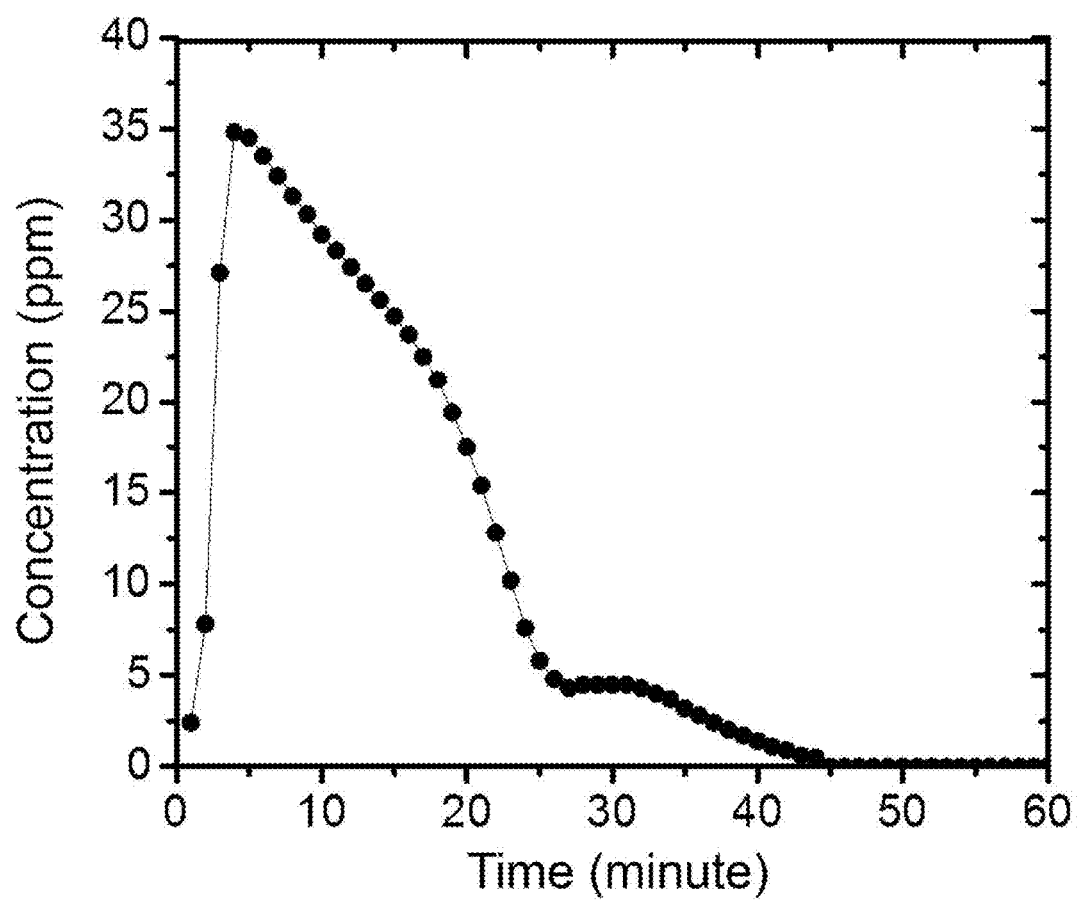
FIG. 5 is a graph showing the time course change of the concentration of $H_2S$ released from the sulfide ion-containing LDH in Example 1.

FIG. 5 shows the time course change of the concentration of $H_2S$. After the contact with air, the $H_2S$ concentration was gradually increased and showed the maximum value after several minutes, and then the concentration was gradually decreased. The period of time where $H_2S$ was detected was approximately 40 minutes after the detection of the maximum value, from which it was found that the sulfide ion-containing LDH obtained in this example had hydrogen sulfide sustained releasability.

Example 2

As the carbonate type LDH, an LDH (MgAl-LDH2) having a Mg ion as a divalent metal ion and an Al ion as a trivalent metal ion represented by the general formula $Mg_2Al(OH)_6(CO_3^{2-})_{0.5} \cdot 2H_2O$ was synthesized and used. This LDH is hereinafter referred to as $CO_3^{2-}$-MgAl-LDH2. The $CO_3^{2-}$-MgAl-LDH2 had a Mg/Al molar ratio of approximately 2, and a smaller Mg/Al ratio than the $CO_3^{2-}$-MgAl-LDH3 used in Example 1. This means that the layer charge density is large.

Firstly, the $CO_3^{2-}$-MgAl-LDH2 was synthesized according to the method described in JP-A-2005-335965.

$MgCl_2 \cdot 6H_2O$ (508 mg) and $AlCl_3 \cdot 6H_2O$ (302 mg) were weighed, to which 12.5 mL of ion exchanged water was added to form a solution, and 12.5 mL of an aqueous solution obtained by dissolving hexamethylenetetramine (613 mg) was added and mixed therewith to prepare a solution, which was filtered with a 0.2 micron membrane filter, then placed in a pressure tight Teflon (registered trade mark) vessel having a capacity of 50 mL, which was housed and sealed in a pressure tight stainless steel vessel, and subjected to a hydrothermal treatment at 140° C. for 1 day. The mixture after the hydrothermal treatment was filtered, washed with water, and dried in vacuum, so as to provide 279 mg of white powder.

Figure 6:
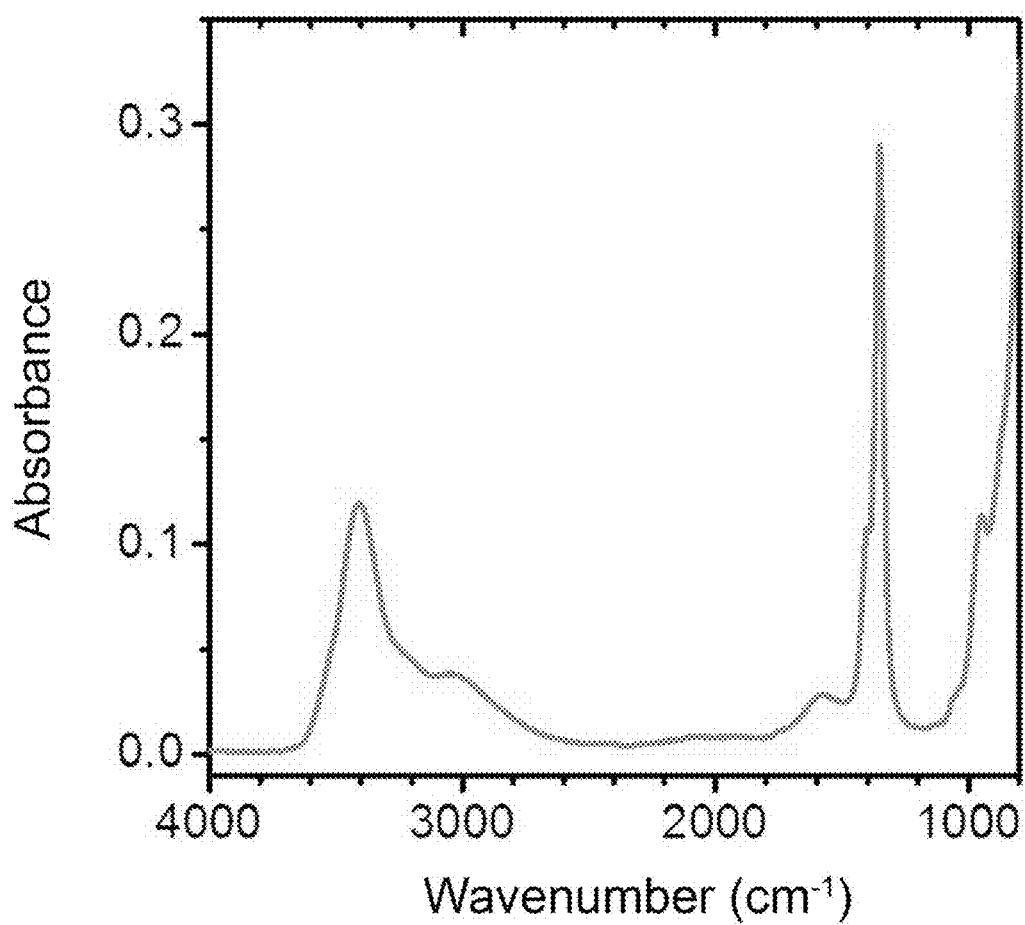
FIG. 6 is a graph showing the Fourier transform infrared spectroscopy (FTIR) of the synthesized carbonate type LDH ($CO_3^{2-}$ MgAl-LDH2) in Example 2.

The resulting white powder had a particle diameter of approximately 0.5 to 2 μm and a Mg/Al molar ratio of 1.94 (±0.04). As shown in FIG. 6, the FTIR (Fourier transform infrared spectroscopy) absorption spectrum agreed with the reported profile.

Subsequently, the resulting carbonate type LDH ($CO_3^{2-}$-MgAl-LDH2) was converted to the Cl type LDH.

80.7 mg of the $CO_3^{2-}$-MgAl-LDH2 was weighed and placed in a three-neck flask, to which 43.3 mL of ethanol was added to prepare a suspension liquid. Under a nitrogen flow (500 mL/min), while stirring the suspension liquid with a magnetic stirrer, 6.7 mL of a hydrochloric acid ethanol solution (0.1 mol/L) was added dropwise thereto, and the mixture was reacted at 35° C. for 1 hour under stirring. The filtration, washing, and drying treatment was performed under the same condition as applied to the drying of the Cl type LDH in Example 1, so as to provide white powder.

Figure 7:
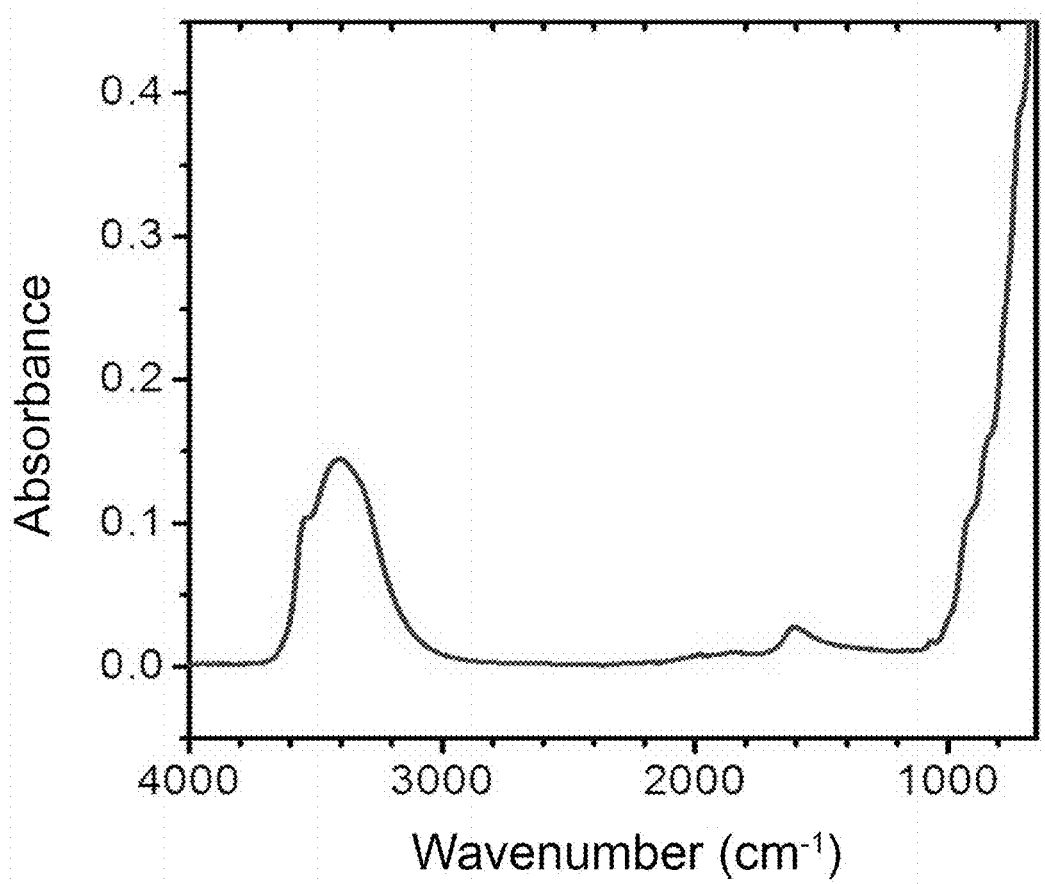
FIG. 7 is a graph showing the Fourier transform infrared spectroscopy (FTIR) of the product obtained through reaction of the carbonate type LDH ($CO_3^{2-}$ MgAl-LDH2) with a hydrochloric acid ethanol solution in Example 2.

The FTIR measurement (Fourier transform infrared spectroscopy) of the resulting white powder revealed that there was no absorption at 1,360 $cm^{-1}$ of a carbonate ion ($CO_3^{2-}$) as shown in FIG. 7, and thus it was judged that the carbonate ion was substituted by the chloride ion. The ICP-AES analysis (SPS 1700HVR, produced by Seiko Instruments, Inc.) thereof revealed that the Mg/Al ratio was not changed. This LDH is hereinafter referred to as $Cl^-$-MgAl-LDH2.

Subsequently, a sulfide ion-containing LDH was produced from the $Cl^-$-MgAl-LDH2.

In a globe box with a nitrogen atmosphere, methanol was degassed through nitrogen gas bubbling, then 780 mg of $Na_2S \cdot 9H_2O$ (sodium sulfide nonahydrate, guaranteed reagent, produced by Wako Pure Chemical Industries, Ltd.) was dissolved in 25 mL of the methanol to prepare a $Na_2S$ solution. In all the examples shown below, the same material as in this example was used as $Na_2S \cdot 9H_2O$.

40.5 mg of the $Cl^-$-MgAl-LDH2 was weighed and placed in a 30 mL glass vial, to which the $Na_2S$ solution was added, and the mixture was dispersed by sufficiently shaking, in the globe box.

The reaction was performed for 2 days in the glass vial hermetically sealed, and then in the globe box, the mixture was filtered with a membrane filter having a pore diameter of 0.2 μm, and the filtered matter (residue) was washed with degassed methanol, decompressed along with the membrane filter, and dried in vacuum for approximately 30 minutes, so as to provide a white powder specimen (sulfide ion-containing LDH).

Subsequently, a package hermetically housing the sulfide ion-containing LDH was produced.

In the globe box, the resulting sulfide ion-containing LDH was placed in a 13.5 mL glass container (packaging material) along with the membrane filter, and the container was hermetically sealed to provide a package.

The sulfide ion-containing LDH in the resulting package was subjected to the $H_2S$ release experiment in the same manner as in Example 1.

Figure 8:
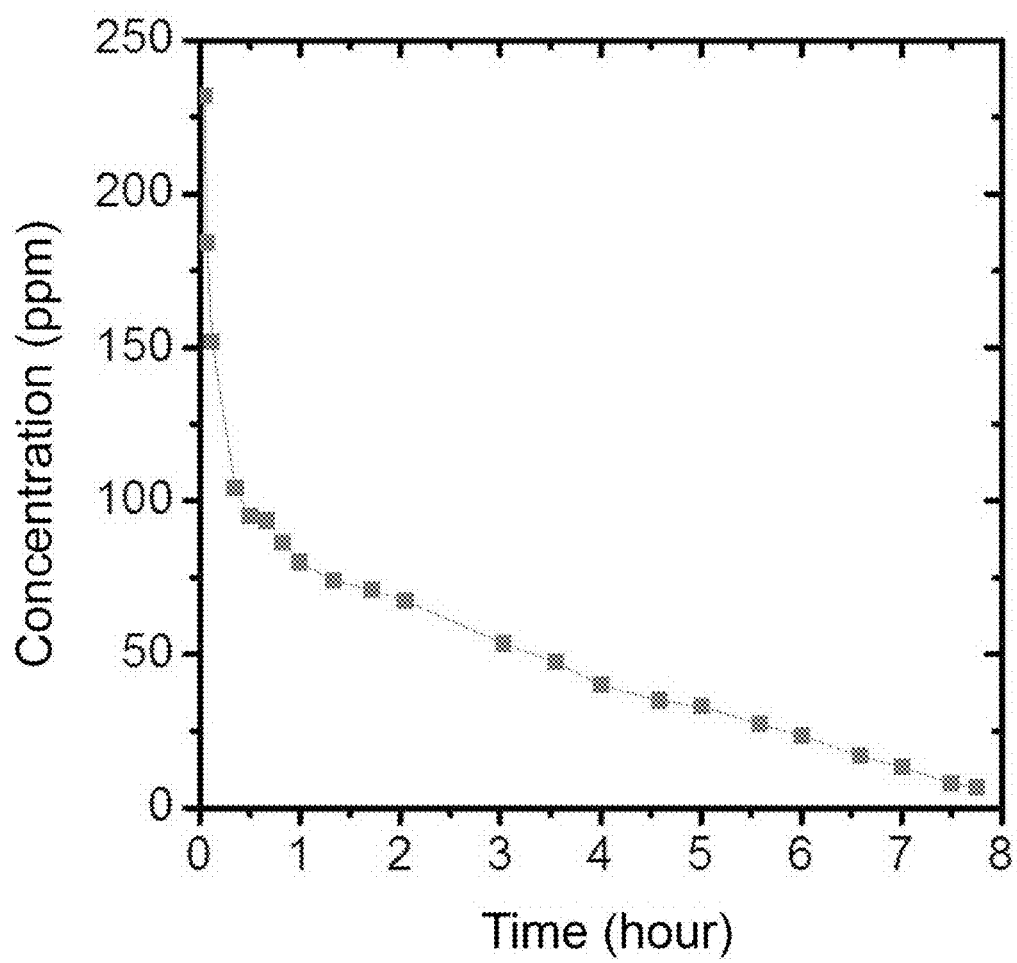
FIG. 8 is a graph showing the time course change of the concentration of $H_2S$ released from the sulfide ion-containing LDH in Example 2.

FIG. 8 shows the time course change of the concentration of $H_2S$. After the contact with air, the concentration was immediately increased and showed the maximum value, and then the concentration was gradually decreased. The total amount of $H_2S$ released was 0.103 mmoL. The period of time where $H_2S$ was detected was approximately 8 hours after the detection of the maximum value, from which it was found that the sulfide ion-containing LDH obtained in this example had hydrogen sulfide sustained releasability.

The sulfide ion-containing LDH after the $H_2S$ release experiment was subjected to the FTIR (ATR method) measurement.

Figure 9:
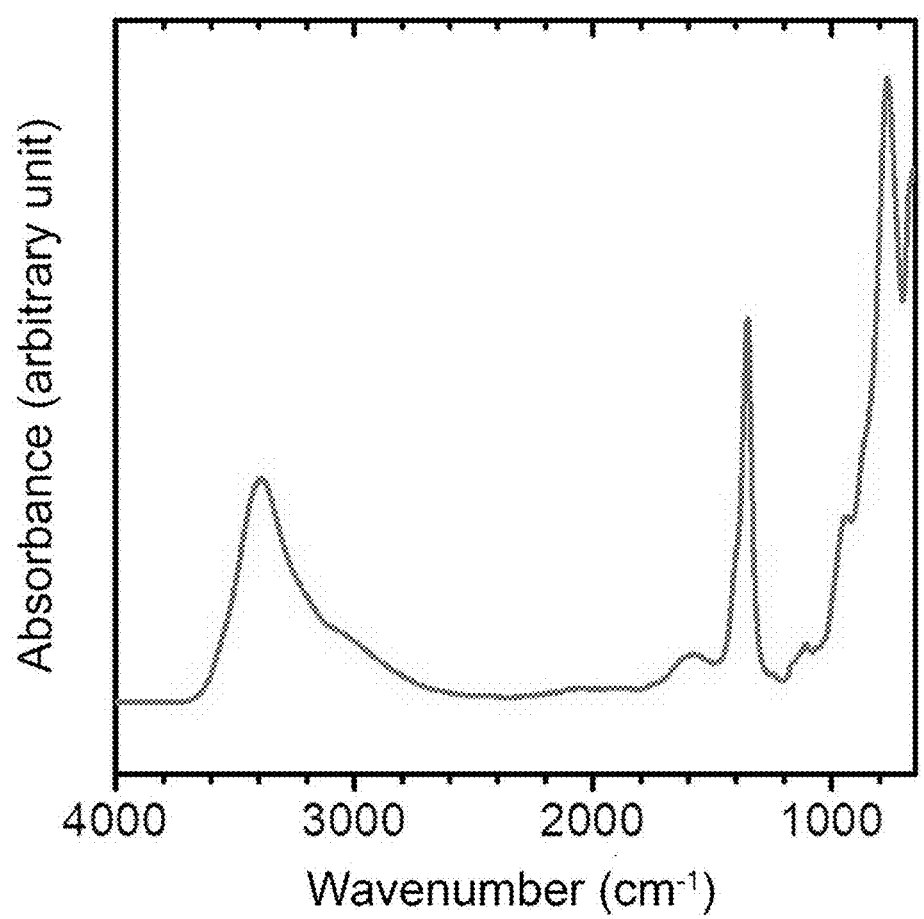
FIG. 9 is a graph showing the Fourier transform infrared spectroscopy (FTIR) of the sulfide ion-containing LDH after releasing $H_2S$ in Example 2.

FIG. 9 shows the resulting infrared absorption profile. In the measured specimen, the absorption of a carbonate ion ($CO_3^{2-}$) at 1,360 $cm^{-1}$, which was not observed in the $Cl^-$-MgAl-LDH2, significantly appeared. Substantially no absorption was observed around 1,000 $cm^{-1}$.

It was estimated from the result that the sulfur-containing anion in the sulfide ion-containing LDH was released as $H_2S$ to the air atmosphere through substitution with $CO_3^{2-}$, but was not oxidized to form a thiosulfate ion or a sulfate ion. A sulfide ion was not able to be observed by FTIR due to the absence of an intense characteristic peak in the infrared region, and therefore the specimen after the release of $H_2S$ was subjected to thermal analysis for determining the presence of the residual sulfur component.

The sulfide ion-containing LDH after the $H_2S$ release experiment was subjected to thermal analysis with TG-DTA (ThermoPlus TG8120, produced by Rigaku Corporation). The measurement condition was a temperature increase rate of 10° C./min, a heating temperature of 1,100° C., and an air flow (20 mL/min).

Figure 10:
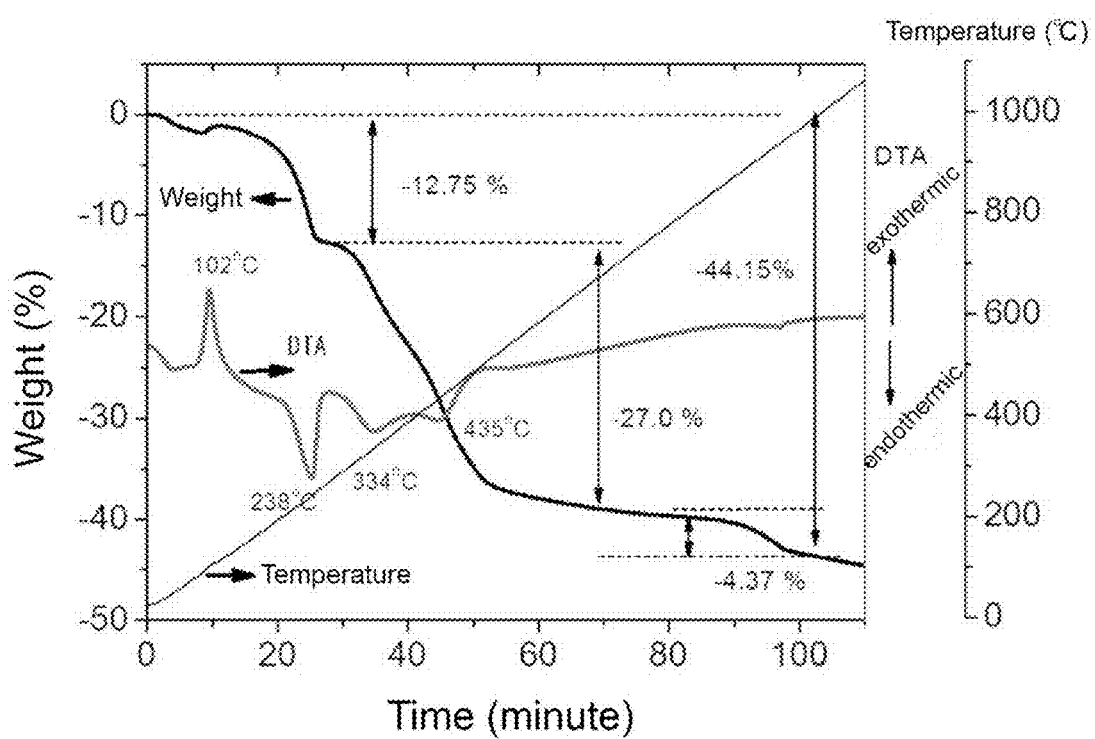
FIG. 10 is a graph showing the result of the thermal analysis (TG-DTA) of the sulfide ion-containing LDH after releasing $H_2S$ in Example 2.

FIG. 10 shows the measurement result. Heat generation and weight increase were observed at 100° C., and weight decrease was observed at 800 to 1,000° C. It can be understood that the heat generation and weight increase at 100° C. correspond to the phenomenon that the residual S component is oxidized to form a sulfate ion or a thiosulfate ion, and the weight decrease at 800 to 1,000° C. corresponds to the phenomenon that the sulfate ion or a sulfate ion formed through oxidation of the thiosulfate ion around 600° C. is desorbed as $SO_3$.

The presence of the residual S component suggests that molecular species of S that do not involve in the release of $H_2S$ exist among the layers after the release of $H_2S$. The molecular species are considered to form a polysulfide of S having a low valence.

The general formula of the sulfide ion-containing LDH in this example was determined in the following method. This method shows the simplest example, in which $CO_3^{2-}$ does not remain in the easily anion exchangeable LDH, such as the $Cl^-$ LDH, as the starting material, the anion site of the sulfide ion-containing LDH after the production does not have a residual anion, such as $Cl^-$, and the sulfur-containing anion among the layers entirely exists as $HS^-$. In the case where the residual anion exists in the anion site, the amount thereof is measured, and the general formula is determined with the amount incorporated thereto.

Firstly, the LDH used was subjected to analysis with ICP-AES (ICP atomic emission spectroscopy) in advance to measure the cation amount of the sulfide ion-containing LDH, and the molar ratios of Q (divalent metal ion) and R (trivalent metal ion) in the formula were calculated from the analysis value, and the value of x in the general formula (1) was determined as x=2.

Subsequently, for the sulfide ion-containing LDH in a known mass, the $H_2S$ concentration measured in the $H_2S$ release experiment was plotted against the time, so as to provide a $H_2S$ release curve. The release curve was integrated to calculate the total molar number of $H_2S$ released from the sulfide ion-containing LDH, so as to provide $(HS^-)_{0.64}$.

Subsequently, a part of the sulfide ion-containing LDH after the $H_2S$ release experiment, from which no release of $H_2S$ was observed, was subjected to thermal analysis with TG-DTA (thermogravimetric-differential thermal analyzer). The measurement condition was a temperature increase rate of 10° C./min, a heating temperature of 1,100° C., and an air flow (20 mL/min). In the resulting measurement result, the weight decrease at 100° C. to 250° C. was assumed to be derived from the desorption of $H_2O$ among the layers, the weight decrease at 300° C. to 600° C. was assumed to be derived from two factors, i.e., the desorption of $CO_3^{2-}$ among the layers as $CO_2$ and the desorption of an OH group constituting the layers as $H_2O$, and the weight decrease at 700° C. to 1,100° C. was assumed to be derived from desorption of a sulfate ion ($SO_4^{2-}$) as $SO_3$. Since the product at 1,100° C. was a mixture of metal oxides derived from the metal ions of the layers, the molecular weights (chemical formula weights) in each stage were obtained through back calculation from the molecular weight (chemical formula weight) of the product, and the amounts of $H_2O$, $CO_3^{2-}$, and the residual sulfide anion ($HS^-$) contained in the sulfide ion-containing LDH complex after the $H_2S$ release experiment were calculated. Specifically, the proportions of $HS^-$ and/or $S_k^{2-}$ and $CO_3^{2-}$ in the anion site of the sulfide ion-containing LDH after the $H_2S$ release experiment were obtained to provide $\{(HS^-)_{0.13}(CO_3)_{0.35}\}$, and the value of n in the general formula (1) was determined as n=1.8 from the $H_2O$ amount. For the proportion of $CO_3^{2-}$, the mass of the OH group constituting the layers along with the cation was calculated by 2(x+1) based on the value of x above, and the mass is subtracted from the weight decrease at 300° C. to 600° C. obtained in the thermal analysis to calculate the mass of $CO_2$ released within the temperature range, from which the proportion of $CO_3^{2-}$ was determined.

Based on the mass of the sulfide ion-containing LDH subjected to the $H_2S$ release experiment and the total molar number of $H_2S$ therein, and the amount of the residual sulfur-containing anion ($HS^-$) obtained in the thermal analysis, the value of y in the general formula (1) was determined as y=0.64+0.13=0.77.

Finally, assuming the premise that $CO_3^{2-}$ among the layers (anion site) in the specimen after the release experiment was constituted by one substituting $HS^-$ intercalated among the layer before the release experiment and one formed through reaction of $OH^-$ intercalated among the layers before the release experiment and $CO_2$ in air, two of $HS^-$ or $OH^-$ form one $CO_3^{2-}$ in the substitution or the reaction, and Z in the general formula (1) is $OH^-$, the value of t was determined from the molar number of $CO_3^{2-}$ existing among the layers of the specimen after the release experiment and the total molar number of $H_2S$ released therefrom, which were calculated by the method above, as t=0.35×2−0.64=0.06.

Accordingly, the general formula was obtained as $Mg_2Al(OH)_6\{(HS^-)_{0.77}(OH^-)_{0.06}\}\cdot 1.8H_2O$.

Example 3

As the $HS^-$ or $S_k^{2-}$ source to be mixed with the solvent in the production of the hydrogen sulfide sustained release agent from the easily anion exchangeable LDH, $Na_2S_3$ (produced by Dojindo Laboratories Co., Ltd.), a polysulfide, was used.

Firstly, the Cl⁻MgAl-LDH3 was prepared in the same manner as in Example 1.

Subsequently, a sulfide ion-containing LDH was produced from the Cl⁻MgAl-LDH3.

In a globe box with a nitrogen atmosphere, 100 mg of $Na_2S_3$ was dissolved in 7.5 mL of degassed methanol to prepare a $Na_2S_3$ solution.

10.8 mg of the Cl⁻MgAl-LDH3 was weighed and placed in a 30 mL glass vial, to which the $Na_2S_3$ solution was added, and the mixture was dispersed by sufficiently shaking, in the globe box.

The ion exchange reaction was performed for 2 days in the glass vial hermetically sealed, and then in the globe box, the mixture was filtered with a membrane filter having a pore diameter of 0.2 μm, and the filtered matter (residue) was washed with degassed methanol, decompressed along with the membrane filter, and dried in vacuum for approximately minutes, so as to provide an ocher powder specimen (sulfide ion-containing LDH).

Subsequently, a package hermetically housing the sulfide ion-containing LDH was produced.

In the globe box, the resulting sulfide ion-containing LDH was placed in a 13.5 mL glass container (packaging material) along with the membrane filter, and the container was hermetically sealed to provide a package.

Figure 11:
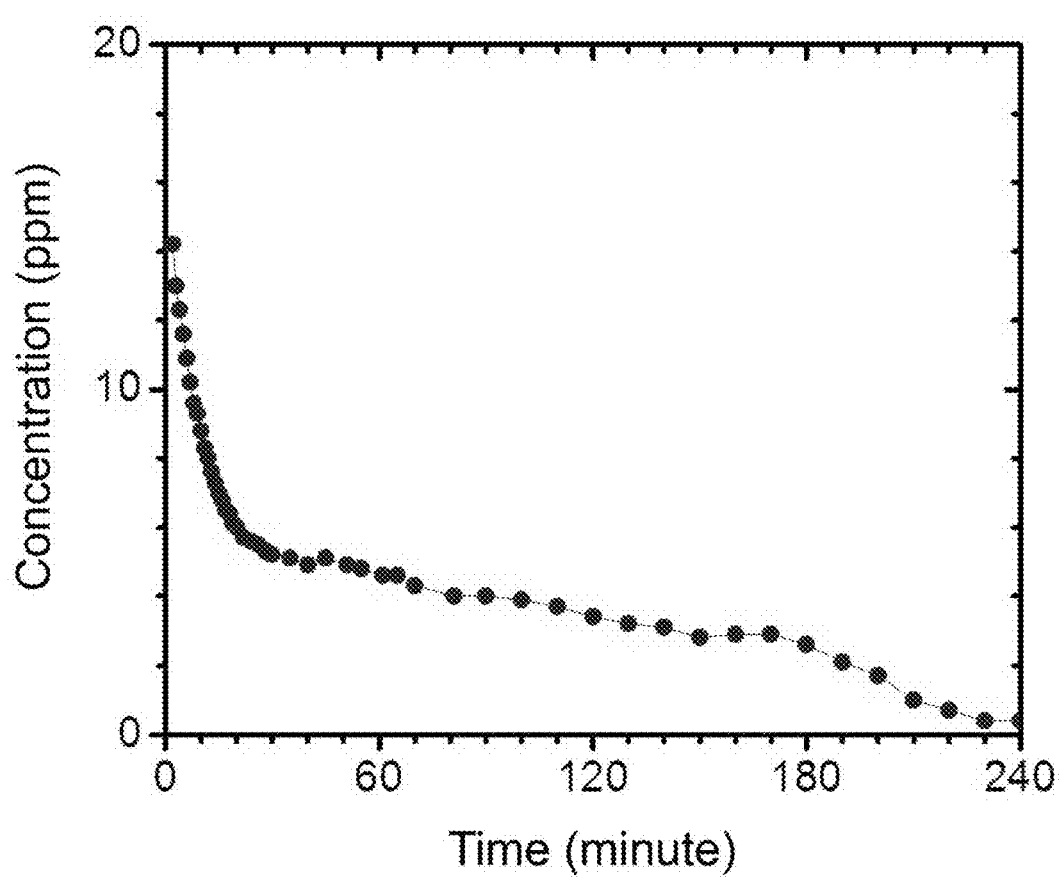
FIG. 11 is a graph showing the time course change of the concentration of $H_2S$ released from the sulfide ion-containing LDH in Example 3.

The sulfide ion-containing LDH in the resulting package was subjected to the $H_2S$ release experiment in the same manner as in Example 1. FIG. 11 shows the time course change of the concentration of $H_2S$. After the contact with air, the concentration was immediately increased and showed the maximum value, and then the concentration was gradually decreased. The period of time where $H_2S$ was detected was approximately 4 hours after the detection of the maximum value, from which it was found that the sulfide ion-containing LDH obtained in this example had hydrogen sulfide sustained releasability.

Figure 12:
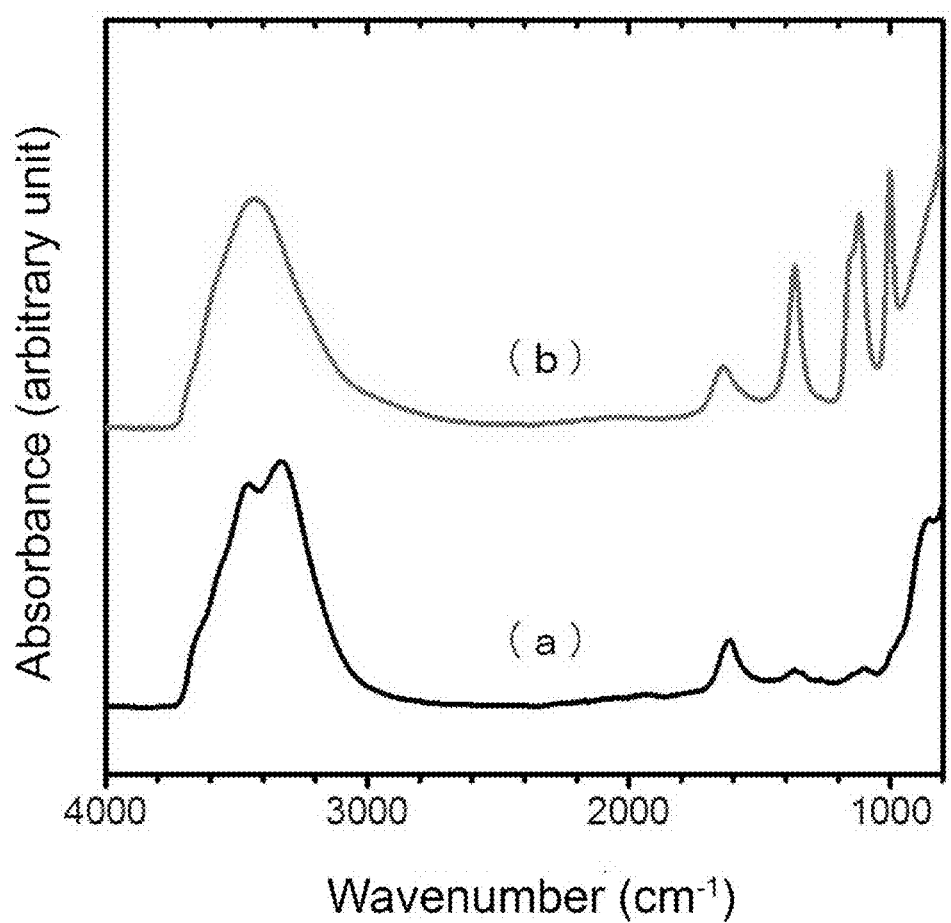
FIG. 12 is a graph showing the Fourier transform infrared spectroscopy (FTIR) of (a) the sulfide ion-containing LDH immediately after the production and (b) the sulfide ion-containing LDH subjected to the $H_2S$ release test for 2 hours, in Example 3.

The sulfide ion-containing LDH immediately after the production and the sulfide ion-containing LDH after subjected to the $H_2S$ release experiment for 2 hours were subjected to the FTIR (ATR method) measurement and compared to each other. FIG. 12 shows the result. In the sulfide ion-containing LDH immediately after the production (a), substantially no absorption of $CO_3^2$ and a thiosulfate ion was observed, but in the sulfide ion-containing LDH after subjecting to the $H_2S$ release experiment (b), absorption of a carbonate ion ($CO_3^{2-}$) at 1,360 cm⁻¹ and absorption of a thiosulfate ion at 1,000 to 1,100 cm⁻¹ significantly appeared, from which it was found that the sulfur-containing anion among the layers was substituted by $CO_3^{2-}$, and released as $H_2S$ to the air atmosphere, and the sulfur-containing anion remaining among the layers was oxidized with oxygen in the air atmosphere to form a thiosulfate ion.

Figure 13:
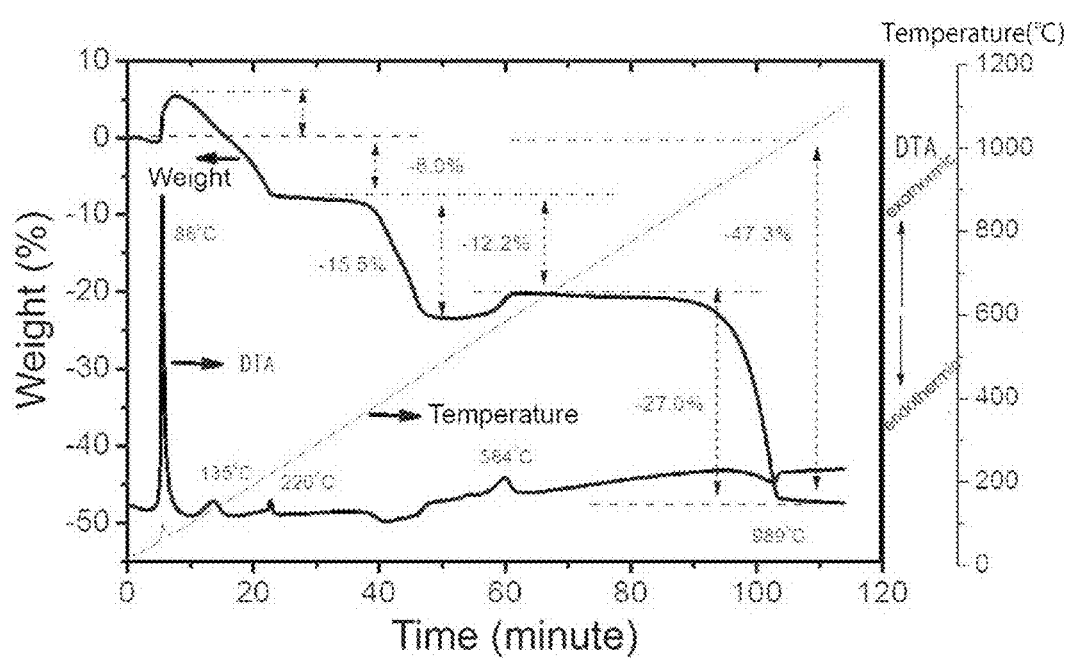
FIG. 13 is a graph showing the result of the thermal analysis (TG-DTA) of the sulfide ion-containing LDH immediately after the production in Example 3.

The sulfide ion-containing LDH immediately after the production, i.e., before the $H_2S$ release experiment, was subjected to thermal analysis with TG-DTA. The measurement condition was a temperature increase rate of 10° C./min, a heating temperature of 1,100° C., and an air flow (20 mL/min). FIG. 13 shows the result. The weight decrease observed at 800 to 1,000° C. was understood to correspond to the desorption of the sulfate ion as $SO_3$. The weight increase around 600° C. associated with the exothermic reaction at 584° C. was considered to be derived from further oxidation of the thiosulfate ion to a sulfate ion. The thiosulfate ion was considered to be formed through oxidation of $HS^-$ or $S_k^{2-}$ among the layers of the LDH, and the heat generation and the weight increase at 86° C. were understood to correspond to oxidation to the thiosulfate ion.

A sulfide ion-containing LDH produced by changing the $HS^-$ or $S_k^{2-}$ source to be mixed with the solvent (methanol) in the production procedure of the sulfide ion-containing LDH in this example to $Na_2S_4$ (produced by Dojindo Laboratories Co., Ltd.), which was a polysulfide having a larger amount of S than $Na_2S_3$, also exhibited the similar result in the $H_2S$ release experiment as in this example.

Example 4

This example is a production example using the ion exchange method via an easily anion exchangeable LDH other than the Cl type LDH. $ClO_4^-$ and $NO_3^-$ were used as the anion of the easily anion exchangeable LDH.

Firstly, the $ClO_4^-$MgAl-LDH3 and the $NO_3^-$MgAl-LDH3, which each were an easily anion exchangeable LDH, were prepared.

The $ClO_4^-$MgAl-LDH3 was prepared in the following procedure according to the method described in Japanese Patent No. 5,867,831. 112 mg of perchloric acid (60%, guaranteed reagent, produced by Kanto Chemical Co., Inc.) was dissolved in 5 mL of ethanol to prepare a perchloric acid ethanol solution. Subsequently, 100 mg of the $CO_3^{2-}$ MgAl-LDH3 was suspended in 45 mL of ethanol under a nitrogen gas flow (500 mL/min), to which the perchloric acid ethanol solution was added dropwise under stirring the suspension liquid with a magnetic stirrer, and the mixture was reacted at room temperature (20 to 25° C.) for 1 hour under stirring. Thereafter, under a nitrogen flow, the mixture was filtered with a membrane filter having a pore diameter of 0.2 μm, and the precipitate was sufficiently washed with methanol. The precipitate thus filtered was collected and recovered, immediately decompressed, and dried in vacuum for 1 hour or more, so as to provide 116 mg of white powder.

In the infrared absorption profile measured by FTIR (Fourier transform infrared spectroscopy) of the resulting white powder, disappearance of the absorption of the carbonate ion at 1,360 cm$^{-1}$, and intense characteristic absorption of $ClO_4^-$ at 1,090 to 1,100 cm$^{-1}$ were confirmed, from which it was judged that the $ClO_4^-$MgAl-LDH3 was formed.

The $NO_3^-$MgAl-LDH3 was prepared in the following manner. 159 mg of $NH_4NO_3$ (guaranteed reagent, produced by Kanto Chemical Co., Inc.), 50 mL of methanol, and 100 mg of the $CO_3^{2-}$MgAl-LDH3 were prepared, and the entire amount of $NH_4NO_3$ was dissolved in a part (10 mL) of methanol, and then the $CO_3^{2-}$MgAl-LDH3 was suspended with the remaining methanol.

Subsequently, under a nitrogen gas flow (500 mL/min), the methanol solution of $NH_4NO_3$ was added to the suspension liquid, and the mixture was reacted under stirring for 1.5 hours. After the reaction, under a nitrogen flow, the mixture was filtered with a membrane filter having a pore diameter of 0.2 μm, and the filtered matter (residue) was sufficiently washed with methanol. The residue thus filtered was collected and recovered, immediately decompressed, and dried in vacuum for 1 hour or more, so as to provide white powder.

In the infrared absorption profile of the resulting white powder, the characteristic absorptions of $NO_3^-$ and $CO_3^{2-}$ were difficult to distinguish from each other since the wave numbers thereof were close to each other, and therefore the intercalation of $NO_3^-$ among the layers of the LDH was confirmed by CHN analysis. As a result, the analysis value of N was 3.6 wt %, from which it was judged that the $NO_3^-$MgAl-LDH3 was formed.

Subsequently, a sulfide ion-containing LDH was produced from the $ClO_4^-$MgAl-LDH3 and the $NO_3^-$MgAl-LDH3 obtained.

20 mg of each of the $ClO_4^-$MgAl-LDH3 and the $NO_3^-$MgAl-LDH3 each were weighed and placed in a 30 mL glass vial.

In a globe box with a nitrogen atmosphere, a solution obtained by dissolving 13.4 mg of NaHS·nH$_2$O in 20 mL of degassed methanol was added to the glass vial housing the $ClO_4^-$MgAl-LDH3, and a solution obtained by dissolving 14.5 mg of NaHS·nH$_2$O in 20 mL of degassed methanol was added to the glass vial housing the $NO_3^-$MgAl-LDH3, which each were dispersed by ultrasonification.

The ion-exchange reaction was performed for 2 days in each of the glass vials hermetically sealed, and then in the globe box, the solutions each were filtered with a membrane filter having a pore diameter of 0.2 μm, and the filtered matter (residue) was washed with degassed methanol, decompressed along with the membrane filter, and dried in vacuum for approximately 20 minutes, so as to provide a white powder specimen (sulfide ion-containing LDH) in both cases.

Subsequently, a package hermetically housing the sulfide ion-containing LDH was produced.

In the globe box, the membrane filters holding the resulting sulfide ion-containing LDH each were cut into ¼, and were placed in a 13.5 mL glass container (packaging material) along with the sulfide ion-containing LDH, and the container was hermetically sealed to provide a package.

Figure 14:
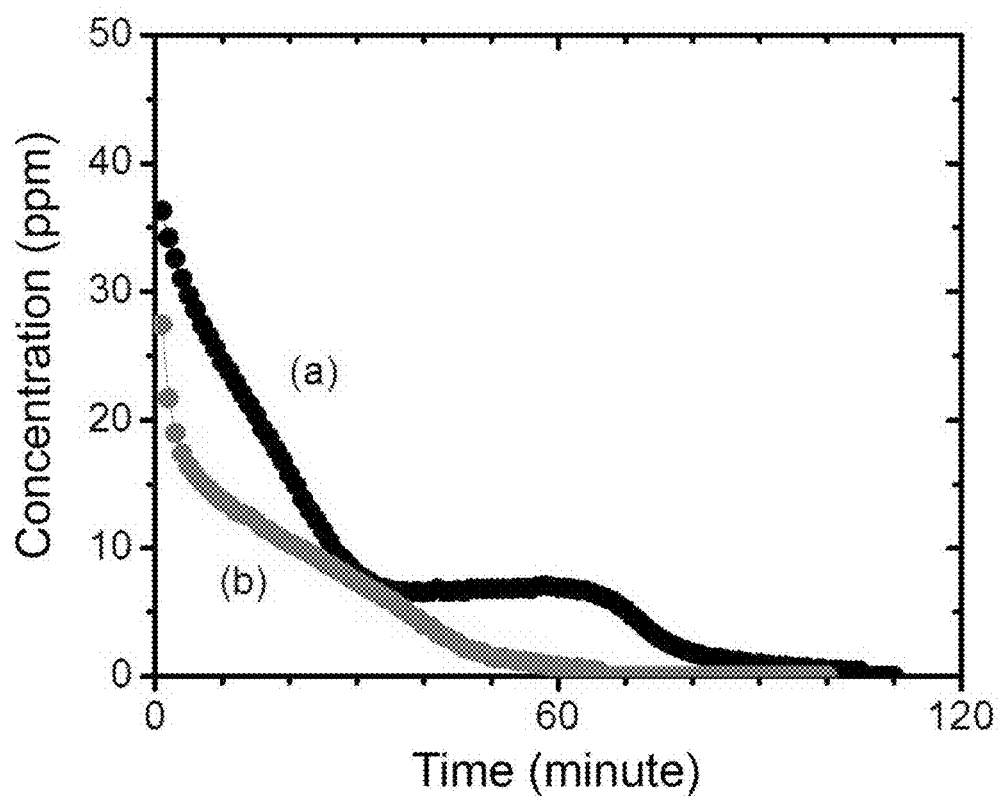
FIG. 14 is a graph showing the time course change of the concentration of $H_2S$ released from the sulfide ion-containing LDH in Example 4 ((a): the specimen obtained via $ClO_4^-$-MgAl-LDH3, (b): the specimen obtained via $NO_3^-$-MgAl-LDH3).

The sulfide ion-containing LDH in the resulting package was subjected to the $H_2S$ release experiment in the same manner as in Example 1. FIG. 14 shows the time course change of the concentration of $H_2S$. In the figure, (a) is the release curve of the product obtained from the $ClO_4^-$MgAl-LDH3, and (b) is the release curve of the product obtained from the $NO_3^-$MgAl-LDH3. In both the release curves, the concentration was increased to show the maximum value immediately after the contact with air, and then the concentration was gradually decreased. The period of time where $H_2S$ was detected was approximately 90 minutes after the detection of the maximum value for the product (a) derived from the $ClO_4^-$MgAl-LDH3, and approximately 60 minutes after the detection of the maximum value for the product (b) derived from the $NO_3^-$MgAl-LDH3, from which it was found that the sulfide ion-containing LDH obtained in this example had hydrogen sulfide sustained releasability.

It is considered that the difference in release curve due to the difference in the intermediate easily anion exchangeable LDH is caused by the factors including (i) the difference of the ion exchange rate, (ii) the difference of the diffusion rate of the intercalated $HS^-$ or $S_k^{2-}$ derived from the difference in size between $ClO_4^-$ and $NO_3^-$ remaining among the layers, and (iii) the change of $HS^-$ or $S_k^{2-}$ through reaction with $ClO_4^-$ and $NO_3^-$ having oxidizability.

Example 5

This example is a production example of an LDH containing a divalent ion other than $Mg^{2+}$. Specifically, an LDH containing a Ni ion as a divalent metal ion and an Al ion as a trivalent metal ion was produced.

Firstly, a carbonate type LDH containing a Ni ion as a divalent metal ion and an Al ion as a trivalent metal ion was produced.

409 mg of $Ni(NO_3)_2 \cdot 6H_2O$ (guaranteed reagent, produced by Kanto Chemical Co., Inc.), 176 mg of $Al(NO_3)_3 \cdot 9H_2O$ (guaranteed reagent, produced by Kanto Chemical Co., Inc.), and 254 mg of urea (guaranteed reagent, produced by Kanto Chemical Co., Inc.) were dissolved in ion exchanged water to prepare 12.5 mL of a mixed aqueous solution, and the solution was placed in a pressure tight Teflon (registered trade mark) vessel having a capacity of 25 mL, which was housed and sealed in a pressure tight stainless steel vessel (produced by San-Ai Kagaku Co., Ltd.), and subjected to a hydrothermal treatment at 180° C. for 3 days. 188 mg of a product was obtained through filtration, washing, and drying. The product had a particle diameter of 0.2 to 0.6 µm, and ICP-AES analysis thereof revealed that the Ni/Al molar ratio was 2.91 (±0.06). This LDH is hereinafter referred to as $CO_3^{2-}$ NiAl-LDH3.

Subsequently, the resulting $CO_3^{2-}$NiAl-LDH3 was converted to the $ClO_4^-$NiAl-LDH3 in accordance with the following procedure.

140 mg of perchloric acid (60%) was dissolved in 5 mL of methanol to prepare a perchloric acid ethanol solution. Subsequently, 268 mg of the $CO_3^{2-}$NiAl-LDH3 was suspended in 45 mL of methanol under a nitrogen gas flow (500 mL/min), to which the perchloric acid ethanol solution was added dropwise under stirring the suspension liquid with a magnetic stirrer, and the mixture was reacted at room temperature (20 to 25° C.) for 1 hour under stirring. Thereafter, under a nitrogen flow, the mixture was filtered with a membrane filter having a pore diameter of 0.2 µm, and the precipitate was sufficiently washed with methanol. The precipitate thus filtered was collected and recovered, immediately decompressed, and dried in vacuum for 1 hour or more, so as to provide 297 mg of blue-green powder.

The Ni/Al molar ratio of the resulting blue-green powder was 2.96 (by ICP analysis), which was approximately the same as the Ni/Al molar ratio=3.0 of the starting material. In the infrared absorption profile measured by FTIR (Fourier transform infrared spectroscopy) of the resulting blue-green powder, the absorption of the carbonate ion at 1,360 $cm^{-1}$ disappeared, and intense characteristic absorption of $ClO_4^-$ at 1,090 to 1,100 $cm^{-1}$ was found, from which it was understood that the $ClO_4^-$NiAl-LDH3 with high purity was obtained. The conversion to the $ClO_4^-$NiAl-LDH3 was also confirmed by the powder X-ray diffraction measurement (RH=0%, measurement under a nitrogen atmosphere), in which reflection of the carbonate type LDH was not observed. The observation of the shapes of the $CO_3^{2-}$NiAl-LDH3 and the $ClO_4^-$NiAl-LDH3 with a scanning electron microscope revealed that both the LDH had the same shape, from which the ion exchange was performed while retaining the external shape.

Subsequently, a sulfide ion-containing LDH was produced from the resulting $ClO_4^-$NiAl-LDH3.

In a globe box with a nitrogen atmosphere, 3.6 mg of $NaHS \cdot nH_2O$ was dissolved in 10 mL of degassed methanol to prepare a NaHS solution.

10.2 mg of the $ClO_4^-$NiAl-LDH3 was weighed and placed in a 20 mL glass vial, to which the NaHS solution was added, and the mixture was dispersed by ultrasonification, in the globe box.

The reaction was performed for 2 days in the glass vial hermetically sealed, and then in the globe box, the mixture was filtered with a membrane filter having a pore diameter of 0.2 µm, and the filtered matter (residue) was washed with degassed methanol, decompressed along with the membrane filter, and dried in vacuum for approximately 20 minutes, so as to provide a blue-green powder specimen (sulfide ion-containing LDH).

Subsequently, a package hermetically housing the sulfide ion-containing LDH was produced.

In the globe box, the membrane filter holding the resulting sulfide ion-containing LDH was cut into ½, and was placed in a 13.5 mL glass container (packaging material) along with the sulfide ion-containing LDH, and the container was hermetically sealed to provide a package.

Figure 15:
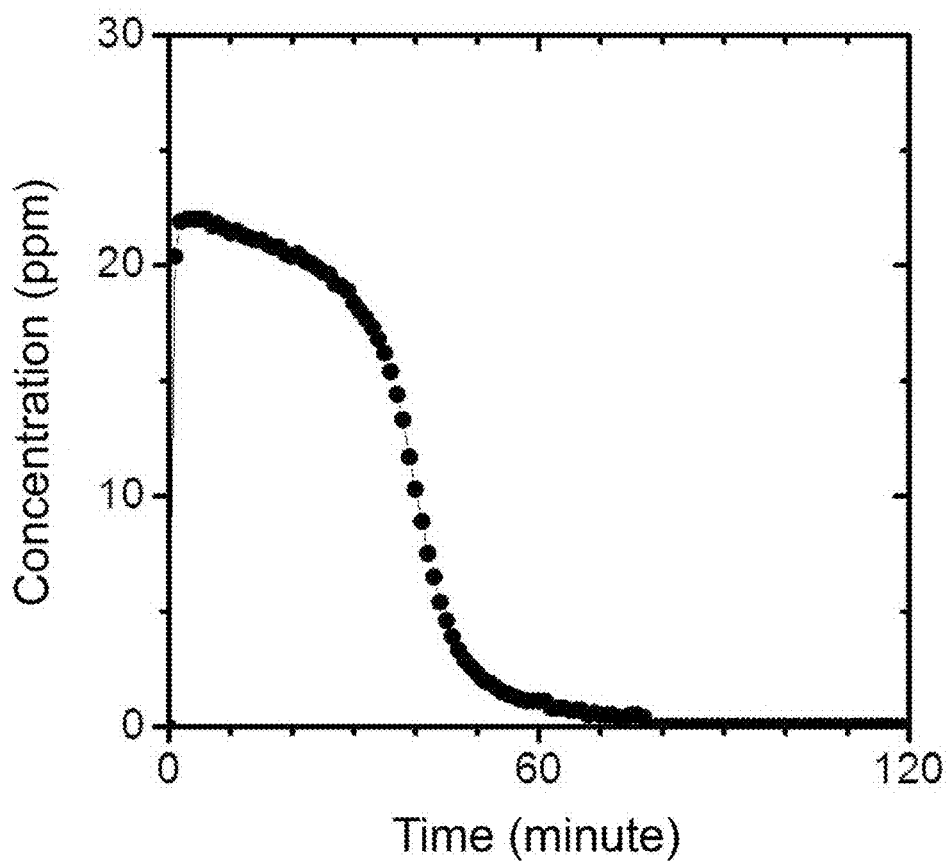
FIG. 15 is a graph showing the time course change of the concentration of $H_2S$ released from the sulfide ion-containing LDH in Example 5.

The sulfide ion-containing LDH in the resulting package was subjected to the $H_2S$ release experiment in the same manner as in Example 1. FIG. 15 shows the time course change of the concentration of $H_2S$. After the contact with air, the concentration was immediately increased and showed the maximum value, and after retaining the similar concentration for a certain period of time, the concentration was gradually decreased. The period of time where $H_2S$ was detected was approximately 70 minutes after the detection of the maximum value, from which it was found that the sulfide ion-containing LDH obtained in this example had hydrogen sulfide sustained releasability.

Accordingly, it can be understood that as for LDHs other than MgAl-LDH, a sulfide ion-containing LDH having hydrogen sulfide sustained releasability can be obtained in the similar production method as in MgAl-LDH.

Example 6

In this example, the relationship between the amount of the $HS^-$ or $S_k^{2-}$ source mixed in the solvent (i.e., the concentration in the solution) and the concentration of $H_2S$ sustainably released was investigated.

Firstly, the $Cl^-$MgAl-LDH3 was prepared in the same manner as in Example 1.

Subsequently, a sulfide ion-containing LDH was produced from the $Cl^-$MgAl-LDH3.

In a globe box with a nitrogen atmosphere, 14 mg (solution a) or 7 mg (solution b) of $NaHS \cdot nH_2O$ was dissolved in 20 mL of degassed methanol to prepare two kinds of NaHS solutions.

25 mg each of the $Cl^-$MgAl-LDH3 was weighed and placed in 30 mL glass vials, and in the glove box, the solution a was added to one of the glass vials, and the solution b was added to the other of the glass vials, both of which were dispersed by sufficiently shaking.

The ion-exchange reaction was performed for 2 days in the glass vials hermetically sealed, and then in the globe box, the solutions each were filtered with a membrane filter having a pore diameter of 0.2 µm, and the filtered matters (residues) each were washed with degassed methanol, decompressed along with the membrane filter, and dried in vacuum for approximately 30 minutes, so as to provide a powder specimen a derived from the solution a and a powder specimen b derived from the solution b (both of which were sulfide ion-containing LDH).

Subsequently, packages hermetically housing the sulfide ion-containing LDH respectively were produced.

In the globe box, the resulting sulfide ion-containing LDH each were placed in a 13.5 mL glass container (packaging material) along with the membrane filter, and the containers were hermetically sealed to provide packages.

Figure 16:
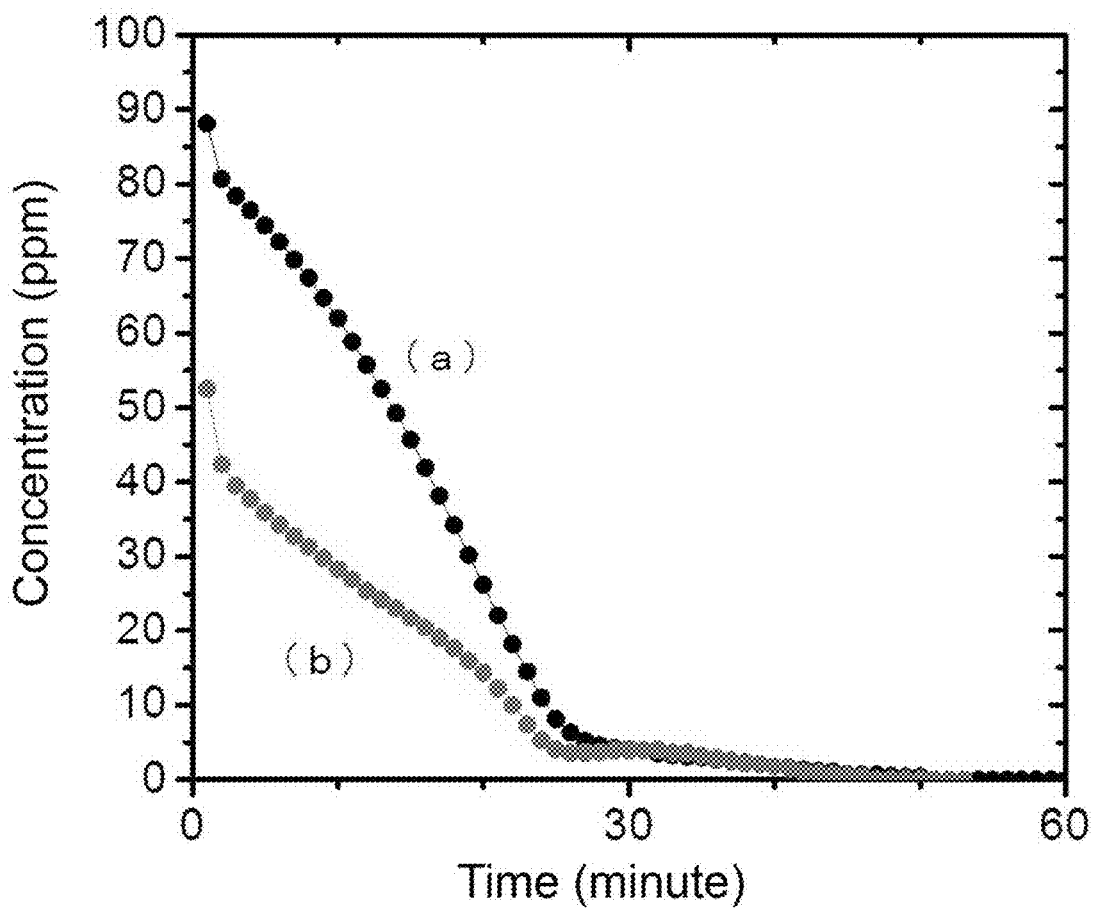
FIG. 16 is a graph showing the time course change of the concentration of $H_2S$ released from the sulfide ion-containing LDH in Example 6 ((a): the specimen obtained with the solution containing 14 mg of $NaHS \cdot nH_2O$, (b): the specimen obtained with the solution containing 7 mg of $NaHS \cdot nH_2O$).

The sulfide ion-containing LDH in the resulting packages were subjected to the $H_2S$ release experiment in the same manner as in Example 1. FIG. 16 shows the time course change of the concentration of $H_2S$. In the figure, (a) corresponds to the result of the powder specimen a, and (b) corresponds to the result of the powder specimen b. Immediately after the start of release, the concentration of $H_2S$ released from the powder a was approximately twice the powder b. In the integration of the release curves, the integrated value of the concentration-time was 1,260 ppm·min for the powder a and 640 ppm·min for the powder b, and the total release amount of the powder a was twice that for the powder b.

Accordingly, it can be understood from the result that the release amount of $H_2S$ from the powder specimen (hydrogen sulfide sustained release agent) is approximately proportional to the concentration of $HS^-$ or $S_k^{2-}$ in the solution used in the production thereof, and thus can be controlled.

Example 7

In this example, a sulfide ion-containing LDH was produced by the so-called reconstruction method. The reconstruction method is such a method as described above that the decarobonation is performed through breakage of the layer structure by heat-treating the carbonate type LDH to 500° C. to 600° C., and then the LDH is added to a solution containing an anion to be included, so that the layer structure is reconstructed, and simultaneously the anion is introduced among the layers.

Firstly, the layer structure of the carbonate type LDH was broken.

500 mg of the $CO_3^{2-}$-MgAl-LDH3 (DHT-6, produced by Kyowa Chemical Industry Co., Ltd.) was placed in a platinum crucible and heat-treated at 500° C. for 2 hours in the air, and then placed in a vacuum vessel, which was decompressed, and cooled in vacuum.

Figure 17:
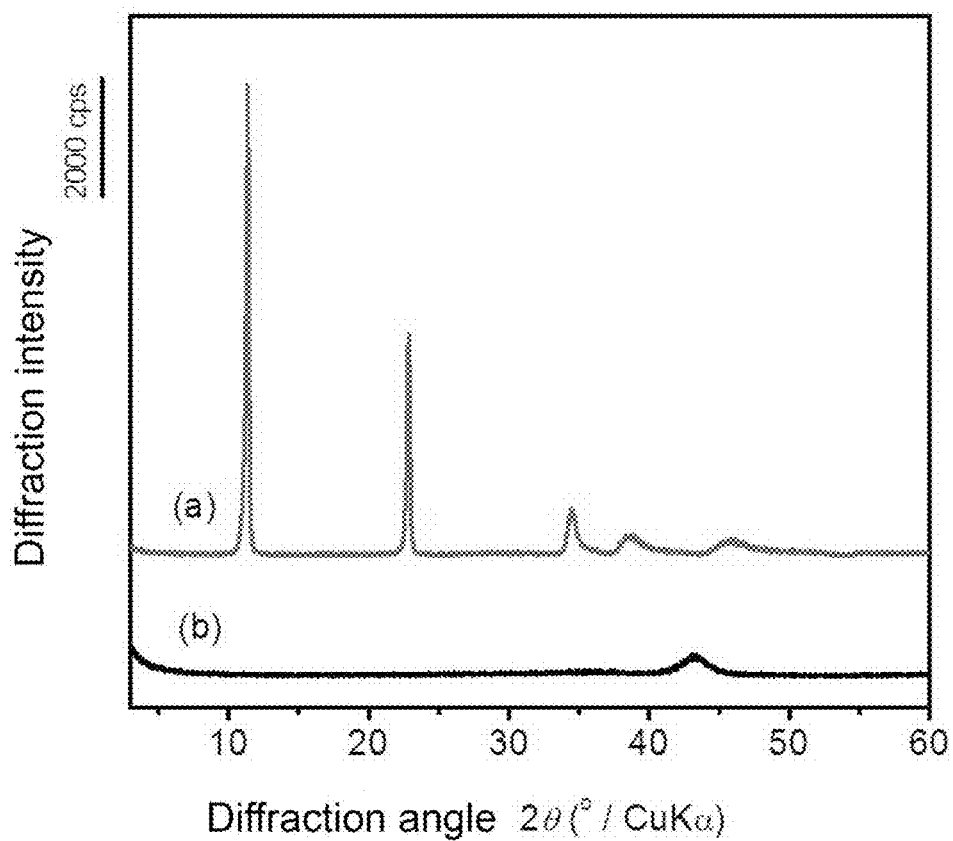
FIG. 17 is a graph showing the XRD measurement result of the $CO_3^{2-}$-MgAl-LDH3 powder before and after the heat treatment in Example 7 ((a): before the heat treatment, (b): after the heat treatment).

FIG. 17 shows the XRD measurement result of the powder before and after the heat treatment. In the figure, (a) shows the profile of the $CO_3^{2-}$-MgAl-LDH3 before the heat treatment, and (b) shows the profile of the powder after the heat treatment (which may be hereinafter referred to as HT-LDH3). It was confirmed from the figure that the sharp reflection (00L) of the $CO_3^{2-}$-MgAl-LDH3 disappeared through the heat treatment, and thus the layer structure was broken.

Subsequently, the layer structure of the LDH having a broken layer structure was reconstructed, so as to produce a sulfide ion-containing LDH.

In a glove box with a nitrogen atmosphere, a 0.3 M $Na_2S$ solution was prepared with degassed ion exchanged water and $Na_2S \cdot 9H_2O$.

25.8 mg of the HT-LDH3 was weighed and placed in a 20 mL glass vial, to which 5 mL of the $Na_2S$ solution was added, and the mixture was dispersed by sufficiently shaking, in the globe box.

The reaction was performed by allowing the glass vial hermetically sealed to stand in the glove box for 3 days, and then in the globe box, the mixture was filtered with a membrane filter having a pore diameter of 0.2 μm, and the filtered matter (residue) was washed with degassed ion exchanged water, decompressed along with the membrane filter, and dried in vacuum for approximately 40 minutes, so as to provide a powder specimen (sulfide ion-containing LDH).

Subsequently, a package hermetically housing the sulfide ion-containing LDH was produced.

In the globe box, the membrane filter having the resulting sulfide ion-containing LDH attached thereto was cut into ⅛, and was placed in a 13.5 mL glass container (packaging material) along with the sulfide ion-containing LDH, and the container was hermetically sealed to provide a package.

Figure 18:
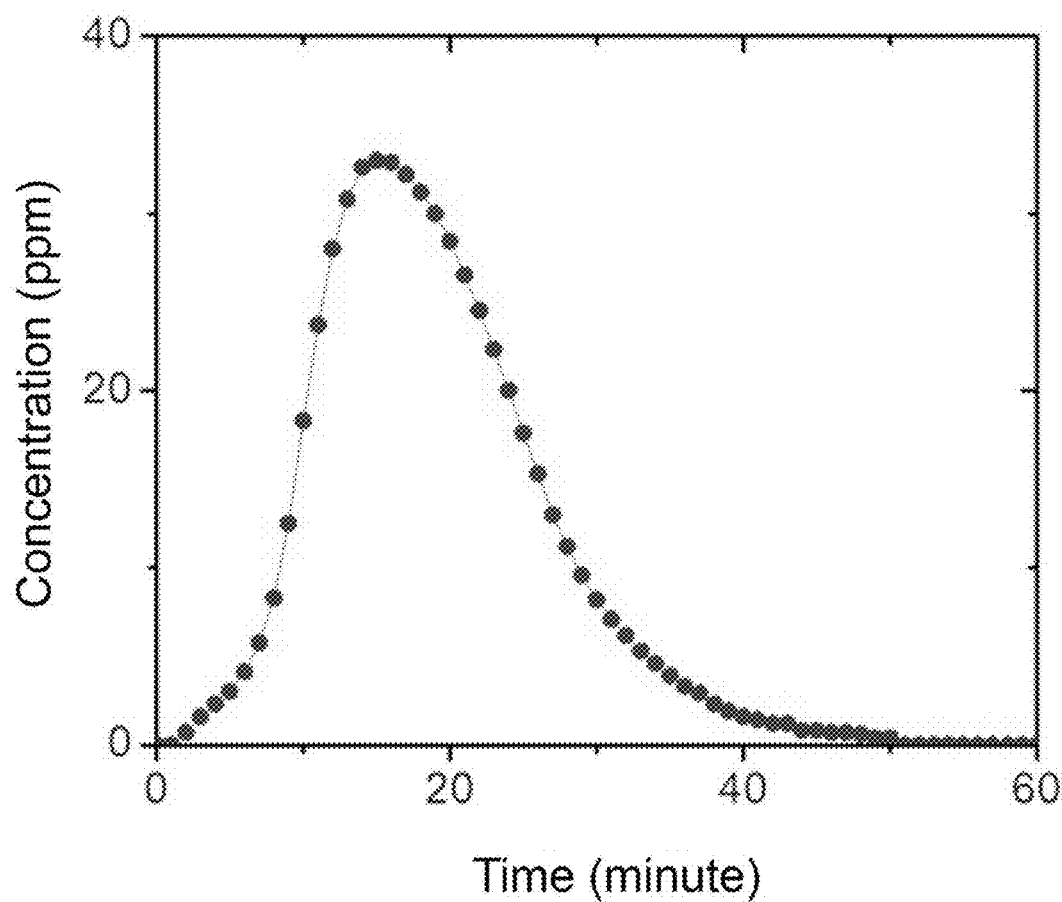
FIG. 18 is a graph showing the time course change of the concentration of $H_2S$ released from the sulfide ion-containing LDH in Example 7.

The sulfide ion-containing LDH in the resulting package was subjected to the $H_2S$ release experiment in the same manner as in Example 1. FIG. 18 shows the measurement result. After approximately 2 minutes from the contact with air, the concentration was gradually increased and showed the maximum value after ten and several minutes, and then the concentration was gradually decreased. The period of time where $H_2S$ was detected was approximately 35 minutes from the detection of the maximum value, from which it was found that the sulfide ion-containing LDH obtained in this example had hydrogen sulfide sustained releasability.

The sulfide ion-containing LDH after the production was subjected to thermal analysis with TG-DTA. The measurement was conducted at a heating rate of 10° C./min to 1,100° C., under air flow (20 mL/min).

Figure 19A:
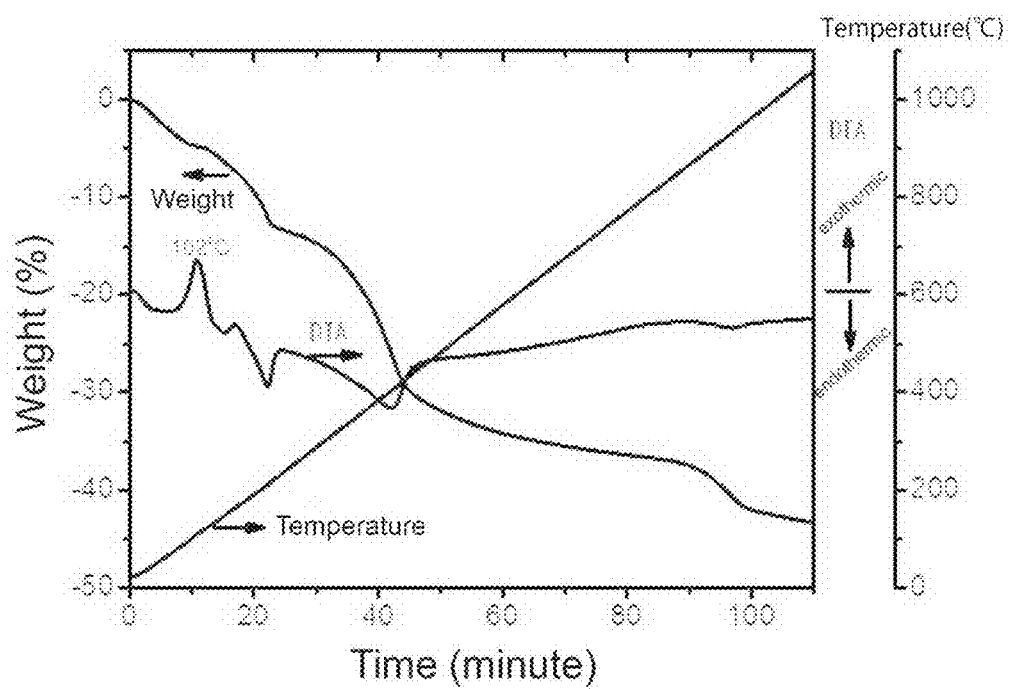
FIGS. 19(a) and 19(b) are graphs showing the result of the thermal analysis (TG-DTA) of FIG. 19(a) the sulfide ion-containing LDH stored in a nitrogen atmosphere after the production and FIG. 19(b) the sulfide ion-containing LDH after completing the $H_2S$ release test, in Example 7.
Figure 19B:
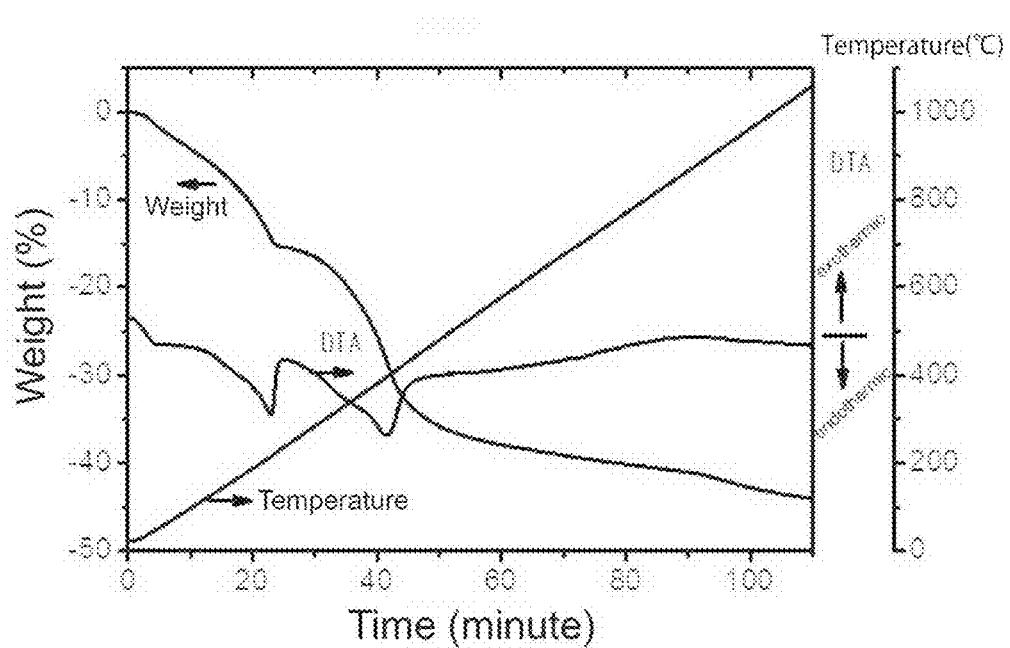

FIG. 19(a) shows the measurement result. Another specimen of the same batch and the same specification was subjected to the $H_2S$ release experiment and then subjected to thermal analysis under the same condition. FIG. 19(b) shows the result thereof. The major difference between the measurement results was the presence or absence of the exothermic peak at 102° C. in DTA, and therefore the peak was understood to be derived from the oxidation reaction of $HS^-$ or $S_k^{2-}$ as the source of the $H_2S$ release. Furthermore, FIG. 19(b) was significantly similar to the thermal analysis profile of $CO_3^{2-}$-LDH.

Figure 20:
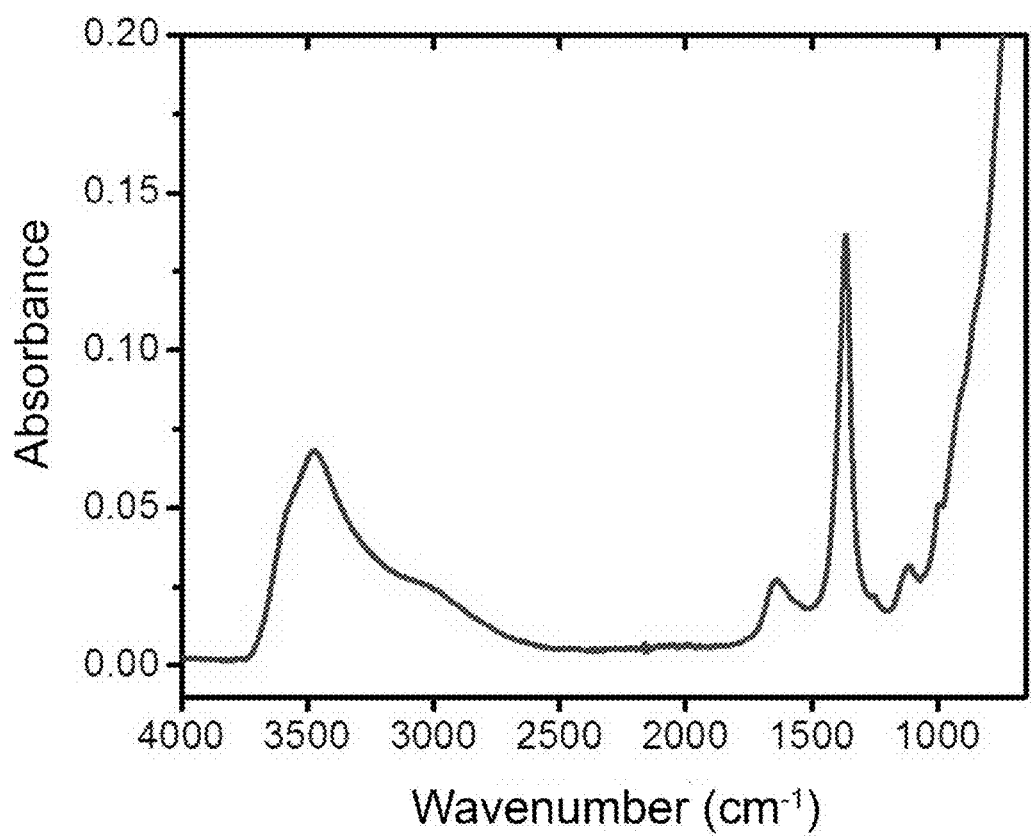
FIG. 20 is a graph showing the Fourier transform infrared spectroscopy (FTIR) of the sulfide ion-containing LDH after completing the $H_2S$ release test in Example 7.

FIG. 20 shows the measurement result of the FTIR (ATR method) of the specimen after completing the $H_2S$ release. The absorption of a carbonate ion ($CO_3^{2-}$) at 1,360 cm$^{-1}$ conspicuously appeared, whereas the absorption of a thiosulfate ion around 1,000 cm$^{-1}$ was very small. It was understood from the result that in the sulfide ion-containing LDH according to one embodiment of the present invention, a very small part of $HS^-$ or $S_k^{2-}$ intercalated among the layers of the LDH was oxidized to form a thiosulfate ion and a sulfate ion, but most thereof was substituted by $CO_3^{2-}$ and released as $H_2S$ to the air atmosphere, and the sulfide ion-containing LDH became a $CO_3^{2-}$-LDH.

The DTA profile and the infrared absorption profile shown in NPL 2 are significantly similar to those of the specimen after completing the $H_2S$ release measured in this example. This means that the specimen shown in NPL 2 is an LDH where $HS^-$ or $S_k^{2-}$ as the source of $H_2S$ has been substituted by $CO_3^{2-}$ because of the atmosphere during the synthesis or the method of storage, and is understood to have no function as a hydrogen sulfide sustained release agent.

Example 8

In this example, the package including the sulfide ion-containing LDH and the packaging material hermetically housing the layered double hydroxide was stored for a prolonged period of time and compared to one immediately after the production, so as to investigate the stability of the $H_2S$ sustained releasability.

A package hermetically housing the sulfide ion-containing LDH was produced by performing the same procedure as in Example 2, using 40.5 mg of the $Cl^-$MgAl-LDH2 synthesized in the manner shown in Example 2, 15 mg of NaHS·$nH_2O$, and 20 mL of degassed methanol. However, the procedure was different from Example 2 in the point that the membrane filter having the sulfide ion-containing LDH attached thereto to be hermetically housed in the glass vial was cut into ⅛.

Figure 21:
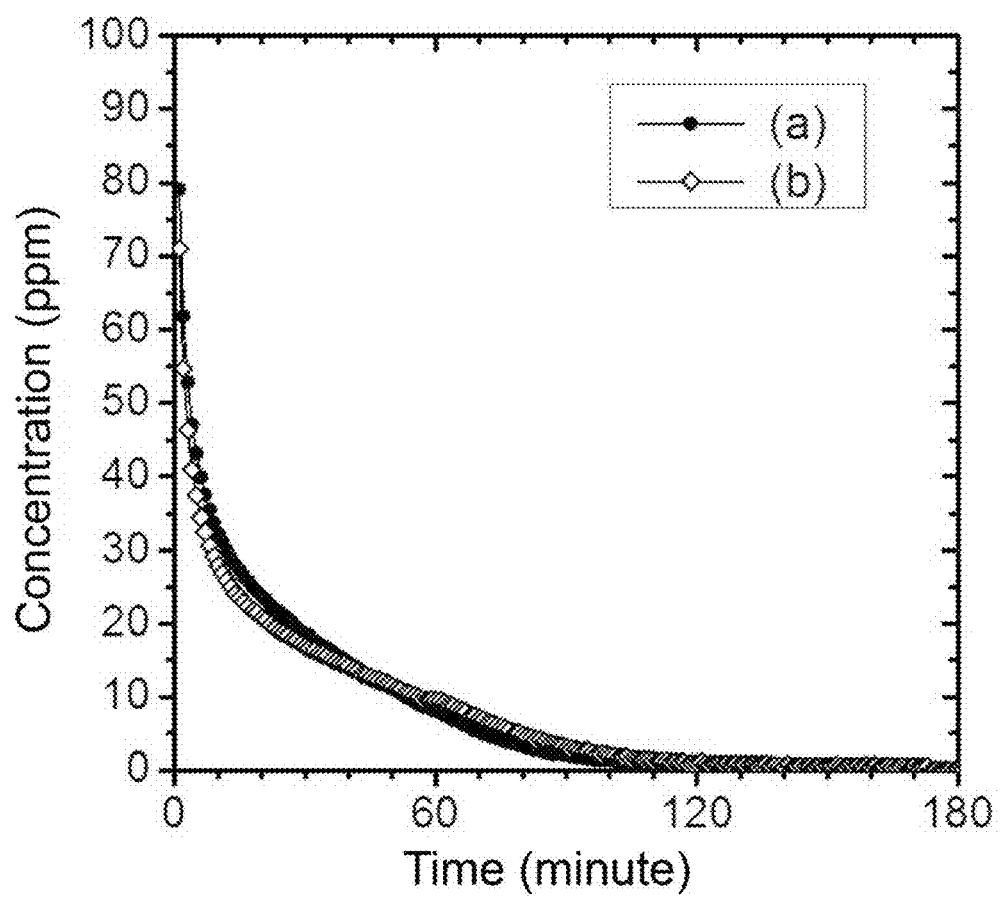
FIG. 21 is a graph showing the time course change of the concentration of $H_2S$ released from the sulfide ion-containing LDH in Example 8 ((a): the specimen immediately after the production, (b): the specimen after storing as the package for two weeks).

The package immediately after the production and the package of the same batch and the same specification after storing at room temperature for 2 weeks after the production were subjected to the $H_2S$ release experiment in the same manner as in Example 1, and the resulting release curves were compared to each other to investigate the presence or absence of the time course change. FIG. 21 shows the result. In the figure, (a) shows the release curve of the package immediately after the production, and (b) shows the release curve of the package stored for 2 weeks. The profiles of the curves were the substantially the same as each other, which showed that the hydrogen sulfide sustained releasability of the sulfide ion-containing LDH was prevented from being deteriorated even after the long term storage, by forming into the package.

Example 9

In this example, the purity of $H_2S$ released from the sulfide ion-containing LDH was investigated. For the medical purposes, contamination of released $H_2S$ with impurity gas is not preferred. The presence of $SO_2$, which was most likely an impurity component, was investigated.

A package hermetically housing the sulfide ion-containing LDH was produced by performing the same procedure as in Example 2. However, the procedure was different from Example 2 in the points that the amount of the $Cl^-$MgAl-LDH2 used was 10 mg, the amount of $Na_2S·9H_2O$ used was 19.3 mg, the amount of the degassed methanol used was 10 mL, and the membrane filter having the sulfide ion-containing LDH attached thereto to be hermetically housed in the glass vial was cut into ¼.

The resulting package was subjected to the $H_2S$ release experiment in the same manner as in Example 1. For investigating the presence of sulfur dioxide, air (20° C., 50% RH) was supplied to the package produced in the same manner as above at a flow rate of 100 mL/min, and air containing $H_2S$ released from the sulfide ion-containing LDH was collected to a Tedlar (registered trade mark) bag for the initial 10 minutes, and measured for the concentrations of hydrogen sulfide and sulfur dioxide with commercially available detector tubes. The detector tubes used were one for hydrogen sulfide (Model 4L, produced by Gastec Corporation) and one for sulfur dioxide (Model 5Lb, produced by Gastec Corporation).

As a result, the concentration of hydrogen sulfide was approximately 50 ppm, which conformed to the result of the $H_2S$ release experiment. The detector tube for sulfur dioxide had no change in color, and the concentration was 0.01 ppm as the detection limit of the detector tube or less. It was understood therefrom that the gas released from the specimen contained substantially no sulfur dioxide.

Example 10

As the synthesis method of the sulfide ion-containing LDH, the "coprecipitation method" was employed, in which an aqueous solution containing metal ions constituting the cation layer and an alkali solution containing a sulfide ion were mixed to form a precipitate.

Firstly, 204 mg of $MgCl_2·6H_2O$ and 121 mg of $AlCl_3·6H_2O$ were weighed and dissolved in 5 mL of degassed ion exchanged water to prepare a $MgCl_2$—$AlCl_3$ solution. Separately, 129 mg of NaHS·$nH_2O$ and 5 mL of degassed ion exchanged water were placed in a 40 mL glass vial to prepare a NaHS solution, and 2.5 mL of 1 M NaOH (produced by Wako Pure Chemical Industries, Ltd.) was added to the solution to prepare a NaHS—NaOH solution. To the NaHS—NaOH solution under vigorously stirring, the $MgCl_2$—$AlCl_3$ solution was added dropwise, and the pH was finally controlled to approximately 10.5.

After the glass vial hermetically sealed was stored in a nitrogen atmosphere at 75° C. for 2 days for ripening, a 5 mL portion was collected from the resulting suspension liquid and filtered with a membrane filter having a pore diameter of 0.2 μm, and the filtered matter (residue) was washed with degassed ion exchanged water. The membrane filter was folded in half, then cut into ¼, and dried in vacuum for 1 hour or more to provide a sulfide ion-containing LDH. The operation up to this point was performed in a glove box with a nitrogen atmosphere.

In a glove box with a nitrogen atmosphere, subsequently, the resulting sulfide ion-containing LDH was placed in a 13.5 mL glass container (packaging material) along with the membrane filter piece having the LDH thereon, and the container was hermetically sealed to provide a package according to Example 10.

Figure 22:
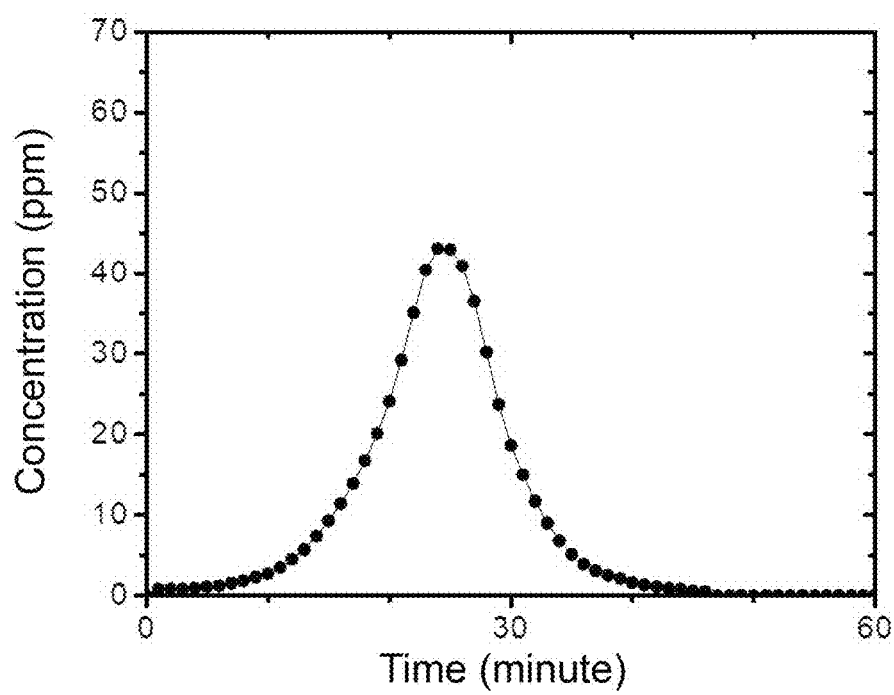
FIG. 22 is a graph showing the time course change of the concentration of $H_2S$ released from the sulfide ion-containing LDH in Example 10.

The sulfide ion-containing LDH in the resulting package was subjected to the $H_2S$ release experiment in the same manner as in Example 1. FIG. 22 shows the measurement result. After the contact with air, the concentration was gradually increased and showed the maximum value after approximately 20 minutes, and then the concentration was gradually decreased. The period of time where $H_2S$ concentration was 1/100 or more of the maximum value was approximately 35 minutes.

The sulfide ion-containing LDH after the $H_2S$ release experiment was subjected to FT-IR measurement (ATR method). The resulting infrared absorption profile was similar to the result of Example 2 shown in FIG. 9, in which the absorption of a carbonate ion ($CO_3^{2-}$) at 1,360 $cm^{-1}$ conspicuously appeared, and the characteristic absorption at 3,416 $cm^{-1}$ and 1,622 $cm^{-1}$ peculiar to the layered double hydroxide was also observed. Furthermore, substantially no absorption was observed around 1,000 $cm^{-1}$, from which it was estimated that the sulfur-containing anion in the sulfide ion-containing LDH was substituted by $CO_3^{2-}$ and released as $H_2S$, without the formation of a thiosulfate ion and a sulfate ion among the layers, as similar to Example 2.

The sulfide ion-containing LDH after the $H_2S$ release experiment was subjected to an X-ray diffraction (XRD) measurement with a powder X-ray diffractometer (Rigaku RINT-2200V), and as a result, a profile that substantially agreed with the $CO_3^{2-}$MgAl-LDH2 was obtained, which confirmed the layer structure. The layer spacing calculated from the XRD measurement result was 7.7 Å, which was slightly larger than 7.58 Å reported as the layer spacing of the $CO_3^{2-}$MgAl-LDH3 It is considered that this is caused by the S component remaining among the layers, as investigated in Example 2.

It was understood from the result above that the specimen obtained in this example contained the sulfide ion-containing LDH and had hydrogen sulfide sustained releasability.

Examples 11 and 12

In these examples, it was confirmed that the sulfide ion-containing LDH that was formed into a granulated material or a powder compact material had higher hydrogen sulfide sustained releasability through enhancement of the sustained releasability.

40.5 mg of the Cl$^-$MgAl-LDH2 prepared in the same manner as in Example 2 was placed in a 50 mL glass vial. Separately, 36.6 mg of NaHS·nH$_2$O was dissolved in 30 mL of degassed ion exchanged water to prepare a NaHS solution. The NaHS solution was added to the glass vial and dispersed by ultrasonification, and then the mixture was reacted at room temperature for 2 days in the glass vial hermetically sealed. The entire amount of the liquid after the reaction was filtered with a membrane filter having a pore diameter of 0.2 μm, and an operation of washing the filtered matter (residue) with 2 mL of degassed ion exchanged water was performed 5 times. Thereafter, the membrane filter having the residue thereon was cut into quarters, and dried in vacuum for 2 hours. The operation up to this point was performed in a glove box with a nitrogen atmosphere.

Figure 23:
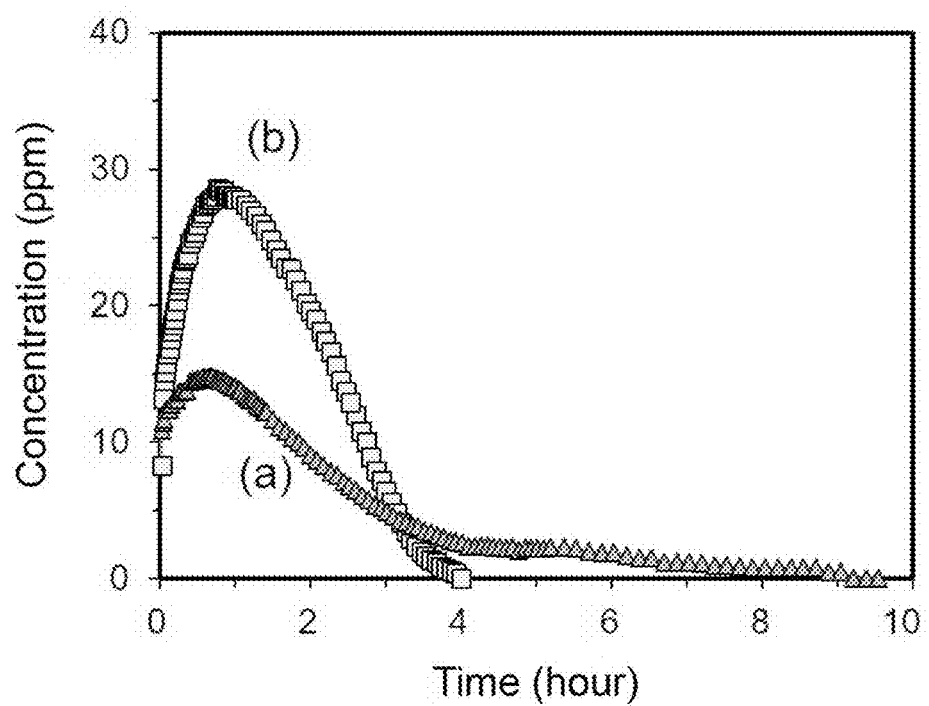
FIG. 23 is a graph showing the time course change of the concentration of $H_2S$ released from the sulfide ion-containing LDH in Examples 11 and 12 ((a): Example 11, (b): Example 12).

The dried membrane filter was folded with the surface having the residue (sulfide ion-containing LDH) attached thereto directed inside, and a compression treatment of holding the membrane filter with two metal flat plates and pressing the assembly with a vise was performed twice. After the compression treatment, the folded membrane filter was opened to make a state where the sulfide ion-containing LDH having been compressed was in direct contact with the external atmosphere, so as to provide a specimen according to Example 11, which was then subjected to the H$_2$S release experiment in the same manner as in Example 1. FIG. 23 shows the time course change of the concentration of H$_2$S as (a). In the figure, the result of the specimen according to Example 12, one of the specimens obtained by cut into quarters but not subjected to the compression treatment is also shown as (b). It was confirmed from the comparison between Example 11 and Example 12 that the compression treatment suppressed the release of H$_2$S in a high concentration in the initial stage of release, suppressed the release concentration over the release time, and prolonged the release time. It is considered that the phenomenon occurs since the density of the specimen (hydrogen sulfide sustained release agent) is increased by the compression treatment, and the diffusion of gas into the interior thereof is suppressed.

Examples 13 and 14

In these examples, it was confirmed that the sulfide ion-containing LDH that had an increased accumulation thickness had higher hydrogen sulfide sustained releasability through enhancement of the sustained releasability.

The reaction liquid of the Cl$^-$MgAl-LDH2 and NaHS was prepared in the same manner as in Example 11 in an amount for two vials.

In the resulting reaction liquid, the entire amount of a part thereof in one of the vials was filtered with a membrane filter having a pore diameter of 0.2 μm, and an operation of washing the filtered matter (residue) with 2 mL of degassed ion exchanged water was performed 5 times. Thereafter, the membrane filter having the residue thereon was cut into quarters, and dried in vacuum for 2 hours, so as to prepare a specimen according to Example 13. The operation of filtration, washing, and drying was performed in a glove box with a nitrogen atmosphere.

Separately, for the reaction liquid in the other of the vials, a half amount thereof (15 mL) was filtered and washed in the same manner as in Example 13, and the membrane filter having the specimen thereon was cut in halves into a semicircular shape and dried in vacuum for 2 hours to prepare a specimen according to Example 14. The specimen according to Example 13 and the specimen according to Example 14 were different in accumulation thickness of the sulfide ion-containing LDH, but the masses thereof were equivalent to each other.

Figure 24:
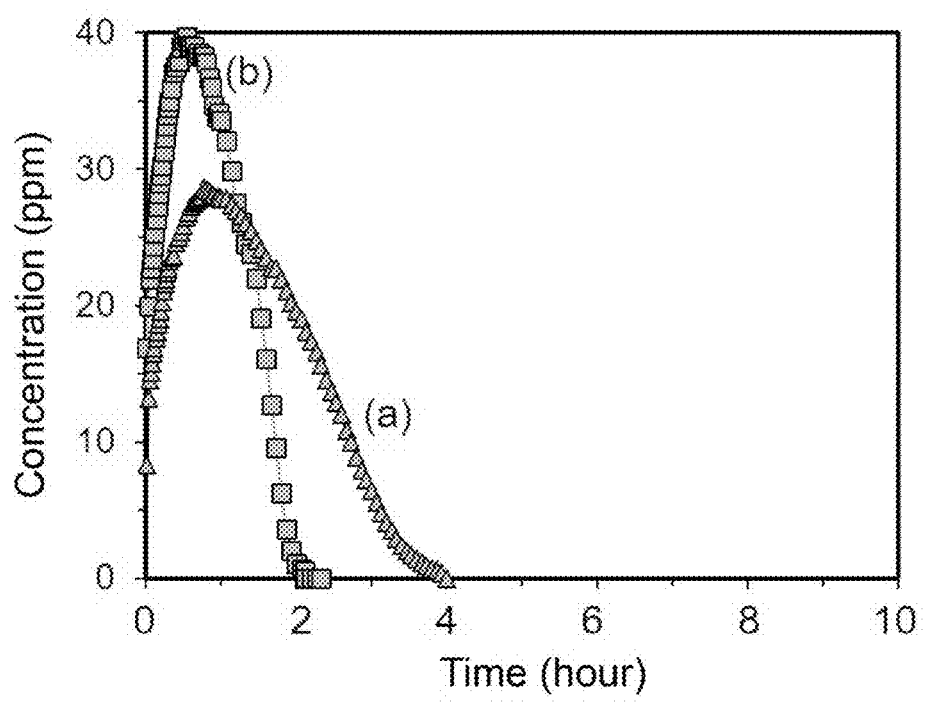
FIG. 24 is a graph showing the time course change of the concentration of $H_2S$ released from the sulfide ion-containing LDH in Examples 13 and 14 ((a): Example 13, (b): Example 14).

The specimens according to Examples 13 and 14 were subjected to the H$_2$S release experiment in the same manner as in Example 1. FIG. 24 shows the time course change of the concentration of H$_2$S. In the figure, (a) shows the result of Example 13, and (b) shows the result of Example 14. It was confirmed from the comparison between Example 13 and Example 14 that the increase of the accumulation thickness of the sulfide ion-containing LDH suppressed the release of H$_2$S in a high concentration in the initial stage of release, suppressed the release concentration over the release time, and prolonged the release time. It is considered that the phenomenon occurs since the increase of the thickness of the specimen decreases the surface area per unit mass, and thereby the contact with the air atmosphere is suppressed.

Example 15

In this example, it was confirmed that an effect of suppressing the peak concentration of H$_2$S released was obtained, by mixing the sulfide ion-containing LDH with an extender.

The reaction liquid of the Cl$^-$MgAl-LDH2 and NaHS was prepared in the same manner as in Example 11.

A half portion (15 mL) of the resulting reaction liquid was filtered with a membrane filter having a pore diameter of 0.2 μm, and an operation of washing the filtered matter (residue) with 2 mL of degassed ion exchanged water was performed 5 times. Thereafter, the membrane filter having the residue thereon was dried in vacuum for 2 hours. The operation of filtration, washing, and drying was performed in a glove box with a nitrogen atmosphere.

The residue was separated from the membrane filter to provide the sulfide ion-containing LDH, and then 7.1 mg of the sulfide ion-containing LDH and 7.0 mg of white petrolatum (produced by Kenei Pharmaceutical Co., Ltd.) were mixed to provide a mixture in a paste form. 7.5 mg of the mixture was applied to a chartula in a square shape having an edge of 2 cm to prepare a specimen according to Example 15, and the specimen was immediately placed and hermetically sealed in a 13.5 mL glass container (packaging material), so as to provide a package according to Example 15.

Figure 25:
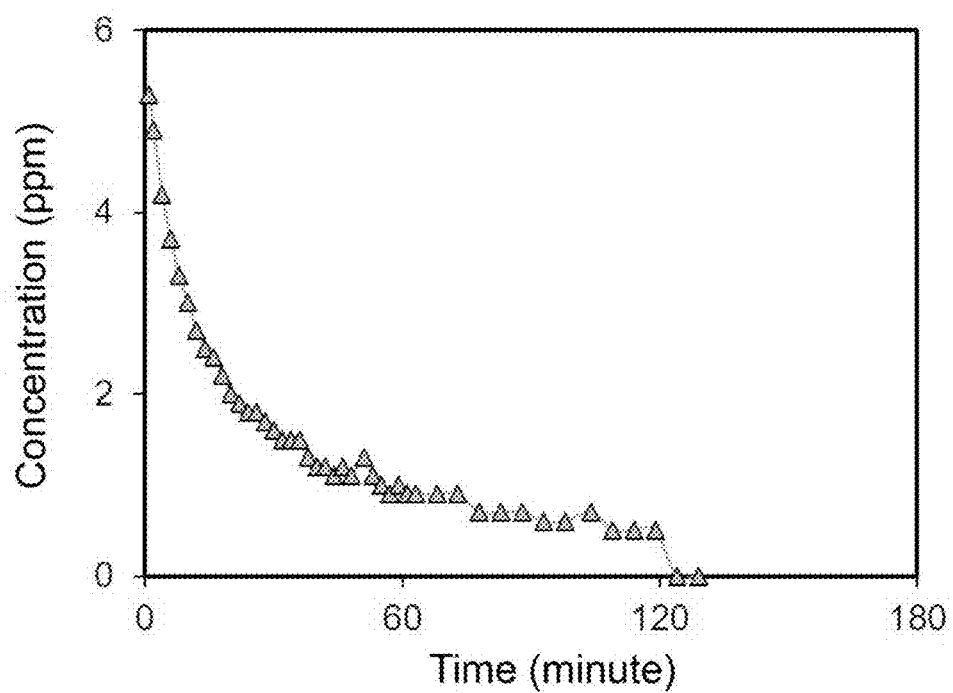
FIG. 25 is a graph showing the time course change of the concentration of $H_2S$ released from the sulfide ion-containing LDH in Example 15.

The specimen according to Example 15 was subjected to the H$_2$S release experiment in the same manner as in Example 1. FIG. 25 shows the time course change of the concentration of H$_2$S. The maximum value of the concentration of H$_2$S released from the specimen was suppressed to 10 ppm or less, from which the effect of suppressing the peak concentration of H$_2$S released was confirmed. It is considered that the phenomenon occurs since the amount of the sulfide ion-containing LDH is decreased, and simultaneously the contact with air of the sulfide ion-containing LDH is suppressed by the petrolatum, thereby decreasing the amount of H$_2$S simultaneously released.

Mixtures of the sulfide ion-containing LDH and an extender (such as petrolatum), for example the mixture in a paste form used in the example, can be used by applying on a surface of a solid matter, such as paper, cloth, filters, glass substrates, and skin, without scattering the powder of the sulfide ion-containing LDH.

Examples 16 to 19

In these examples, it was confirmed that the sulfide ion-containing LDH that was housed in a porous cover or container had higher hydrogen sulfide sustained releasability through enhancement of the sustained releasability.

In Examples 16 and 17, the hydrogen sulfide sustained releasability of the sulfide ion-containing LDH produced from the Cl$^-$MgAl-LDH2 in the case of housing in a porous cover or container was confirmed.

40.5 mg of the Cl$^-$MgAl-LDH2 prepared in the same manner as in Example 2 was placed in a 40 mL glass vial. Separately, 590 mg of NaHS·nH$_2$O was dissolved in 30 mL of degassed ion exchanged water to prepare a NaHS solution. The NaHS solution was added to the glass vial and dispersed by ultrasonification, and then the mixture was reacted for 2 days in the glass vial hermetically sealed. The entire amount of the liquid after the reaction was filtered with a membrane filter having a pore diameter of 0.2 μm, and the filtered matter (residue) was washed with degassed methanol. Thereafter, the membrane filter having the residue thereon was folded in half with the residue directed inside, cut in halves, and then dried in vacuum for approximately 30 minutes, so as to provide the membrane filter piece having the sulfide ion-containing LDH attached inside.

The resulting membrane filter piece was further cut in halves, one of them was placed on an adhesive surface of a porous tape, and another porous tape was adhered thereon to hold the membrane filter piece, so as to form a sandwich cover. The porous tape used was Keep Pore (registered trademark) (produced by Nichiban Co., Ltd.), which was a surgical tape formed of polyethylene. The excess portions of the tape were cut while preventing the membrane filter from being cut, so as to provide a specimen according to Example 16, which was then placed in a 13.5 mL glass container (packaging material), and the container was hermetically sealed to provide a package according to Example 16. The other half of the membrane filter pieces was directly designated as a specimen according to Example 17, which was placed in a 13.5 mL glass container (packaging material), and the container was hermetically sealed to provide a package according to Example 17.

The operation above was performed in a glove box with a nitrogen atmosphere.

Figure 26:
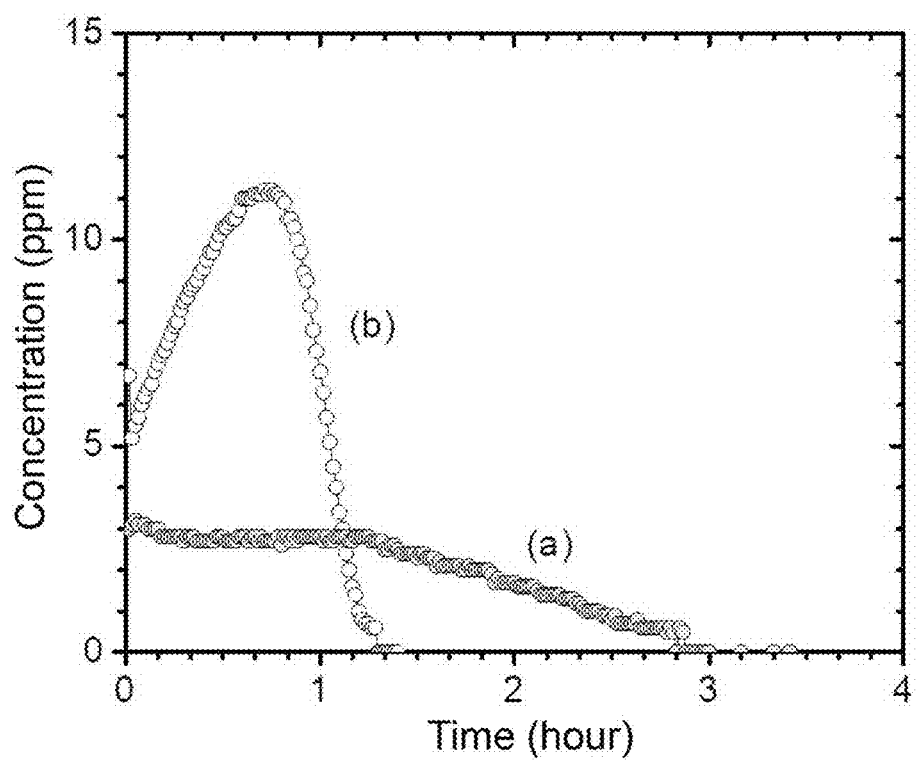
FIG. 26 is a graph showing the time course change of the concentration of $H_2S$ released from the sulfide ion-containing LDH in Examples 16 and 17 ((a): Example 16, (b): Example 17).

The specimens according to Examples 16 and 17 were subjected to the H$_2$S release experiment in the same manner as in Example 1 except that the relative humidity of air introduced was changed to 40% RH. FIG. 26 shows the time course change of the concentration of H$_2$S. In the figure, (a) shows the result of Example 16, and (b) shows the result of Example 17. It was confirmed from the comparison between Example 16 and Example 17 that the housing of the sulfide ion-containing LDH in the porous cover suppressed the release of H$_2$S in a high concentration in the initial stage of release, suppressed the release concentration over the release time, and prolonged the release time.

In Examples 18 and 19, the sulfide ion-containing LDH produced from the CO$_3^{2-}$MgAl-LDH2 via the NO$_3^-$MgAl-LDH2 that was housed in a porous cover or container was confirmed for the hydrogen sulfide sustained releasability.

80.7 mg of the CO$_3^{2-}$MgAl-LDH2 was weighed and placed in a three-neck flask, to which 37.5 mL of methanol was added. Under a nitrogen gas flow (500 mL/min), a solution obtained by dissolving 79.5 mg of NH$_4$NO$_3$ in 10 mL of methanol was added dropwise thereto under stirring the suspension liquid with a magnetic stirrer, and the mixture was reacted at 45° C. for 1 hour under stirring. After the reaction, under a nitrogen gas flow, the mixture was filtered with a membrane filter having a pore diameter of 0.2 μm, and the filtered matter (residue) was sufficiently washed with methanol. The filtered residue was collected and recovered, immediately decompressed, and dried in vacuum for 1 hour or more, so as to provide 89.9 mg of NO$_3^-$MgAl-LDH2 as white powder.

22.0 mg of the resulting NO$_3^-$MgAl-LDH2 was weighed and placed in a 15 mL glass vial. Separately, 14 mg of NaHS·nH$_2$O was dissolved in 10 mL of degassed ion exchanged water to prepare a NaHS solution. The NaHS solution was added to the glass vial and dispersed by ultrasonification, and then the mixture was reacted at room temperature for 2 days in the glass vial hermetically sealed. The liquid after the reaction was filtered with a membrane filter having a pore diameter of 0.2 μm, and the filtered matter (residue) was washed with degassed ion exchanged water. Thereafter, the membrane filter having the residue thereon was folded in half with the residue directed inside and cut into quarters to provide membrane filter pieces. One of the membrane filter pieces was packaged with the porous tape in the same operation as in Example 16, and then placed in a 13.5 mL glass container (packaging material), which was dried in vacuum for approximately 30 minutes, so as to provide a specimen according to Example 18. The glass container was then hermetically sealed to provide a package according to Example 18. The other of the membrane filter pieces was placed directly in a 13.5 mL glass container (packaging material), which was dried in vacuum for approximately 30 minutes, so as to provide a specimen according to Example 19. The glass container was then hermetically sealed to provide a package according to Example 19. The operation of filtration, washing, and drying was performed in a glove box with a nitrogen atmosphere.

Figure 27:
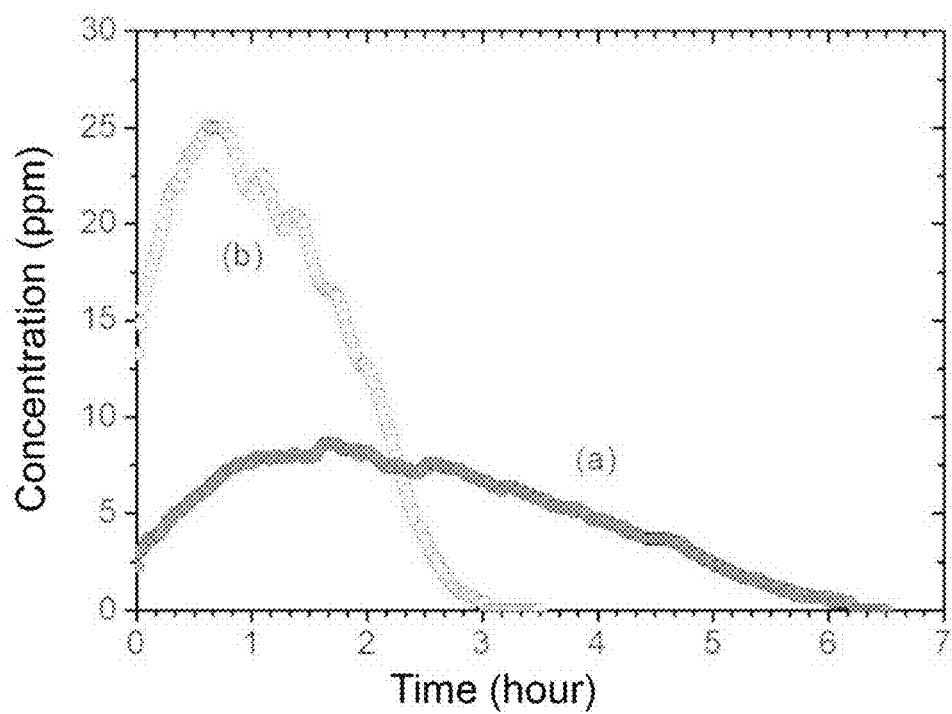
FIG. 27 is a graph showing the time course change of the concentration of $H_2S$ released from the sulfide ion-containing LDH in Examples 18 and 19 ((a): Example 18, (b): Example 19).

The specimens according to Examples 18 and 19 were subjected to the H$_2$S release experiment in the same manner as in Example 1. FIG. 27 shows the time course change of the concentration of H$_2$S. In the figure, (a) shows the result of Example 18, and (b) shows the result of Example 19. It was confirmed from the comparison between Example 18 and Example 19 that the housing of the sulfide ion-containing LDH in the porous cover suppressed the release of H$_2$S in a high concentration in the initial stage of release, suppressed the release concentration over the release time, and prolonged the release time. It is considered that the results in Examples 16 to 19 are obtained since the porous cover suppresses the contact of the sulfide ion-containing LDH with carbon dioxide and water, which is a factor of release of hydrogen sulfide, and also suppresses the diffuse of hydrogen sulfide released from the sulfide ion-containing LDH to the atmosphere.

Examples 20 and 21

In these examples, it was confirmed that the sulfide ion-containing LDH that was washed with water had higher hydrogen sulfide sustained releasability through enhancement of the sustained releasability.

The reaction and filtration were performed in the same manner as in Example 11, and then an operation of washing the filtered matter (residue) on the membrane filter with 2 mL of degassed ion exchanged water was performed 25 times. Thereafter, the membrane filter having the residue thereon was cut in halves into a semicircular shape and dried in vacuum for 2 hours to prepare a specimen according to Example 20. Separately, a specimen according to Example 21 was obtained in the same manner as in Example 20 except that the number of times of the washing operation was changed to 5 times. The washing operation was performed in a glove box with a nitrogen atmosphere. The specimens according to Examples 20 and 21 each were placed and hermetically sealed in a 13.5 mL glass container (packaging material), so as to provide packages according to Examples 20 and 21.

Figure 28:
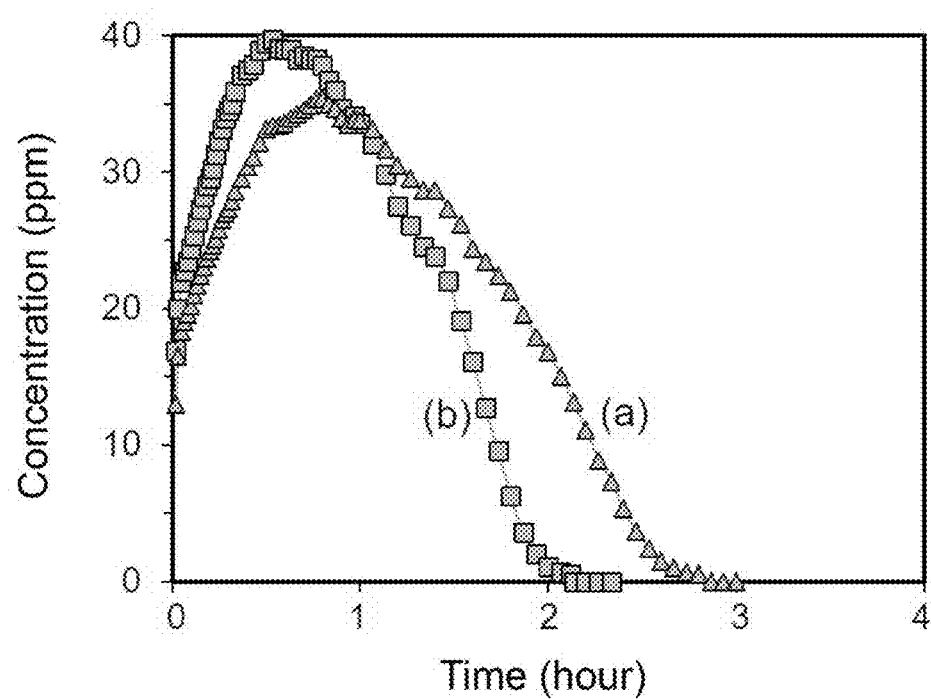
FIG. 28 is a graph showing the time course change of the concentration of $H_2S$ released from the sulfide ion-containing LDH in Examples 20 and 21 ((a): Example 20, (b): Example 21).

The specimens according to Examples 20 and 21 were subjected to the $H_2S$ release experiment in the same manner as in Example 1. FIG. 28 shows the time course change of the concentration of $H_2S$. In the figure, (a) shows the result of Example 20, and (b) shows the result of Example 21. It was confirmed from the comparison between Example 20 and Example 21 that the repetition of water washing of the sulfide ion-containing LDH suppressed the release of $H_2S$ in a high concentration in the initial stage of release, suppressed the release concentration over the release time, and prolonged the release time. It is considered that the phenomenon occurs since the hydrogen sulfide source attached to the surface of the particles, the hydrogen sulfide source retained in the voids among the particles, and $HS^-$ and/or $S_k^{2-}$ intercalated among the layers in the vicinity of the surface of the particles are removed by the water washing.

Examples 22 to 24

In these examples, it was confirmed that the sulfide ion-containing LDH that underwent a combination of the water washing and the housing in a porous cover or container had higher hydrogen sulfide sustained releasability through enhancement of the sustained releasability.

Two 40 mL glass vials were prepared, and 20 mg of the $Cl^-$MgAl-LDH2 prepared in the same manner as in Example 2 was placed in each of the glass vials. Separately, two vessels having 20 mL of degassed methanol placed therein were prepared, and 7.3 mg of $NaHS \cdot nH_2O$ was dissolved in each of the vessels to prepare a NaHS solution. The NaHS solution was added to each of the two glass vials and dispersed by ultrasonification, and then the reaction was performed for 2 days in the glass vials hermetically sealed. The entire amount of the liquids after the reaction each were filtered with a membrane filter having a pore diameter of 0.2 μm, and the filtered matters (residues) were washed with degassed methanol for one of the residues and with degassed ion exchanged water for the other of the residues. Thereafter, the membrane filters each having the residue thereon each were folded in half with the residue directed inside, and cut into ¼. The cut membrane filter piece that was washed with ion exchanged water was placed on an adhesive surface of a porous tape, and another porous tape was adhered thereon to hold the membrane filter, so as to form a sandwich cover, which was dried in vacuum for approximately 30 minutes to provide a specimen according to Example 22. The membrane filter piece that was washed with ion exchanged water and the membrane filter piece that was washed with methanol each were dried in vacuum for approximately 30 minutes to provide specimens according to Examples 23 and 24.

The specimens according to Examples 22 to 24 each were placed and hermetically sealed in a 13.5 mL glass container (packaging material), so as to provide packages according to Examples 22 to 24.

The operation above was performed in a glove box with a nitrogen atmosphere.

Figure 29:
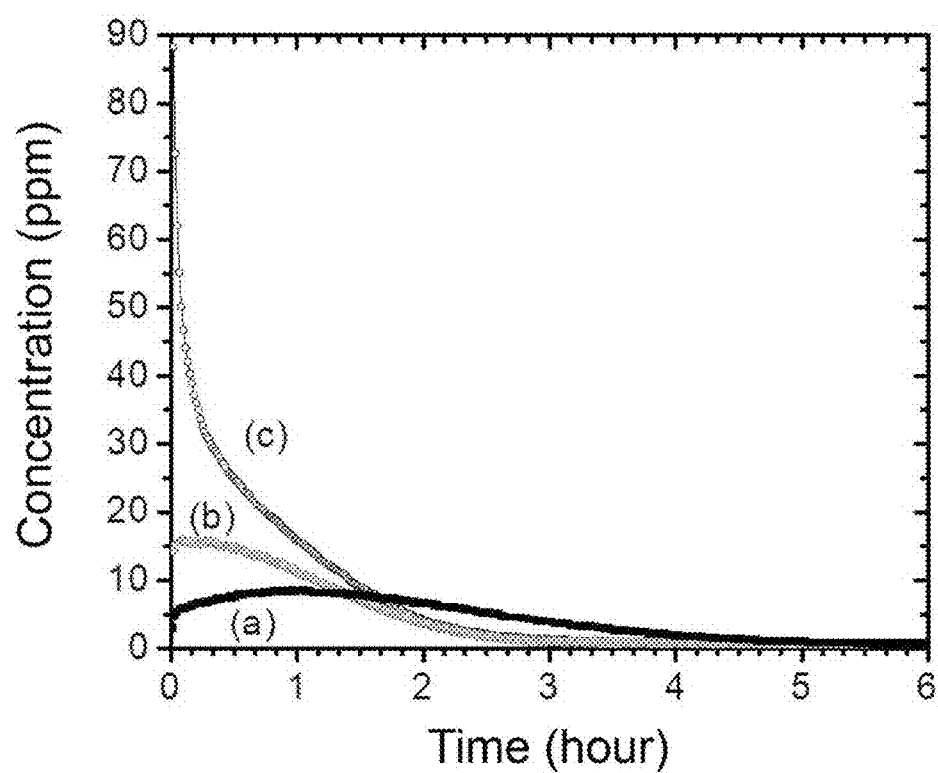
FIG. 29 is a graph showing the time course change of the concentration of $H_2S$ released from the sulfide ion-containing LDH in Examples 22 to 24 ((a): Example 22, (b): Example 23, (c): Example 24).

The specimens according to Examples 22 to 24 were subjected to the $H_2S$ release experiment in the same manner as in Example 1. FIG. 29 shows the time course change of the concentration of $H_2S$. It was found from the comparison of the result of Example 23 shown by (b) in the figure and the result of Example 24 shown by (c) in the figure that the water washing of the sulfide ion-containing LDH suppressed the release in a high concentration in the initial stage and decreased the maximum release concentration. It was also found from the comparison of the result of Example 22 shown by (a) in the figure and the result of Example 23 that the combination of the water washing and the housing in the porous cover further decreased the maximum release concentration, and prolonged the release time, resulting in the significant enhancement of the sustained releasability.

Examples 25 to 27

In these examples, it was confirmed that the sulfide ion-containing LDH that was brought into contact with oxygen had higher hydrogen sulfide sustained releasability through enhancement of the sustained releasability.

The reaction and filtration were performed in the same manner as in Example 11, and then a membrane filter of the same kind was placed on the membrane filter having the filtered matter (residue) thereon, so that the residue was held between two membrane filters. Thereafter, the portion of the membrane filter having the residue thereon was cut into a circular shape with a leather punch having a diameter of 6 mm, and placed on an adhesive surface of a porous tape, and another porous tape was adhered thereon to hold the membrane filter in the form of sandwich. The assembly was dried in vacuum in approximately 2 hours to provide a hydrogen sulfide sustained release composite.

The resulting hydrogen sulfide sustained release composite was sealed in an aluminum laminated bag as a packaging material to provide a package. The package was further sealed in another aluminum laminated bag along with an oxygen absorber (Ageless (registered trade mark), produced by Mitsubishi Gas Chemical Company, Inc.) and a tablet drying agent (D01056, produced by Yamani Yakuhin Co., Ltd.). The operation up to this point was performed in a glove box with a nitrogen atmosphere.

Figure 30:
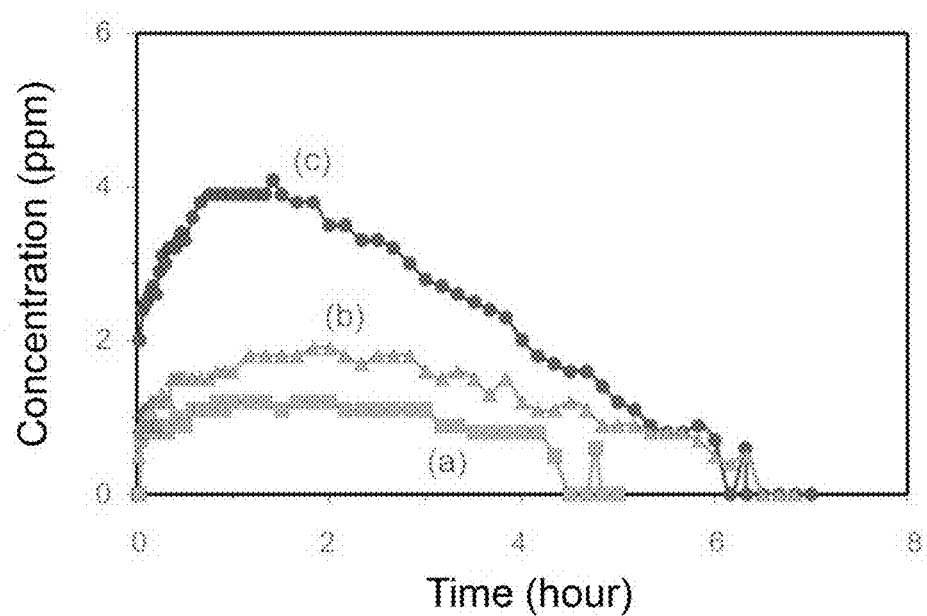
FIG. 30 is a graph showing the time course change of the concentration of $H_2S$ released from the sulfide ion-containing LDH in Examples 25 to 27 ((a): Example 25, (b): Example 26, (c): Example 27).

The package was opened in the air atmosphere, and two sheets of the hydrogen sulfide sustained release composites were taken out and immediately placed in a 13.5 mL glass container. Dry pure oxygen was supplied to the glass container at a flow rate of 300 cc/min, and thereby the sulfide ion-containing LDH was brought into contact with oxygen to provide specimens according to Examples 25 and 26. The period of time of supplying oxygen was 12 hours for Example 25 or 4 hours for Example 26. Thereafter, these specimens and a specimen according to Example 27 that was not subjected to the oxygen treatment were subjected to the $H_2S$ release experiment in the same manner as in Example 1. FIG. 30 shows the time course change of the concentration of $H_2S$. In the figure, (a) shows the result of Example 25, (b) shows the result of Example 26, and (c) shows the result of Example 27. It was confirmed from the result that the contact with oxygen suppressed the release of $H_2S$ in a high concentration in the initial stage of release, and suppressed the release concentration over the release time. It is considered that the phenomenon occurs since the hydrogen sulfide source attached to the surface of the particles, the hydrogen sulfide source retained in the voids among the particles, and $HS^-$ and/or $S_k^{2-}$ intercalated among the layers in the vicinity of the surface of the particles are deactivated through oxidation. The prolongation of the release time of H$_2$S due to the contact with oxygen was not observed, and it is estimated that the phenomenon occurs since the effect of prolonging the release time by the porous cover in the form of sandwich is larger than the same effect by the contact with oxygen.

Examples 28 to 42

In these examples, it was confirmed that the sulfide ion-containing LDH that was subjected to a homogenization treatment of the compositional distribution thereof had higher hydrogen sulfide sustained releasability through enhancement of the sustained releasability in some cases.

In Examples 28 to 31, in the case where the sulfide ion-containing LDH was subjected to the homogenization of the compositional distribution (storage) at room temperature, the influence of the storage period on the H$_2$S release behavior was confirmed.

Figure 31:
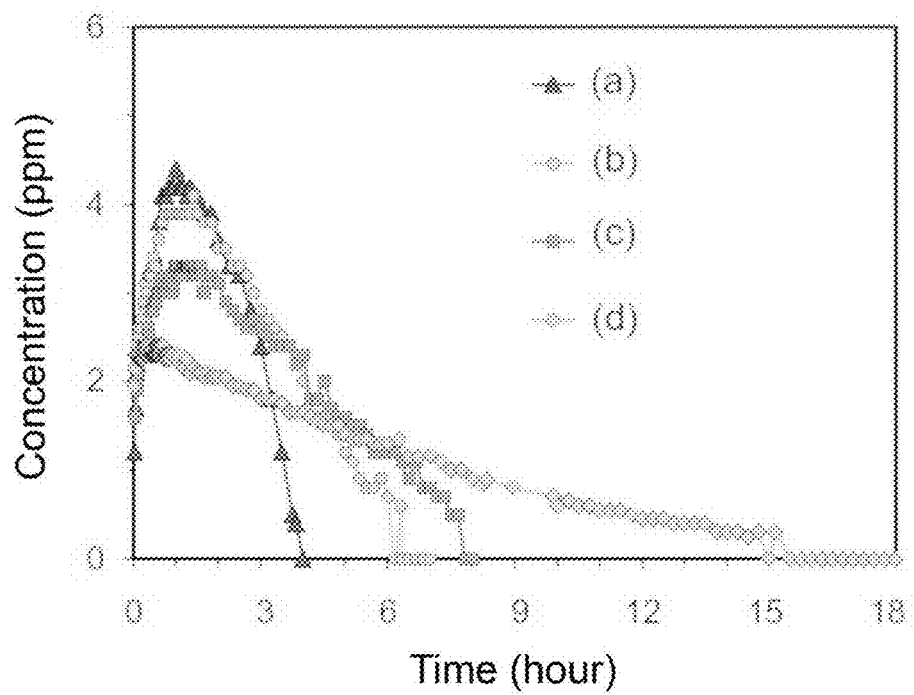
FIG. 31 is a graph showing the time course change of the concentration of $H_2S$ released from the sulfide ion-containing LDH in Examples 28 to 31 ((a): Example 28, (b): Example 29, (c): Example 30, (d): Example 31).

Packages of the sulfide ion-containing LDH obtained in the same manner as in Examples 25 to 27 each were stored at room temperature for a prescribed period of time to provide packages according to Examples 28 to 31. The storage period was 2 days for Example 28, 11 days for Example 29, 4 weeks for Example 30, or 6 months for Example 31. The packages each were opened, and two sheets of the hydrogen sulfide sustained release composites were taken out, immediately placed in a 13.5 mL glass container, and subjected to the H$_2$S release experiment in the same manner as in Example 1. FIG. 31 shows the time course change of the concentration of H$_2$S. In the figure, (a) shows the result of Example 28, (b) shows the result of Example 29, (c) shows the result of Example 30, and (d) shows the result of Example 31. It was confirmed from the result that the storage of the sulfide ion-containing LDH at room temperature for a prolonged period of time suppressed the release of H$_2$S in a high concentration in the initial stage of release, suppressed the release concentration over the release time, and prolonged the release time.

In Examples 32 to 36, in the case where the sulfide ion-containing LDH was stored at 60° C., the influence of the storage period on the H$_2$S release behavior was confirmed.

Figure 32:
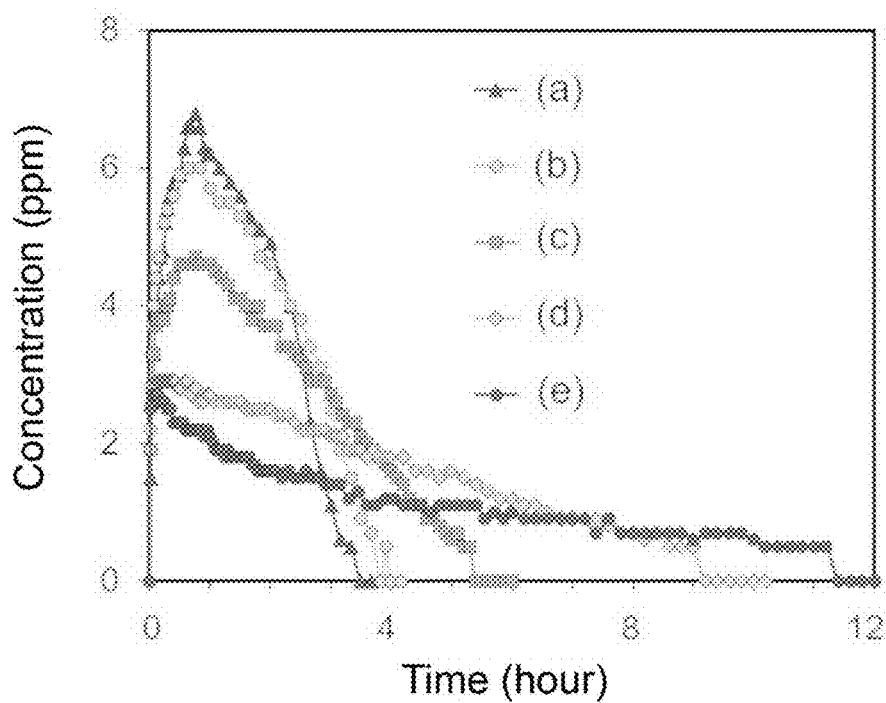
FIG. 32 is a graph showing the time course change of the concentration of $H_2S$ released from the sulfide ion-containing LDH in Examples 32 to 36 ((a): Example 32, (b): Example 33, (c): Example 34, (d): Example 35, (e): Example 36).

Packages of the sulfide ion-containing LDH obtained in the same manner as in Examples 25 to 27 each were stored at 60° C. for a prescribed period of time to provide packages according to Examples 32 to 36. The storage period was 5 hours for Example 33, 1 day for Example 34, 3 days for Example 35, or 7 days for Example 36, and these examples were compared to Example 32, which was the package immediately after the production. The resulting packages each were opened, and two sheets of the hydrogen sulfide sustained release composites were taken out, immediately placed in a 13.5 mL glass container, and subjected to the H$_2$S release experiment in the same manner as in Example 1. FIG. 32 shows the time course change of the concentration of H$_2$S. In the figure, (a) shows the result of Example 32, (b) shows the result of Example 33, (c) shows the result of Example 34, (d) shows the result of Example 35, and (e) shows the result of Example 36. It was confirmed from the result that the storage of the sulfide ion-containing LDH at 60° C. suppressed the release of H$_2$S in a high concentration in the initial stage of release, suppressed the release concentration over the release time, and prolonged the release time. Furthermore, it was found from the comparison between Examples 28 to 31 (FIG. 31) and Examples 33 to 36 (FIG. 32) that the effect of enhancing the sustained releasability was obtained in a shorter period of time in the storage at 60° C. than the storage at room temperature.

In Examples 37 to 40, the influence of the storage temperature of the sulfide ion-containing LDH on the H$_2$S release behavior was confirmed.

Figure 33:
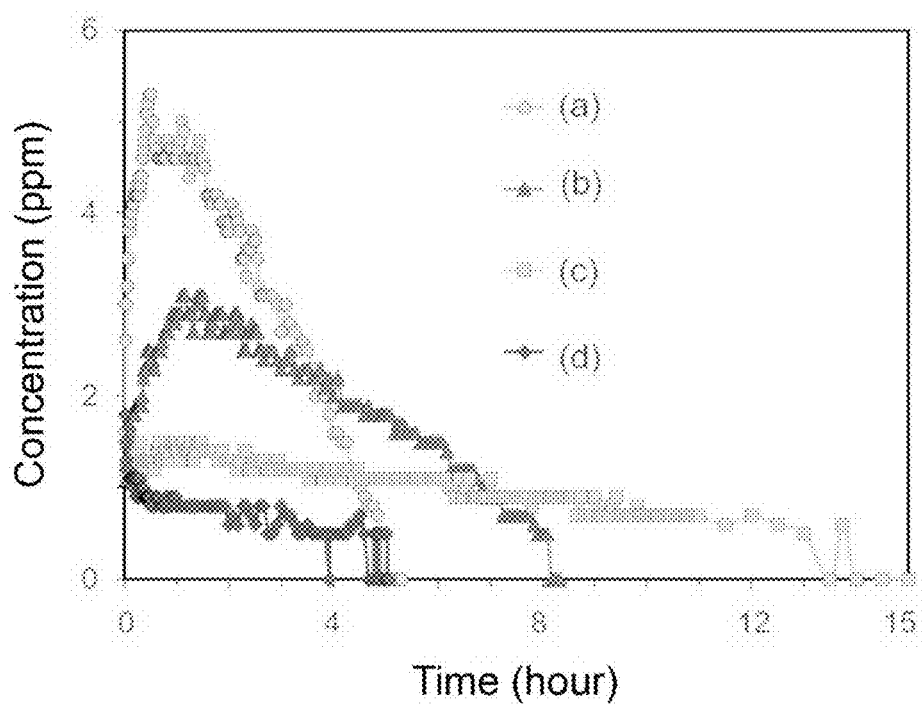
FIG. 33 is a graph showing the time course change of the concentration of $H_2S$ released from the sulfide ion-containing LDH in Examples 37 to 40 ((a): Example 37, (b): Example 38, (c): Example 39, (d): Example 40).

Packages of the sulfide ion-containing LDH obtained in the same manner as in Examples 25 to 27 each were stored at a prescribed temperature for 3 days to provide packages according to Examples 37 to 40. The storage temperature was room temperature for Example 37, 40° C. for Example 38, 80° C. for Example 39, or 100° C. for Example 40. The resulting packages each were opened, and two sheets of the hydrogen sulfide sustained release composites were taken out, immediately placed in a 13.5 mL glass container, and subjected to the H$_2$S release experiment in the same manner as in Example 1. FIG. 33 shows the time course change of the concentration of H$_2$S. In the figure, (a) shows the result of Example 37, (b) shows the result of Example 38, (c) shows the result of Example 39, and (d) shows the result of Example 40. It was confirmed from the result that with a higher storage temperature of the sulfide ion-containing LDH, the maximum concentration of H$_2$S released after the storage for a certain period of time was more suppressed. At a storage temperature of 100° C., the concentration of hydrogen sulfide was close to 0.4 ppm as the detection limit of the sensor, and the value after 5 hours from the start of release was not able to observe, but the release in a low concentration for a long period of time was considered to continue after 5 hours.

The result of Examples 28 to 40 can be understood as a result that in the case where the sulfide ion-containing LDH is stored for a certain period of time, HS$^-$ and/or S$_k^-$ in the vicinity of the surface is diffused to the interior to reduce the heterogeneity in distribution, and thus in contact with the air atmosphere, HS$^-$ and/or S$_k^{2-}$ in the interior is released late.

In Examples 41 and 42, the H$_2$S release behavior in the case where the storage temperature of the sulfide ion-containing LDH was lower than room temperature was confirmed.

Figure 34:
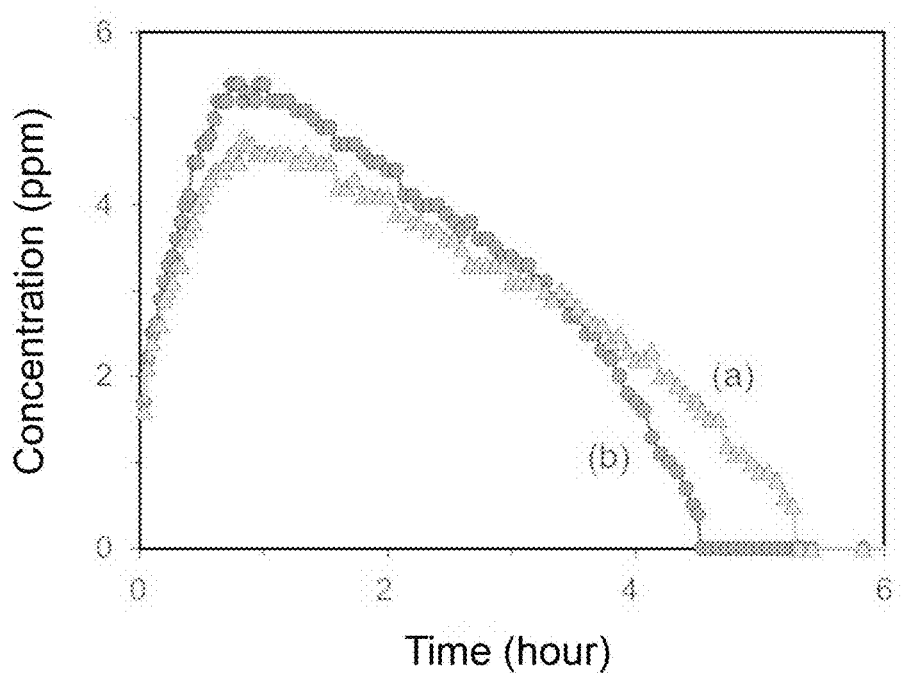
FIG. 34 is a graph showing the time course change of the concentration of $H_2S$ released from the sulfide ion-containing LDH in Examples 41 and 42 ((a): Example 41, (b): Example 42).

Packages of the sulfide ion-containing LDH obtained in the same manner as in Examples 25 to 27 each were stored in a refrigerator at 3.4° C. for Example 41 or in a freezer at −10.2° C. for Example 42, each for one week. The resulting packages each were opened, and two sheets of the hydrogen sulfide sustained release composites were taken out, immediately placed in a 13.5 mL glass container, and subjected to the H$_2$S release experiment in the same manner as in Example 1. FIG. 34 shows the time course change of the concentration of H$_2$S. In the figure, (a) shows the result of Example 41 and (b) shows the result of Example 42. It was confirmed from the result that the storage of the sulfide ion-containing LDH at a temperature lower than room temperature did not contribute to the enhancement of the sustained releasability, but well retained the sustained releasability immediately after the synthesis. It is considered that the phenomenon occurs since the change of the distribution state of the sulfide ion is suppressed, and suggests the usefulness of the storage at low temperature for the suppression of the change of the release characteristics.

Examples 43 to 45

In these examples, the sulfide ion-containing LDH, from which a part of hydrogen sulfide contained was released in advance, had higher hydrogen sulfide sustained releasability through enhancement of the sustained releasability.

10 mg of the Cl⁻MgAl-LDH2 prepared in the same manner as in Example 2 was placed in a 20 mL glass vial. Separately, 19.3 mg of $Na_2S·9H_2O$ was dissolved in 10 mL of degassed methanol to prepare a $Na_2S$ solution. The $Na_2S$ solution was added to the glass vial and dispersed by ultrasonification, and then the mixture was reacted for 2 days in the glass vial hermetically sealed. The entire amount of the liquid after the reaction was filtered with a membrane filter having a pore diameter of 0.2 µm, and the filtered matter (residue) was washed with degassed methanol. Thereafter, the membrane filter having the residue thereon was folded in half with the residue directed inside, and cut into ¼ to provide a membrane filter piece. The resulting membrane filter piece was placed on an adhesive surface of a porous tape, and another porous tape was adhered thereon to hold the membrane filter piece, so as to form a sandwich cover. After cutting the excess portions of the tape while preventing the membrane filter from being cut, the assembly was dried in vacuum for approximately 30 minutes, and placed in a 13.5 mL glass container (packaging material), and the container was hermetically sealed to provide a package. Separately, the membrane filter piece was directly dried in vacuum for approximately 30 minutes, and placed in a 13.5 mL glass container (packaging material), and the container was hermetically sealed to provide another package. The operation up to this point was performed in a glove box with a nitrogen atmosphere.

The package housing the specimen having the sandwich cover (i.e., the hydrogen sulfide sustained release composite) was opened in the air atmosphere, and the sulfide ion-containing LDH was aerated by supplying air controlled to be 20° C. and 50% RH thereto at a flow rate of 100 cc/min for 15 minutes. Thereafter, the interior of the package was purged by supplying nitrogen gas thereto at a flow rate of 500 cc/min for 15 minutes, so as to provide a specimen according to Example 43. The package housing the specimen having the sandwich cover (i.e., the hydrogen sulfide sustained release composite) was opened in the air atmosphere to provide a specimen according to Example 44, and the package directly housing the membrane filter piece was opened to provide a specimen according to Example 45.

Figure 35:
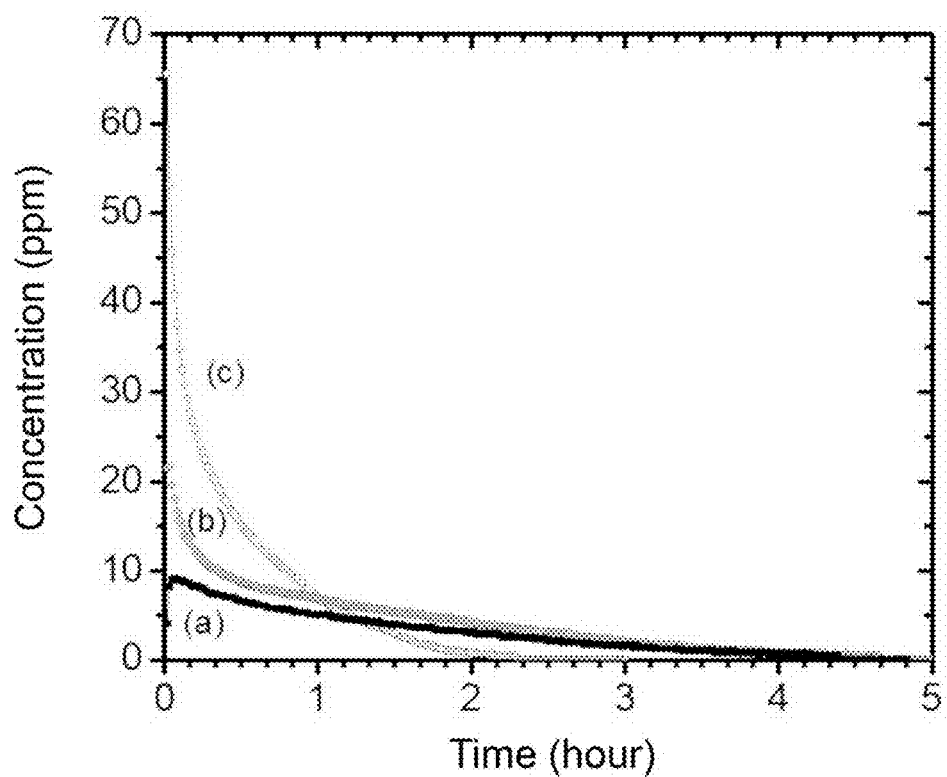
FIG. 35 is a graph showing the time course change of the concentration of $H_2S$ released from the sulfide ion-containing LDH in Examples 43 to 45 ((a): Example 43, (b): Example 44, (c): Example 45).

The specimens according to Examples 43 to 45 were subjected to the $H_2S$ release experiment in the same manner as in Example 1. FIG. 35 shows the time course change of the concentration of $H_2S$. In the figure, (a) shows the result of Example 43, (b) shows the result of Example 44, and (c) shows the result of Example 45. It was found from the comparison between (a) and (b) in the figure that in the case where a part of hydrogen sulfide was released from the sulfide ion-containing LDH by aeration in advance, the release of $H_2S$ in a high concentration in the initial stage of release was suppressed, and the release concentration was suppressed over the release time. It is considered that the phenomenon occurs since hydrogen sulfide derived from the hydrogen sulfide source attached to the surface of the particles of the sulfide ion-containing LDH, the hydrogen sulfide source retained in the voids among the particles, and $HS^-$ and/or $S_k^{2-}$ intercalated among the layers in the vicinity of the surface of the particles is released to remove the hydrogen sulfide sources. It was confirmed from the comparison between (b) and (c) in the figure that the housing of the sulfide ion-containing LDH in the porous cover or container provided the effect of enhancing the sustained releasability, as similar to Examples 16 to 19.

INDUSTRIAL APPLICABILITY

According to the present invention, an inorganic solid material that sustainably releases hydrogen sulfide at ordinary temperature in the air atmosphere can be obtained easily and safely.

The resulting sulfide ion-containing LDH generates hydrogen sulfide by bringing into contact with air, without heating or addition of water, and the hydrogen sulfide concentration can be readily controlled since the hydrogen sulfide concentration is approximately proportional to the proportion of the sulfide ion intercalated among the layers. Accordingly, it is expected to be suitable as a medical hydrogen sulfide gas supply source for exposing at a low concentration for a long period of time. Specific examples of the application include a remedy by locally generating hydrogen sulfide in the vicinity of the affected area in a concentration that is not harmful to the living body.

In addition to the medical field, hydrogen sulfide is also used in the industrial fields and the research fields handling heavy metals due to the affinity thereof to heavy metals and the like, and the present invention is greatly expected as a hydrogen sulfide supply source in these fields, substituting the pressure cylinders having heavy weights, which are difficult in handling and involve the risk of accident.

In the present invention, furthermore, the production cost can be suppressed since commercially available inexpensive LDH and sulfides can be used as the raw materials, and no special production equipment is required.

Moreover, the inorganic solid material of the present invention retains the structure of LDH after completing the release of hydrogen sulfide, and thus is useful as a chemically stable and highly safe hydrogen sulfide sustained release agent or sustained release composite.

REFERENCE SIGN LIST

1: Porous tape
2: Membrane filter
3: Sulfide ion-containing LDH

The invention claimed is:

1. A method for producing a package comprising a layered double hydroxide having $HS^-$ and/or $S_k^{2-}$ (wherein k represents a positive integer) intercalated among layers, and a packaging material hermetically housing the layered double hydroxide, the method comprising:
preparing a layered double hydroxide having an anion other than $HS^-$ and/or $S_k^{2-}$ (wherein k represents a positive integer) intercalated among layers, and a solvent;
making the solvent to contain $HS^-$ and/or $S_k^{2-}$ under a nitrogen gas or rare gas atmosphere to provide a solution;
bringing the layered double hydroxide having an anion other than $HS^-$ and/or $S_k^{2-}$ (wherein k represents a positive integer) intercalated among layers into contact with the solution under a nitrogen gas or rare gas atmosphere;
separating a solid matter after the contact from the solution, and washing and drying the solid matter, under a nitrogen gas or rare gas atmosphere; and
sealing the solid matter after drying in a packaging material.

2. The method for producing the package according to claim 1, wherein the layered double hydroxide having an anion other than $HS^-$ and/or $S_k^{2-}$ intercalated among layers contains $CO_3^{2-}$ as the anion, and at least a part of the $CO_3^{2-}$ is removed from an interlayer of the layered double hydroxide, which is then brought into contact with the solvent containing $HS^-$ and/or $S_k^{2-}$.

3. The method for producing the package according to claim 1, wherein the method further comprises, preceding making the solvent to contain $HS^-$ and/or $S_k^{2-}$, decreasing concentrations of oxygen and carbon dioxide in the solvent, and the solid matter is washed with a solvent having decreased concentration of oxygen and carbon dioxide.

4. The method for producing the package according to claim 1, wherein the solvent is made to contain $HS^-$ and/or $S_k^{2-}$ by mixing a compound represented by the following general formula (2):

$$MH_pS_q \cdot mH_2O \quad (2)$$

wherein in the formula (2), M represents an alkali metal or an alkaline earth metal; p represents 0 or 1; q represents a number satisfying $0.5 \leq q \leq 6.0$; and m represents a number varying depending on a humidity of an environment.

5. The method for producing the package according to claim 1, wherein the solid matter after the contact is subjected to a treatment of changing a distribution state of $HS^-$ and/or $S_k^{2-}$.

6. The method for producing the package according to claim 5, wherein the treatment includes a treatment of washing the solid matter with a liquid containing water.

7. The method for producing the package according to claim 5, wherein the treatment includes a treatment of bringing the solid matter after the drying into contact with oxygen.

8. The method for producing the package according to claim 5, wherein the treatment includes a homogenization treatment of a compositional distribution of the solid matter after the drying.

9. The method for producing the package according to claim 5, wherein the treatment includes a treatment of releasing a part of $HS^-$ and/or $S_k^{2-}$ (wherein k represents a positive integer) contained in the solid matter from the solid matter after the drying as hydrogen sulfide.

10. A method for producing a package comprising a layered double hydroxide having $HS^-$ and/or $S_k^{2-}$ (wherein k represents a positive integer) intercalated among layers, and a packaging material hermetically housing the layered double hydroxide, the method comprising:
preparing an aqueous solution containing plural kinds of metal ions, and an alkali solution containing $HS^-$ and/or $S_k^{2-}$ (wherein k represents a positive integer);
mixing the aqueous solution and the alkali solution under a nitrogen gas or rare gas atmosphere to provide a precipitate;
ripening the solution containing the precipitate under a nitrogen gas or rare gas atmosphere;
separating the precipitate after the ripening from the solution, and washing and drying the precipitate, under a nitrogen gas or rare gas atmosphere; and
sealing a solid matter after the drying in a packaging material.

11. A hydrogen sulfide sustained release agent comprising a layered double hydroxide having $HS^-$ and/or $S_k^{2-}$ (wherein k represents a positive integer) intercalated among layers,
wherein when the hydrogen sulfide sustained release agent is conducted to a $H_2S$ release experiment, a hydrogen sulfide concentration increases to a maximum value, and then a concentration thereof gradually reduces; and
the hydrogen sulfide in a concentration of 1/100 or more relative to the maximum value is released continuously for 30 minutes or more.

12. The hydrogen sulfide sustained release agent according to claim 11, wherein the layered double hydroxide is represented by the following general formula (1):

$$Q_xR(OH)_{2(x+1)}\{(HS^-,0.5S_k^{2-})_yZ_t\} \cdot nH_2O \quad (1)$$

wherein in the formula (1), Q represents a divalent metal ion; R represents a trivalent metal ion; Z represents an anion other than $HS^-$ and/or $S_k^{2-}$; x, y, and t represent numbers satisfying $1.8 \leq x \leq 4.2$, $0.01 \leq y \leq 2.0$, and $0 \leq t \leq 1.0$; and n represents a number varying depending on a humidity of an environment.

13. The hydrogen sulfide sustained release agent according to claim 11, wherein the layered double hydroxide is a granulated material or a powder compact material.

14. The hydrogen sulfide sustained release agent according to claim 11, wherein the layered double hydroxide is mixed with an extender or a diluent.

15. The hydrogen sulfide sustained release agent according to claim 11, wherein the layered double hydroxide has at least $HS^-$ intercalated among layers.

16. The hydrogen sulfide sustained release agent according to claim 11, wherein said concentration is more than 0.35 ppm.

17. A method for generating hydrogen sulfide, comprising using the hydrogen sulfide sustained release agent according to claim 11.

18. A hydrogen sulfide sustained release composite comprising the hydrogen sulfide sustained release agent according to claim 11 housed in a porous cover or a porous container.

19. A method for generating hydrogen sulfide, comprising using the hydrogen sulfide sustained release composite according to claim 18.

* * * * *